United States Patent
Yoo et al.

(10) Patent No.: US 9,492,344 B2
(45) Date of Patent: Nov. 15, 2016

(54) UNIFIED VISION TESTING AND/OR TRAINING

(75) Inventors: Herb Yoo, Beaverton, OR (US); Alan W. Reichow, Beaverton, OR (US); Jonathan Brown, Portland, OR (US); Ryan C. Coulter, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 894 days.

(21) Appl. No.: 12/534,637

(22) Filed: Aug. 3, 2009

(65) Prior Publication Data
US 2011/0027766 A1    Feb. 3, 2011

(51) Int. Cl.
| A61B 13/00 | (2006.01) |
|---|---|
| A61H 5/00 | (2006.01) |
| A61B 3/032 | (2006.01) |
| A61B 3/028 | (2006.01) |

(Continued)

(52) U.S. Cl.
CPC ............. *A61H 5/00* (2013.01); *A61B 3/032* (2013.01); *A61B 3/005* (2013.01); *A61B 3/0033* (2013.01); *A61B 3/0041* (2013.01); *A61B 3/0058* (2013.01); *A61B 3/022* (2013.01); *A61B 3/024* (2013.01); *A61B 3/028* (2013.01); *A61B 3/06* (2013.01); *A61B 3/18* (2013.01); *A61B 5/742* (2013.01); *A61B 5/7445* (2013.01); *A61B 5/7475* (2013.01); *A61H 2201/5007* (2013.01); *A61H 2201/5046* (2013.01); *A61H 2201/5048* (2013.01); *A61H 2201/5097* (2013.01); *G06F 1/1647* (2013.01); *G06F 1/1649* (2013.01)

(58) Field of Classification Search
CPC .. A61B 3/0033; A61B 3/0041; A61B 3/005; A61B 3/0058; A61B 3/032; A61B 3/022; A61B 3/024; A61B 3/028; A61B 3/04; A61B 3/06; A61B 3/18; A61B 5/742; A61B 5/7445; A61B 5/7475; A61B 3/08; G06F 1/1601; G06F 1/1637; G06F 1/1647; G06F 1/1649
USPC ........ 348/77, 78, 14.03, 14.07; 351/200, 201, 351/203, 208, 222, 239, 246; 600/558
See application file for complete search history.

(56) References Cited

U.S. PATENT DOCUMENTS

| 3,861,790 A | 1/1975 | Tamura |
|---|---|---|
| 4,294,522 A * | 10/1981 | Jacobs .................. A61B 3/02 351/203 |

(Continued)

FOREIGN PATENT DOCUMENTS

| CN | 101065766 | 10/2007 |
|---|---|---|
| WO | WO 2008128183 | 10/2008 |
| WO | WO 2008128190 | 10/2008 |

OTHER PUBLICATIONS

International Search Report and Written Opinion, International Application PCT/US2010/044257, 15 pages.

(Continued)

*Primary Examiner* — Devin Henson
(74) *Attorney, Agent, or Firm* — Shook, Hardy & Bacon L.L.P.

(57) ABSTRACT

Unified vision testing and/or training kiosk may utilize display devices and input devices to administer a number of visual testing and/or training tasks to an individual. One or more display devices may provide desired resolution, geometry, and/or touch sensitivity. One or more input devices may receive inputs of different types from different positions relative to a display device. Methods of visual testing and/or training may utilize the one or more display devices, one or more input devices, and/or other types of equipment to evaluate and/or improve the visual abilities of an individual.

8 Claims, 63 Drawing Sheets

(51) Int. Cl.

| G06F 1/16 | (2006.01) |
|---|---|
| A61B 3/00 | (2006.01) |
| A61B 5/00 | (2006.01) |
| A61B 3/18 | (2006.01) |
| A61B 3/024 | (2006.01) |
| A61B 3/02 | (2006.01) |
| A61B 3/06 | (2006.01) |

(56) References Cited

U.S. PATENT DOCUMENTS

| 5,050,982 | A | | 9/1991 | Meissner | |
|---|---|---|---|---|---|
| 5,478,239 | A | | 12/1995 | Fuerst | |
| 5,539,481 | A | * | 7/1996 | Vax | A61H 5/00 351/203 |
| 6,755,525 | B2 | | 6/2004 | Reichow | |
| 6,811,258 | B1 | | 11/2004 | Grant | |
| 6,893,127 | B2 | | 5/2005 | Reichow | |
| 7,073,208 | B2 | | 7/2006 | Penque | |
| 7,211,050 | B1 | | 5/2007 | Caplygin | |
| 7,350,921 | B2 | * | 4/2008 | Ridings | A61B 3/032 351/237 |
| 7,393,104 | B2 | * | 7/2008 | Hara | A61B 3/028 351/222 |
| 2004/0057013 | A1 | | 3/2004 | Cappo et al. | |
| 2005/0041208 | A1 | | 2/2005 | Winterbotham | |
| 2005/0046794 | A1 | | 3/2005 | Silvestrini et al. | |
| 2005/0225720 | A1 | | 10/2005 | Ridings | |
| 2006/0023163 | A1 | | 2/2006 | Foster | |
| 2006/0087618 | A1 | * | 4/2006 | Smart | A61B 3/005 351/222 |
| 2008/0189173 | A1 | * | 8/2008 | Bakar | G06Q 30/02 705/14.14 |
| 2009/0153796 | A1 | | 6/2009 | Rabner | |

OTHER PUBLICATIONS

Reichow, et al., "Introduction to Behavioral Optometry", Sports Vision, 1993, 75 pages, Optometric Extension Program Foundation, United States.

Ferreira, "An Overview of Research in Sports Vision: its History and an Optometric Perspective", The South African Optometrist, Dec. 2003, pp. 142-149, vol. 62, No. 4, Auckland Park, South Africa.

Coffey, et al., "Visual Performance Enhancement in Sports Optometry", Sports Vision 1995, pp. 158-177, Butterworth-Heinermann, United States.

Cardall, "Contact Lenses in Sport: a General Overview", Optician, Jan. 13, 2006, pp. 22-25, vol. 231, No. 6034, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States.

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

\* cited by examiner

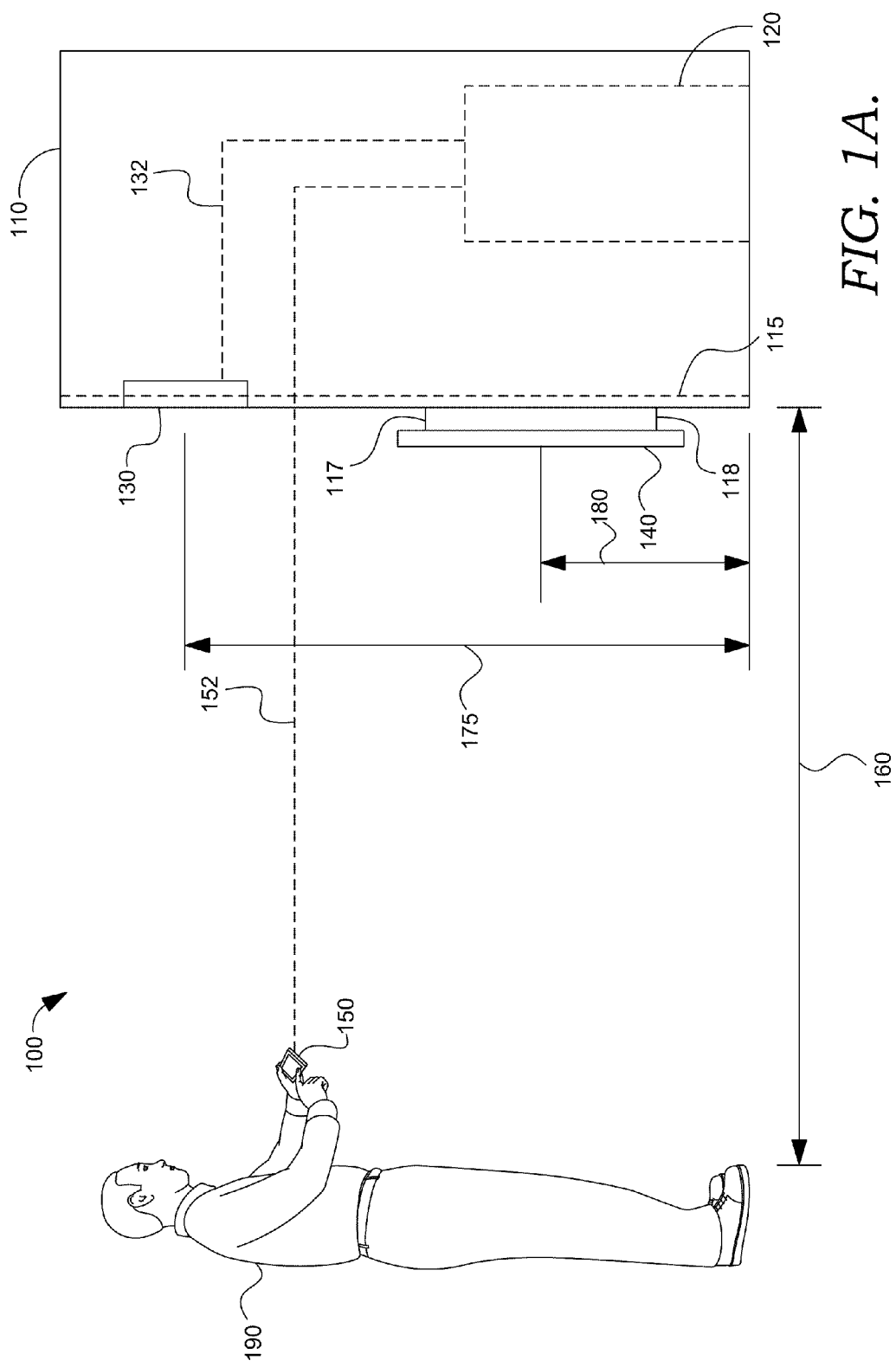

UNIFIED VISION TESTING AND/OR TRAINING

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates to vision testing and/or training. More particularly, the present invention relates to a unified system and method for testing and/or training a plurality of visual skills and abilities of an individual and an efficient time and using compact, multi-use instrumentation.

BACKGROUND OF THE INVENTION

Various types of vision tests have been developed to measure the visual and related physiological and/or neurological abilities of individuals. Often, such tests are performed in the office of an optometrist or other health care professional. In such an office setting, a clinician may have access to a wide array of equipment with which to test the visual and related abilities of an individual. However, testing the visual abilities of an individual in other, non-clinical, settings can prove difficult, as much of the equipment developed for vision testing is difficult to transport or requires carefully controlled conditions or configurations. Moreover, equipment required for vision testing may require a great deal of space, such as an entire optician's office, and therefore difficult to integrate into another type of facility, such as an athletic training facility. Moreover, vision testing can be a time-consuming process, with multiple equipment changes, adjustments, and the like requiring a lengthy period of time to complete a single thorough assessment of an individual. Similarly, vision training equipment and methodologies have been developed, but that vision training often requires specialized equipment and/or exercises for individual visual skills.

BRIEF SUMMARY OF THE INVENTION

The present invention provides a unified system and method for testing and/or training the visual abilities and the related physiological and/or neurological abilities of an individual. By combining the equipment used for vision testing and/or training into a compact station or kiosk, the number of equipment changes for vision testing and/or training and the amount of space required for such equipment is reduced. Systems in accordance with the present invention may utilize a relatively small predetermined number of display devices to present visual indicia to an individual and a predetermined number of input devices to receive inputs from the individual in response to display of a visual indicia. Visual testing and/or training may comprise one or more tasks, such as identifying a visual trait possessed by a visual indicia, selecting one of a plurality of visual indicia, etc. A single display device and/or input device may be used for a plurality of tests for which that display device and/or input device is suited. For example, a high resolution display device, such as a high definition monitor, may be used to display visual indicia used to measure the static visual clarity of an individual. The same high resolution display device may also be used to test and/or train other visual skills of the individual that benefit from a high resolution display device, such as the contrast sensitivity, depth perception, and the near-far focusing ability of the individual. By way of further example, a wide aspect display device, which may optionally be a different display device then a high resolution display device, may be used to test and/or train visual skills such as pursuit and capture at a relatively far distance, or may also comprise a touch sensitive screen or may be combined with a touch sensitive screen overlay to test and/or train visual skills such as eye-hand coordination, visual perception span, visual decision making (go/no-go), reaction time, and the like. Input devices may comprise, for example, a multi-touch device for use at relatively far distances from a display device to test the visual skills of an individual at distances such as optical infinity, or a touch sensitive screen or a touch sensitive screen overlay, such as for use at a near distance where an individual may physically touch the screen. Further, a single multi-touch device may comprise both an output device and an input device for testing and/or training at least some visual skills, such as near-far focusing ability. Additional visual testing and or training equipment may be utilized as part of the methodology of unified vision testing in accordance with the present invention as well. For example, additional equipment may be utilized to perform testing and/or training skills such as a determination of the near point of convergence for an individual.

Additional objects, advantages, and novel features of the invention will be set forth in part in the description which follows, and in part will become apparent upon examination of the following, or may be learned by practice of the invention.

BRIEF DESCRIPTION OF THE SEVERAL VIEWS OF THE DRAWING

The present invention is described in detail below with reference to the attached drawing figures, wherein:

FIG. 1A illustrates a system in accordance with the present invention while an individual's visual skills are tested and/or trained at optical infinity;

FIG. 51A-41D illustrate an exemplary embodiment of reaction time testing and training in accordance with embodiments of the present invention;

DETAILED DESCRIPTION OF THE INVENTION

Figure 1B:
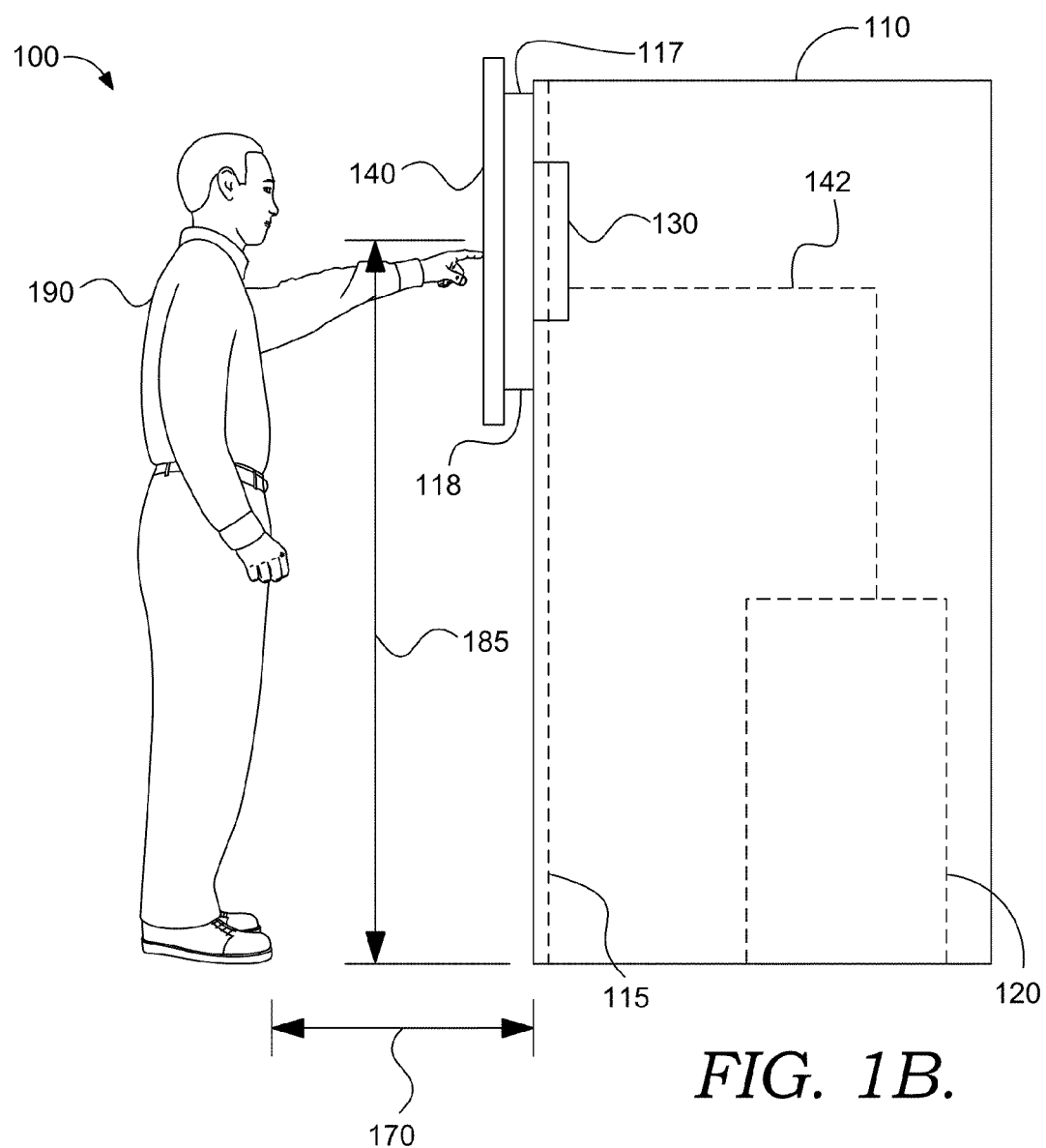
FIG. 1B illustrates a system in accordance with the present invention while an individual's visual skills are tested and/or trained at a visually near distance.

The subject matter of the present invention is described with specificity herein to meet statutory requirements. However, the description itself is not intended to limit the scope of this patent. Rather, the inventors have contemplated that the claimed subject matter might also be embodied in other ways to include different steps or combination(s) of steps and/or components similar to those described herein, in conjunction with other present or future technologies.

Referring now to FIG. 1A, a unified vision testing and/or training system 100 in accordance with the present invention is illustrated. A kiosk 110 may comprise a first display device 130, a second display device 140 and a control unit 120. A supportive frame 115 may provide structural support to kiosk 110, to rigidly hold first display device 130 in place, and to provide slideable support to second display device 140. However, kiosk 110 may be constructed to be self supporting so that supportive frame 115 may be omitted. First display device 130 may comprise, for example, a high definition monitor. First display device 130 may be rigidly affixed at a first height 175, which may be approximately eye level for a typical individual undergoing visual testing and/or training, such as individual 190. The appropriate height of first display device 130 may vary based upon whether kiosk 110 is intended for use with adults, children, men, women, etc., as well as the posture used by individuals during testing with kiosk 110. Further, the height of first display device 130 may be adjustable if desired. Second display device 140 may be slideably affixed to supportive frame 115 via a first movable coupling 117 and second movable coupling 118 at a first height 180. Of course, any type of movable couplings in varying numbers, including more or fewer than the two illustrated herein, may be utilized. Second display device 140 may be slideably affixed to supportive frame directly or indirectly, and may be moved through any means, such as by being adjusted by a user or administrator, by use of a motor driven device, through the use of servos, hydraulics, etc., or by any other mechanism. The adjustable height of second display device 140, as well as first display device 130 if desired, may be particularly useful for testing individuals having varying heights, particularly for visually near testing and/or for use as a touch sensitive input device. However, second display device 140 may be affixed in place without departing from the scope of the present invention. Second display device 140 may comprise a wide screen monitor that will completely obscure first display device 130 when slideably adjusted to be at approximately eye level for an individual subject to testing, such as individual 190. As explained more fully below, second display device 140 may comprise a touch sensitive display device that may be used both as a display device and as an input device.

As illustrated in FIG. 1A, individual 190 is engaged in visual testing and/or training at a first distance 160 from kiosk 110. First distance 160 may comprise, for example, optical infinity for individual 190. Optical infinity refers to a distance at which the eyes of individual 190 may focus on a displayed indicia with the visual axis of the eyes oriented in a parallel fashion, i.e., with zero convergence. A suitable distance for first distance 160 may, for example, be approximately sixteen feet, which approximates optical infinity. Of course, other distances may also be used, both that approximate or exceed optical infinity, as well as distances that are well below optical infinity. As illustrated in FIG. 1A, individual 190 may respond to visual indicia displayed on first display device 130 using first input device 150. As illustrated in FIG. 1A, first input device 150 may comprise a multi-touch input device. The use of a multi-touch input device is described in more detail below.

Referring now to FIG. 1B, system 100 is illustrated with individual 190 engaged in visual testing and/or training at a visually near distance to kiosk 110. As illustrated in FIG. 1B, second display device 140 has been slideably positioned at a second distance 185. Second distance 185 may be sufficiently similar to first distance 175 (shown in FIG. 1A) so as to occlude first display device 130 from the view of individual 190 with second display device 140. As shown in FIG. 1B, individual 190 is positioned at a second distance 170 from second display device 140. As illustrated in FIG. 1B, second display device 140 may comprise a touch sensitive screen, such that individual 190 may enter inputs in response to visual indicia displayed on second display device 140 by physically touching second display device 140. Of course, other input devices, such as joystick(s), buttons, keyboards, a multi-touch device, voice recognition, etc., may be used.

As illustrated in FIGS. 1A and 1B, the display of visual indicia on first display device 130 and/or second display device 140 may be controlled by a control unit 120. Control unit 120 may comprise any type of computing device and may operate using appropriately configured software installed thereon. Control unit 120 may comprise processors, memory devices, hard drives, flash memory, and the like. Control unit 120 may further utilize wired and/or wireless network connections to interact with other computing devices and/or storage devices. Control unit 120 may be operably connected to first display device 130 via first connection 132. Similarly, control unit 120 may be operably connected to second display device 140 via second connection 142. Control unit 120 may be operably connected to input device 150 via third connection 152. Any and each of first connection 132, second connection 142, and/or third connection 152 may utilize any protocol or format, and may utilize differing protocols and formats. For example, connection 152 may advantageously be a wireless connection utilizing various 802.11 protocols and/or Bluetooth protocols.

In an exemplary embodiment, the control unit 120 is a computing device having a processor and memory. A computing device typically includes a variety of computer-readable media. By way of example, and not limitation, computer-readable media may comprise Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices, or any other medium that can be used to encode desired information and be accessed by a computing device.

While both FIGS. 1A and 1B, as well as subsequent drawings, illustrate examples wherein an individual 190 engaged in visual testing and/or training uses a gaze angle substantially perpendicular to the first display device 130 and/or second display device 140, other gaze angles may also be used in visual testing and/or training in accordance with the present invention. In many activities, such as athletic endeavors, accurately and/or quickly perceiving visual information from a variety of gaze angles has critical importance. Systems and methods in accordance with the present invention may test and/or train visual skills at any gaze angle and may particularly address gaze angles of importance for a specific activity of interest to an individual 190. Such non-perpendicular gaze angles may be above, below, to the left, and/or to the right of a perpendicular gaze angle. Systems and methods in accordance with the present invention may be used to test and/or train any number of gaze angles for an individual 190.

Figure 2:
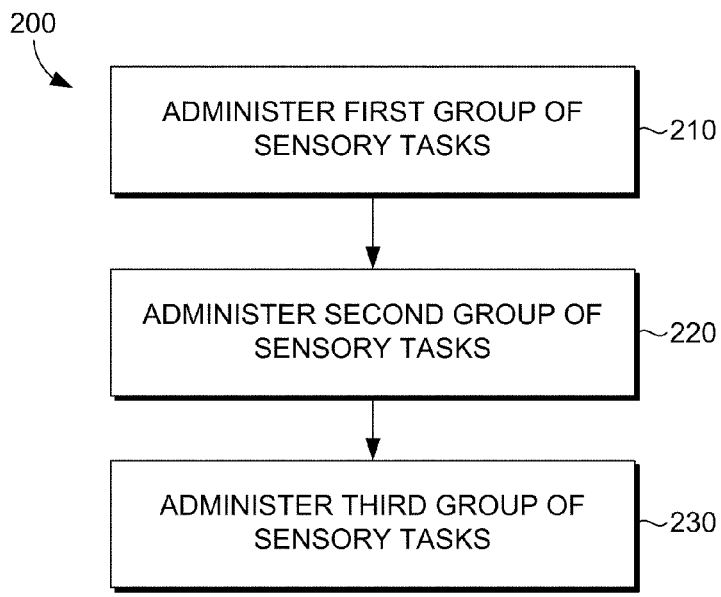
FIG. 2 illustrates a method for unified vision testing and/or training in accordance with the present invention.

Referring now to FIG. 2, a method 200 for administering sensory tests and/or training to an individual is illustrated. In step 210, a first group of sensory testing and/or training tasks may be administered to an individual. The group of tasks administered in step 210 may utilize a common display device, a common input device, a common position or orientation of the individual being tested and/or trained relative to equipment, or other points of commonality in terms of equipment and/or positioning. In step 220, a second group of sensory testing and/or training tasks may be administered to the individual. The second group of sensory tasks administered in step 220 may utilize a common display device, a common input device, a common position or orientation of the individual being tested and/or trained relative to equipment, or other points of commonality in terms of equipment and/or positioning that differs from the first group of sensory tasks administered in step 210. In step 230, a third group of sensory testing and/or training tasks may be administered to the individual. The third group of sensory tests administered in step 230 may utilize a common display device, a common input device, a common position or orientation of the individual being tested and/or trained relative to equipment, or other points of commonality in terms of equipment and/or positioning that differs from the first group of sensory tasks administered in step 210 and the second group of sensory tasks administered in step 220. Each of the first group of sensory tasks, the second group of sensory tasks, and the third group of sensory tasks may comprise one or more type of sensory task administered one or more times.

Figure 3:
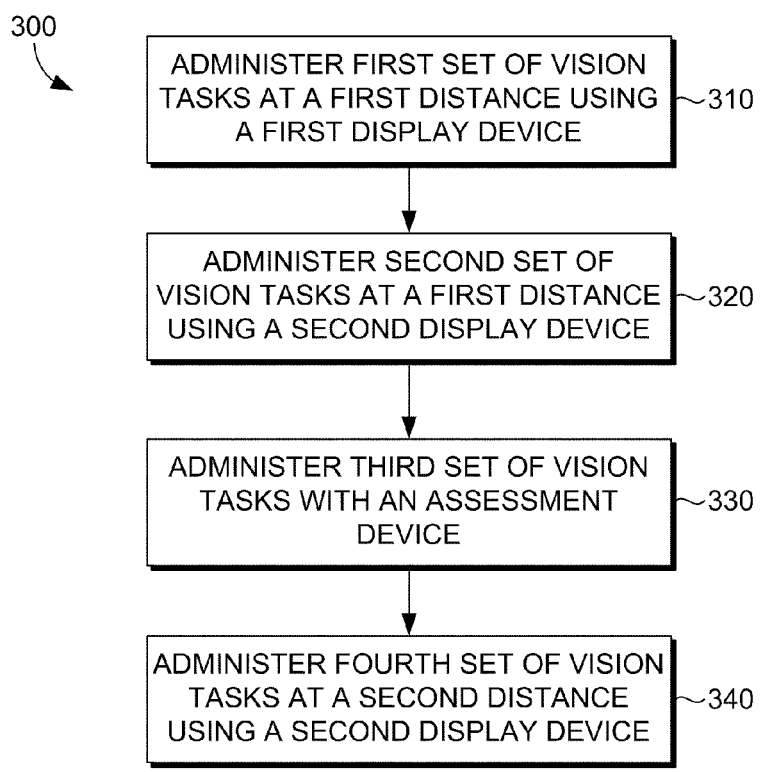
FIG. 3 illustrates a further method for unified vision testing and/or training in accordance with the present invention.

Referring now to FIG. 3, a further method 300 for administering vision tests and/or training is illustrated. In step 310, a first set of vision testing and/or training tasks may be administered to an individual at a first distance using a first display device. In step 320, a second set of vision testing and/or training tasks are administered at a first distance using a second display device. In step 330, a third set of vision testing and/or training tasks may be administered to the individual using an assessment device. The assessment device utilized in step 330 need not be a display device, but may be a non-display device assessment apparatus for testing and/or training visual skills, such as may be used to test visual abilities such as the near point of convergence of an individual. In step 340, a fourth set of vision testing and/or training tasks may be administered to the individual at a second distance using the second display device. The first display device and second display device utilized in method 300 may have different properties making them well adapted to different types of vision tests. For example, a high resolution display device may be particularly well adapted for use in testing and/or training visual skills such as visual clarity, contrast sensitivity, depth perception, and the like. However, screens having expansive dimensions may be better suited to testing and/or training visual skills such as saccadic target capture, visual perception span, eye hand coordination, reaction time and the like. Further, touch sensitive screens, or screens well-suited for utilizing a touch sensitive overlay, maybe well-suited for testing and/or training that requires a touch input in response to a displayed visual testing indicia.

Figure 4:
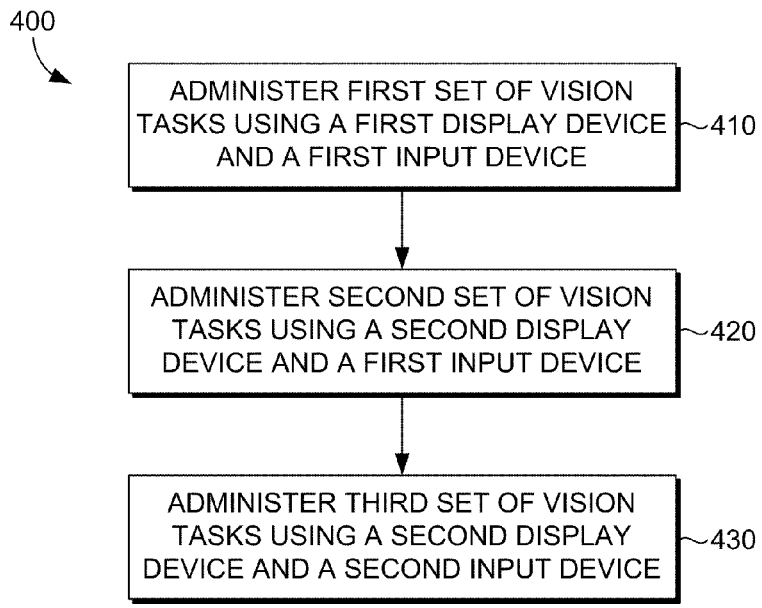
FIG. 4 illustrates a further method for unified vision testing and/or training in accordance with the present invention.

Referring now to FIG. 4, a further method 400 of administering vision testing and/or training in accordance with the present invention is illustrated. In step 410, a first set of vision testing and/or training tasks using a first display device and a first input device may be administered to an individual. In step 420, a second set of vision testing and/or training tasks using a second display device and the first input device may be administered to an individual. In step 430, a third set of vision testing and/or training tasks using a second display device and a second input device may be administered to the individual. As described above with regard to FIG. 3, the first display device and the second display device utilized for method of 400 may be selected for their particular traits and the types of tasks to be performed. Further, first input device and a second input device utilized for method 400 may be selected based upon their particular traits and the particular types of input to be received for certain types of vision tasks. For example, a multi-touch device that may communicate wirelessly with a control unit may be particularly useful for vision tasks performed at optical infinity or similarly distant from a display device. On the other hand, vision tasks performed optically near a display device may preferably utilize a touch sensitive screen, buttons, joysticks, and the like to receive inputs.

Figure 5:
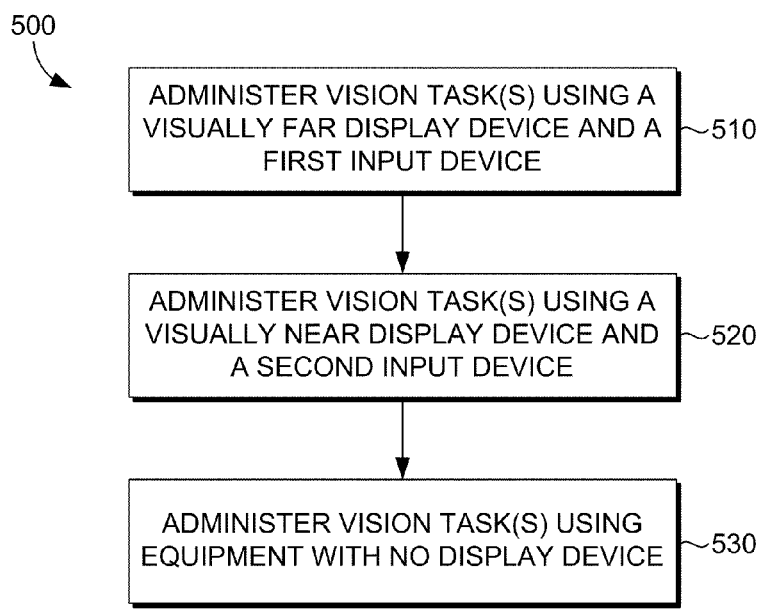
FIG. 5 illustrates a further method for unified vision testing and/or training in accordance with the present invention.

Referring now to FIG. 5, a further method 500 of administering vision testing and/or training in accordance with the present invention is illustrated. In step 510, one or more vision testing and/or training task using a visually far display device and a first input device are administered to an individual. A visually far display device may comprise a display device at or near optical infinity from the individual being tested. In step 520, one or more vision testing and/or training task using a visually near display device and a second input device may be administered to an individual. In step 530, one or more vision testing and/or training tasks using equipment with no display device may be administered to the individual.

Figure 6:
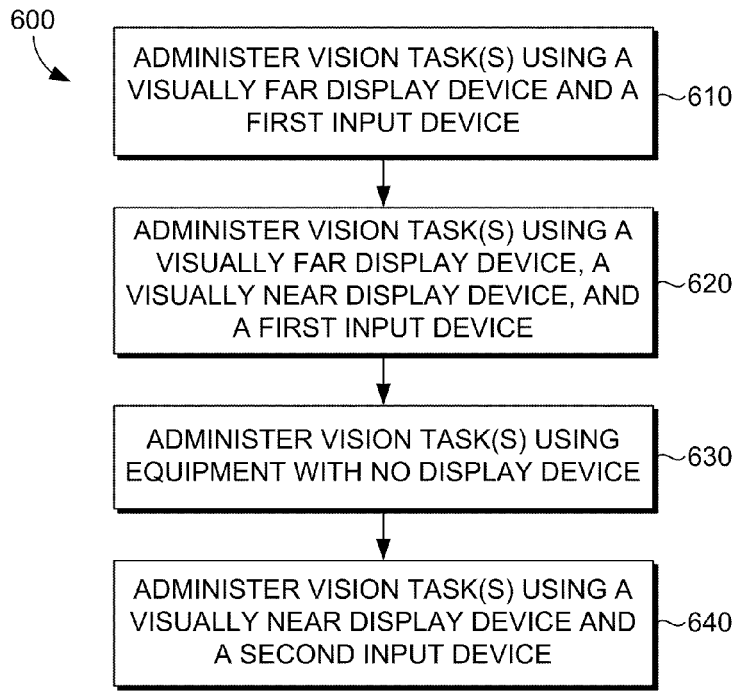
FIG. 6 illustrates a further method for unified vision testing and/or training in accordance with the present invention.

Referring now to FIG. 6, a further method 600 of administering vision testing and/or training in accordance with the present invention is illustrated. In step 610, one or more vision testing and/or training task using a visually far display device and a first input device may be administered to an individual. In step 620, one or more vision testing and/or training task using a visually far display device, a visually near display device, and a first input device may be administered to the individual. Step 620 may, for example, involve administering a near-far focus test. In step 630, one or more vision testing and/or training task using equipment with no display device may be administered to the individual. In step 640, one or more vision testing and/or training task using a visually near display device and a second input device may be administered to the individual.

Figure 7:
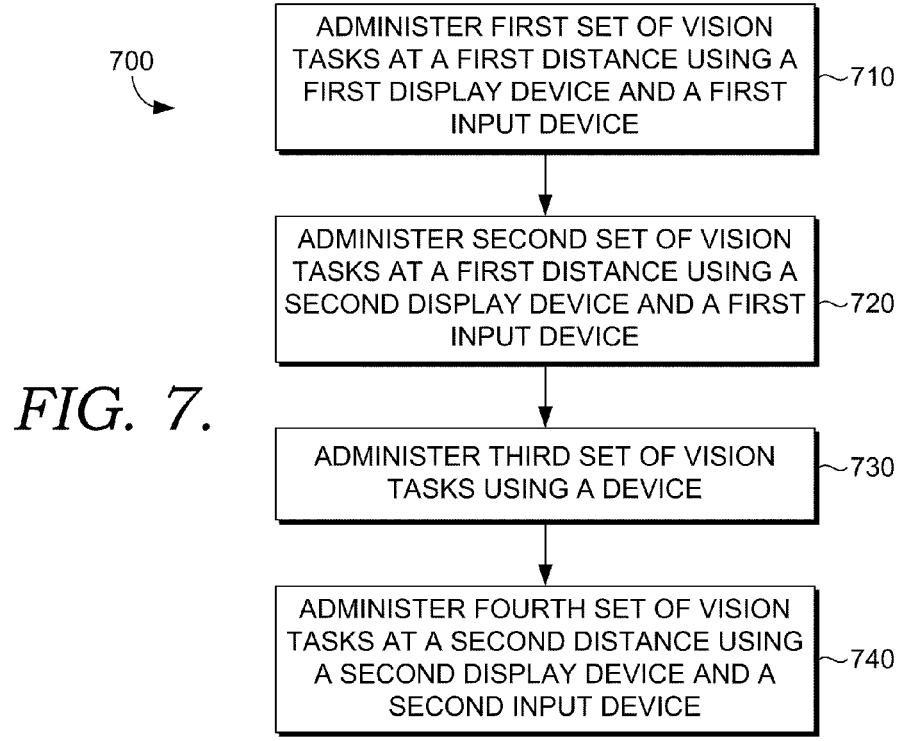
FIG. 7 illustrates a further method for unified vision testing and/or training in accordance with the present invention.

Referring now to FIG. 7, a further method 700 of administering vision testing and/or training in accordance with the present invention is illustrated. In step 710, a first set of vision testing and/or training tasks at a first distance using a first display device and a first input device may be administered to an individual. In step 720, a second set of vision testing and/or training tasks at the first distance using a second display device and the first input device may be administered to the individual. In step 730, a third set of vision testing and/or training tasks using a device may be administered to the individual. The device utilized in step 730 need not be a display device. In step 740, a fourth set of vision testing and/or training tasks at a second distance using the second display device and a second input device may be administered to the individual. Each of the first set of vision testing and/or training tasks, second set of vision testing and/or training tasks, third set of vision testing and/or training tasks, and fourth set of vision testing and/or training task may comprise one or more type of vision task administered one or more times.

Figure 8A:
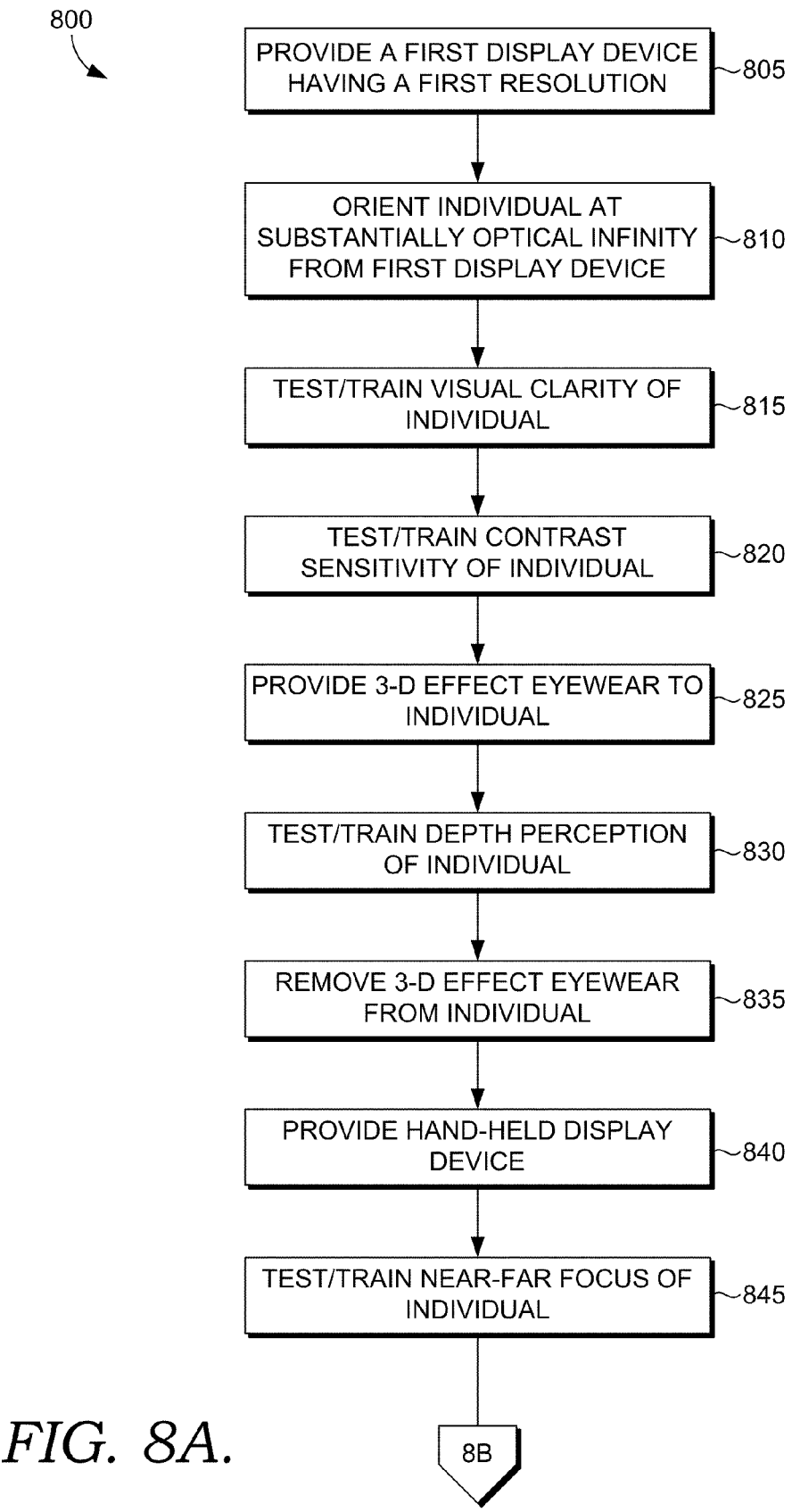
FIG. 8 illustrates a further method for unified vision testing and/or training in accordance with the present invention.
Figure 8B:
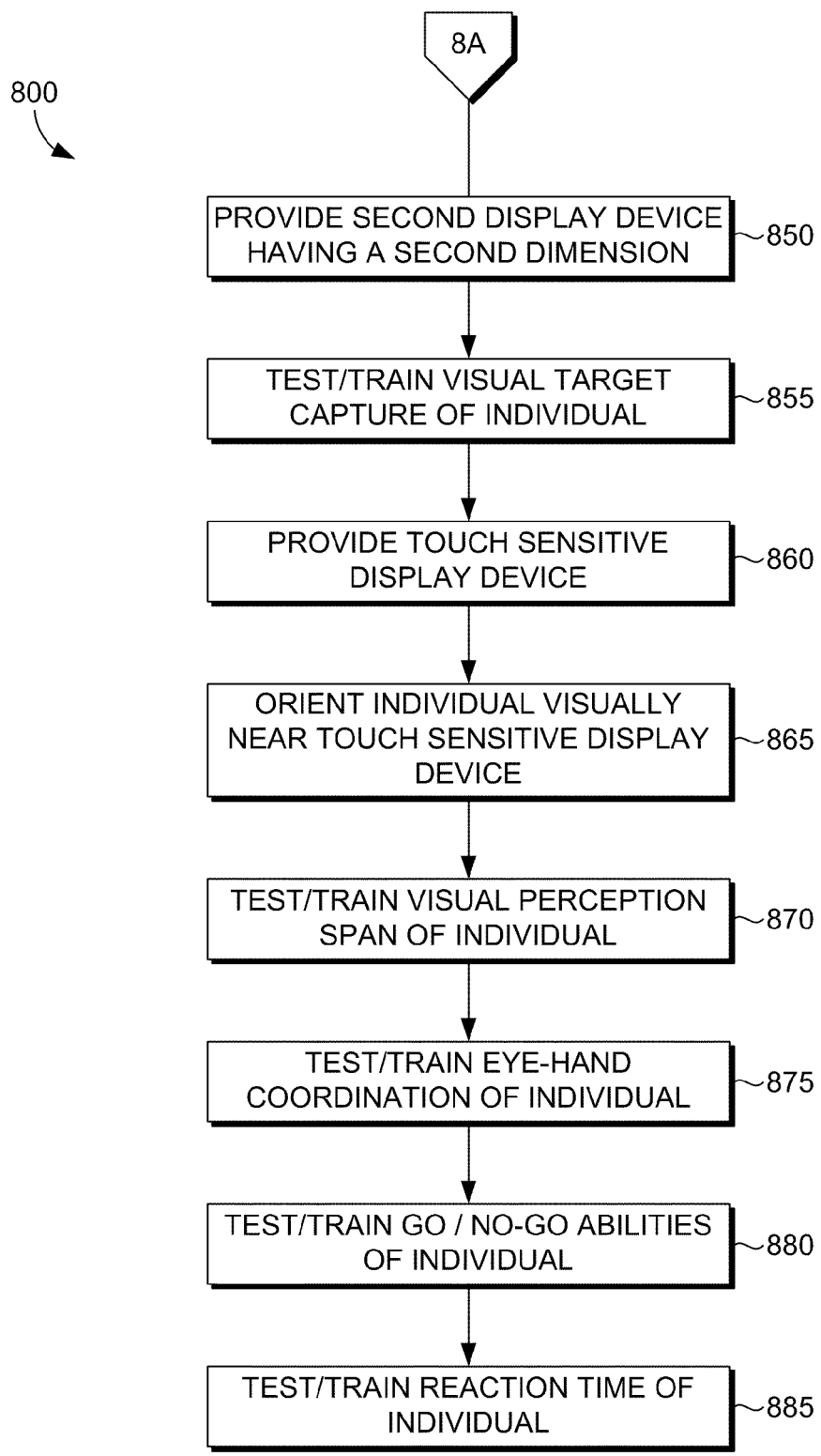

Referring now to FIG. 8A, a further method 800 of administering vision testing and/or training in accordance with the present invention is illustrated. In step 805, a first display device having a first resolution may be provided. In step 810, the individual to be tested may be oriented at substantially optical infinity from the first display device. In step 815, the visual clarity of the individual may be tested and/or trained. In step 820, the contrast sensitivity of the individual may be tested and/or trained. Step 815 and step 820 may utilize the first display device to display visual testing indicia. The individual may respond to visual testing indicia displayed in step 810, step 815, and/or step 820 using an input device, such as a multi-touch device. In step 825, three-dimensional effect eyewear may be provided to the individual. The three-dimensional effect eyewear provided in step 825 may comprise anaglyphic eyewear, LCD shutter eyewear, vectographic (polarized), or other eyewear utilized to provide a three dimensional image to an individual in conjunction with a display device. In step 830, the depth perception of the individual may be tested and/or trained. Step 830 may utilize the first display device to display visual indicia for view by the individual through the three-dimensional eyewear. The individual may respond to visual indicia displayed in step 830 using an input device, such as a multi-touch device. In step 835, the three-dimensional effect eyewear may be removed from the individual. In step 840 a handheld display device may be provided to the individual. The handheld display device provided in step 840 may comprise a multi-touch device, such as may also be used as an input device in method 800. In step 845 the near-far focus of the individual may be tested and/or trained utilizing the first display device, the handheld display device, and an input device. Continuing on to FIG. 8B that is a continuation of method 800, in step 850 a second display device having a second dimension may be provided. In step 855, the visual target capture ability of the individual may be tested and/or trained. Step 855 may utilize the second display device to display visual indicia. The individual may respond to visual indicia displayed in step 855 using an input device, such as a multi-touch device. In step 860, a touch sensitive display device may be provided to the individual. In step 865 the individual may be oriented visually near the touch sensitive display device. In step 870, the visual perception span of the individual may be tested and/or trained. In step 875, the eye-hand coordination of the individual may be tested and/or trained. In step 880, the go/no-go abilities of the individual may be tested and/or trained. Step 870, step 880, and step 890 may utilize one or a plurality of visual indicia displayed on the touch sensitive display device. The individual may respond to visual indicia displayed by touching the touch sensitive display. In step 885 the reaction time of the individual may be tested and/or trained. Step 885 may utilize visual indicia displayed on the touch sensitive display device. The individual may respond to the visual indicia displayed in step 885 by changing his/her contact with the touch sensitive display device.

Figure 9:
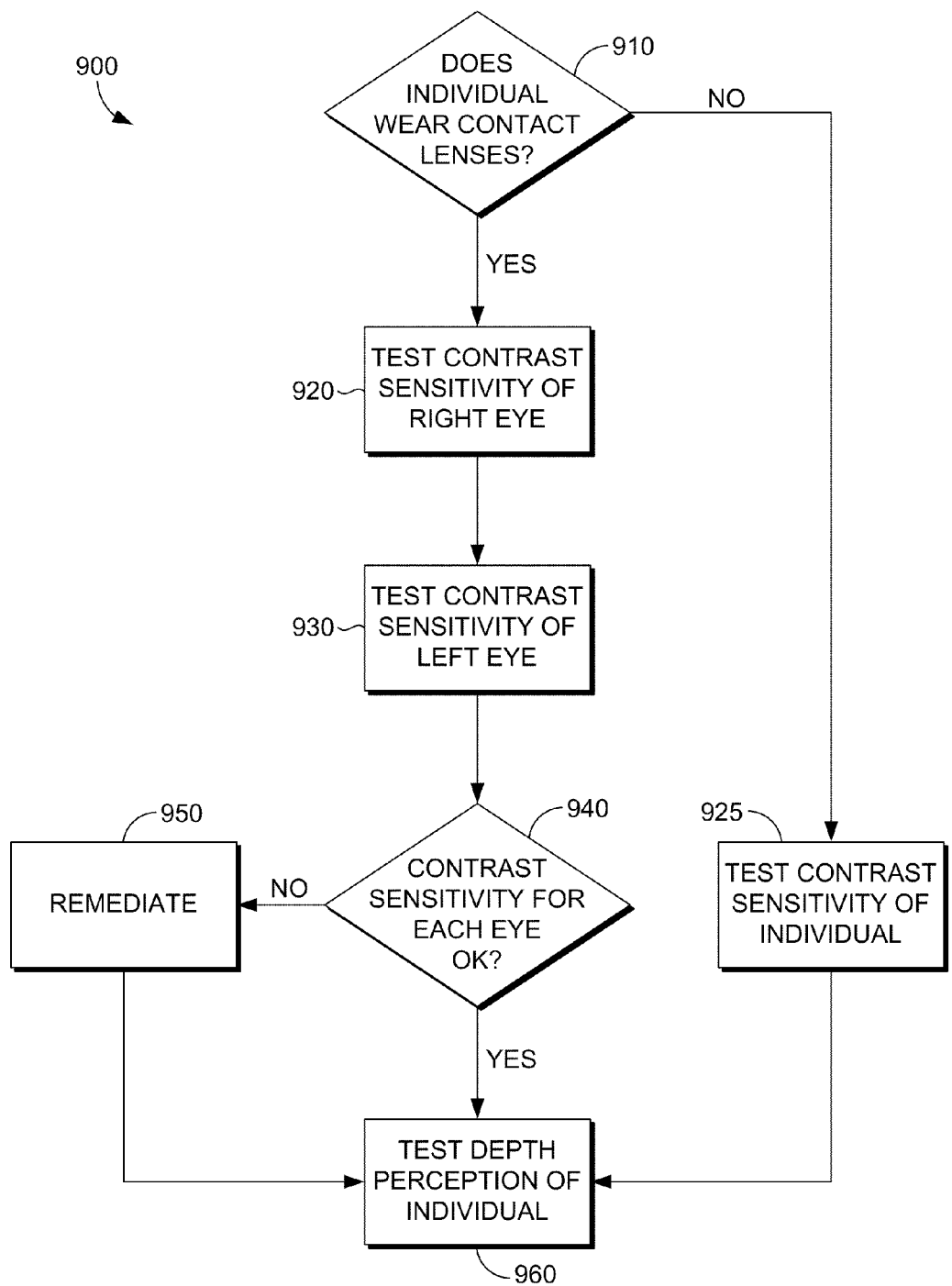
FIG. 9 illustrates inter-related methods for testing and/or training contrast sensitivity and depth perception of an individual in accordance with the present invention.

Referring now to FIG. 9, a method 900 for the interrelated testing and/or training of contrast sensitivity and depth perception of an individual is illustrated. In step 910, it is determined whether the individual to be tested and/or trained wears contact lenses. If the individual to be tested and/or trained does wear contact lenses, method 900 proceeds to step 920. In step 920, the contrast sensitivity of the right eye of the individual is tested and/or trained. Method 900 then proceeds to step 930, wherein the contrast sensitivity of the left eye of the individual is tested and/or trained. Method 900 then proceeds to step 940. In step 940, it is determined whether the contrast sensitivity for both the right eye and the left eye of the individual were acceptable. If the conclusion of step 940 is that the results of either or both of step 920 and step 930 indicated that one or both eyes of the individual lacked sufficient contrast sensitivity, method 900 proceeds to step 950 of remediating that contrast sensitivity deficiency. In an exemplary embodiment, remediating contrast sensitivity is an immediate action. For example, corrective actions may be administered during or coincidentally to testing and/or training of the subject in an attempt remediate the insufficient contrast sensitivity. In an additional exemplary embodiment, remediating the contrast sensitivity may include a delayed remediation that minimally or insignificantly delays the testing and/or training. For example, a delayed remediation may include scheduling, in the future, corrective steps that may remediate the insufficient contrast sensitivity. Often such a deficiency in contrast sensitivity may relate to build up of deposits upon a contact lens, and more frequent changing and/or cleaning of contact lenses may be implemented to remediate the contrast sensitivity deficiency. If the conclusion of step 940 is that the contrast sensitivity for each eye is acceptable, method 900 may proceed to test the depth perception or other sensory tasks of the individual in step 960. If the remediation of step 950 is successful, which may be determined by repeating step 920, step 930 and step 940, method 900 may also proceed to step 960. Alternatively, remediation step 950 may occur subsequent to the completion of method 900, and after determining in step 940 that contrast sensitivity for each eye of the individual is not acceptable, method 900 may proceed to step 960 nevertheless. If the conclusion of step 910 is that the individual does not wear contact lenses, method 900 may proceed to step 925 of testing and/or training the contrast sensitivity of the individual for both eyes simultaneously. After step 925, method 900 may proceed to step 960 of testing and or training the depth perception of the individual. Step 960 will necessarily require the use of both eyes simultaneously by the individual. The depth perception of an individual may be adversely impacted by differences in the visual clarity and/or contrast sensitivity of the individual's left eye and right eye. Method 900 may be utilized to identify deficiencies and or differences in the visual abilities of an individual's left eye and right eye, such as may commonly arise in contact lens wearers, which may otherwise negatively impact the depth perception of the individual.

Figure 10B:
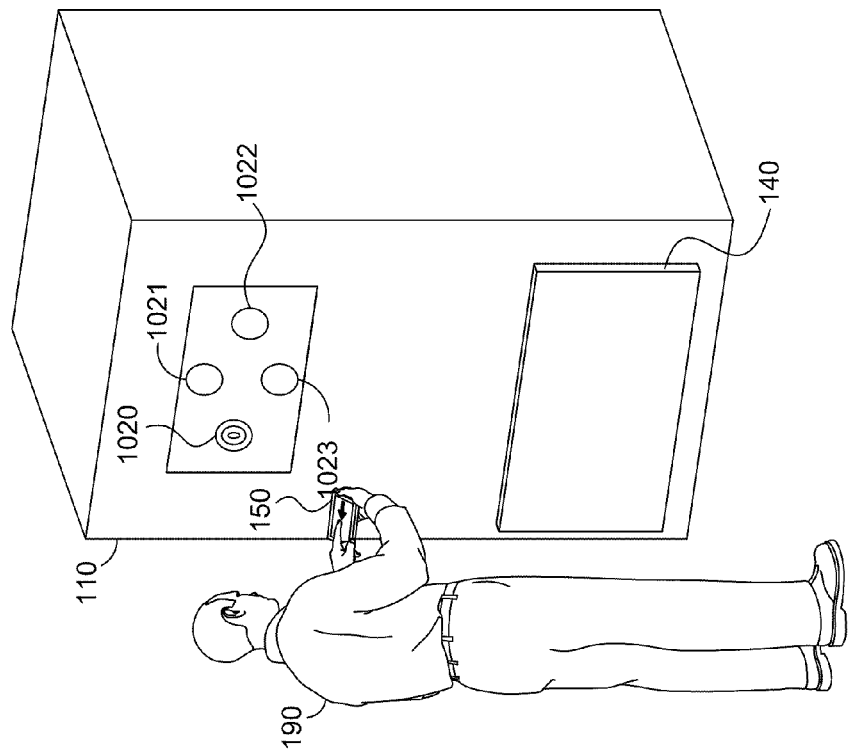
FIG. 10B illustrates contrast sensitivity testing and/or training in accordance with the present invention.
Figure 10A:
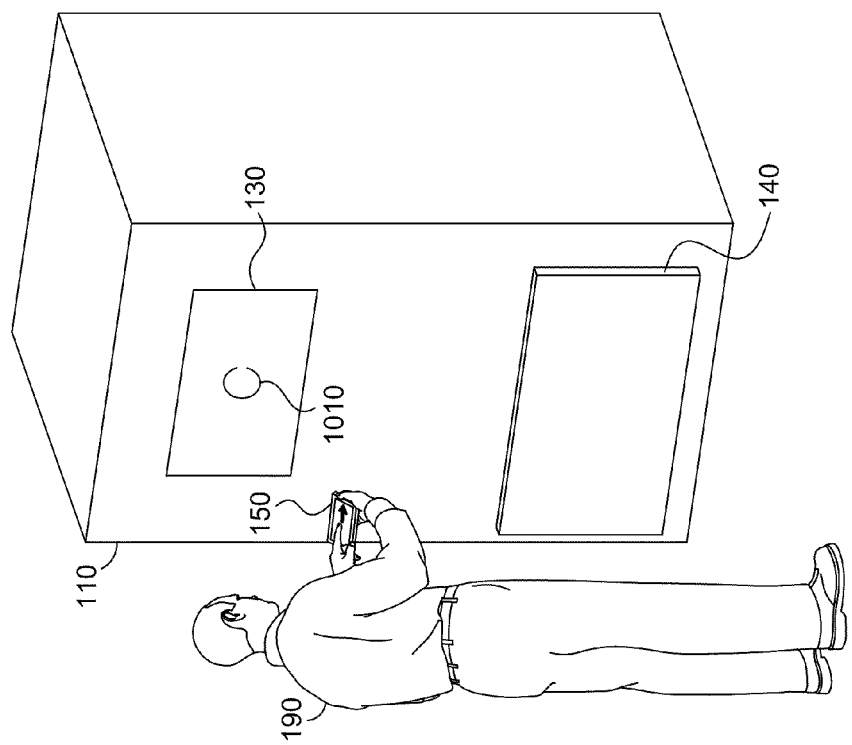
FIG. 10A illustrates visual clarity testing and/or training in accordance with the present invention.

Referring now to FIG. 10A, an example of a testing and/or training system in use for testing the static visual clarity of an individual 190 is illustrated. The testing and/or training system may comprise a kiosk 110 with a first display device 130 capable of displaying a visual indicia 1010. Individual 190 may utilize a first input device 150 to register an input in response to displayed visual indicia 1010. Examples of possible static visual clarity testing and/or training tasks that may be implemented in conjunction with kiosk 110 are described further below.

Referring now to FIG. 10B, an example of a visual testing and/or training kiosk 110 is illustrated while testing the contrast sensitivity of an individual 190. First display device 130 may display a first visual indicia 1020, a second visual indicia 1021, a third visual indicia 1022, and a fourth visual indicia 1023. In the example illustrated in FIG. 10B, first visual indicia 1020 possesses a higher contrast than the other visual indicia displayed on first display device 130. Accordingly, individual 190 may register an input selecting first visual indicia 1020 using an input device 150, such as a multi-touch device. Examples of possible contrast sensitivity testing and/or training may be implemented with kiosk 110 are described further below.

Figure 10C:
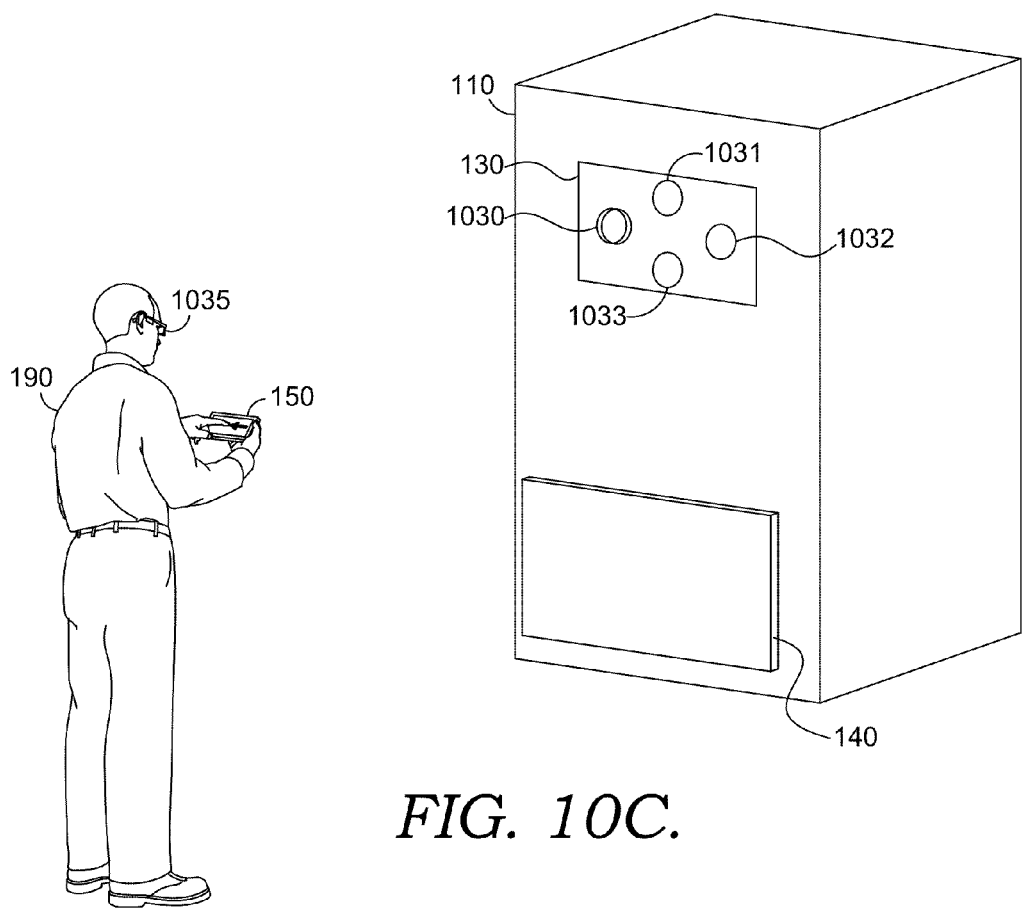
FIG. 10C illustrates depth perception testing and/or training in accordance with the present invention.

Referring now to FIG. 10C, an example of a visual testing and/or training kiosk 110 in use for testing and/or training the depth perception of an individual 190 is illustrated. First display device 130 may display a first visual indicia 1030, a second visual indicia, a third visual indicia 1032, and a fourth visual indicia 1033. As illustrated in the example of FIG. 10C, subject 190 has been provided with three-dimensional effect eyewear 1035. Three dimensional effect eyewear 1035 may, for example, comprise anaglyphic glasses that provide lenses of different colors that coincide with images displayed on first display device 130 for the left and right eyes of the individual 190. By way of further example, three dimensional effect eyewear 1035 may comprise LCD shutter glasses that alternatively allow light to pass to the individual 190 left eye and right eye in synchronization with first display device 130. In such a fashion, the left eye of individual 190 and the right eye of individual 190 may perceive a slightly different positioned visual indicia, such as first visual testing indicia 1030 in the example illustrated in FIG. 10C. Examples of possible depth perception testing and/or training tasks that may be implemented in conjunction with kiosk 110 are described further below.

Figure 10D:
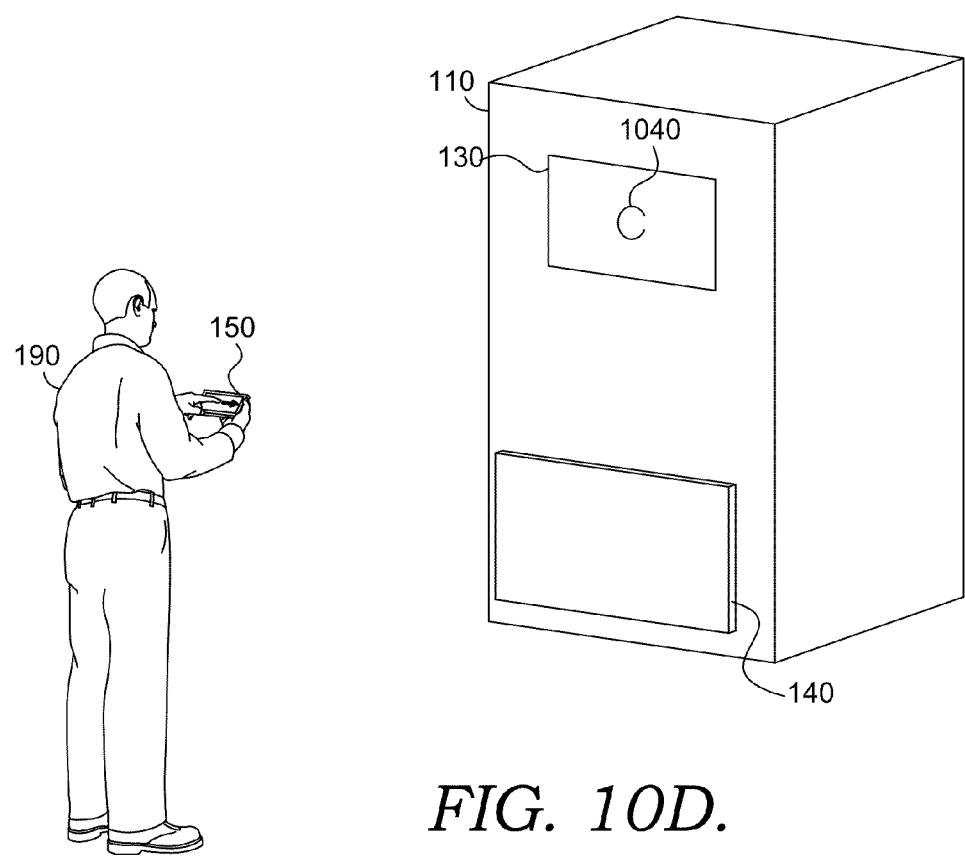
FIG. 10D illustrates portion of near-far focus testing and/or training in accordance with the present invention.
Figure 10E:
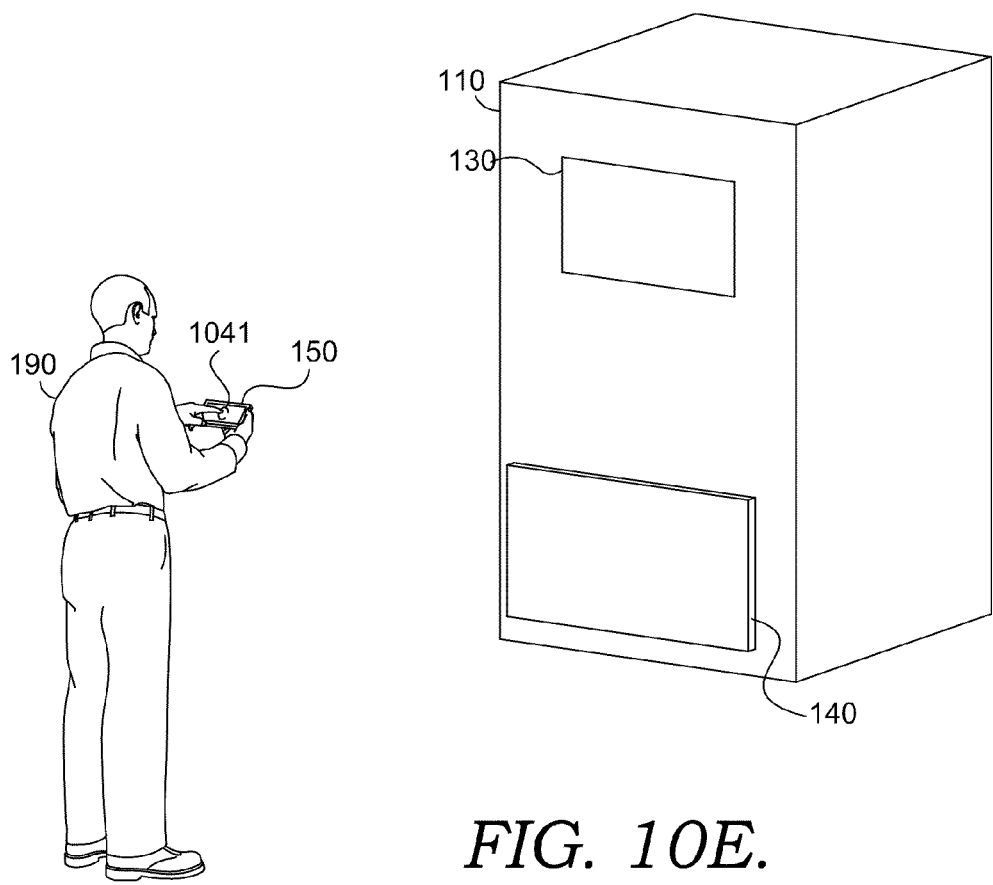
FIG. 10E illustrates a further portion of near-far focus testing and/or training in accordance with the present invention.

Referring now to FIG. 10D and FIG. 10E, an example of a visual testing and/or training kiosk 110 in use for near-far focus testing and/or training is illustrated. In FIG. 10D a first visual indicia 1040 may be displayed on first display device 130, which is visually far from subject 190. Subject 190 may enter a response using first input device 150 based upon a trait possessed by visual indicia 1040. In FIG. 10E, a second visual indicia 1041 may be displayed on first input device 150, which also comprises a handheld display device in this example, and further in this particular example comprises a multi-touch device. Individual 190 may register an input in response to visual indicia 1041 using first input device 150. In near-far focus testing and/or training using kiosk 110, first display device 130, and multi-touch device 150, both the accuracy of the inputs registered by individual 190 and the speed of those inputs may be measured and recorded by control unit 120. Examples of possible near-far focus testing and/or training tasks that may be implemented in conjunction with kiosk 110 are described further below.

Figure 10F:
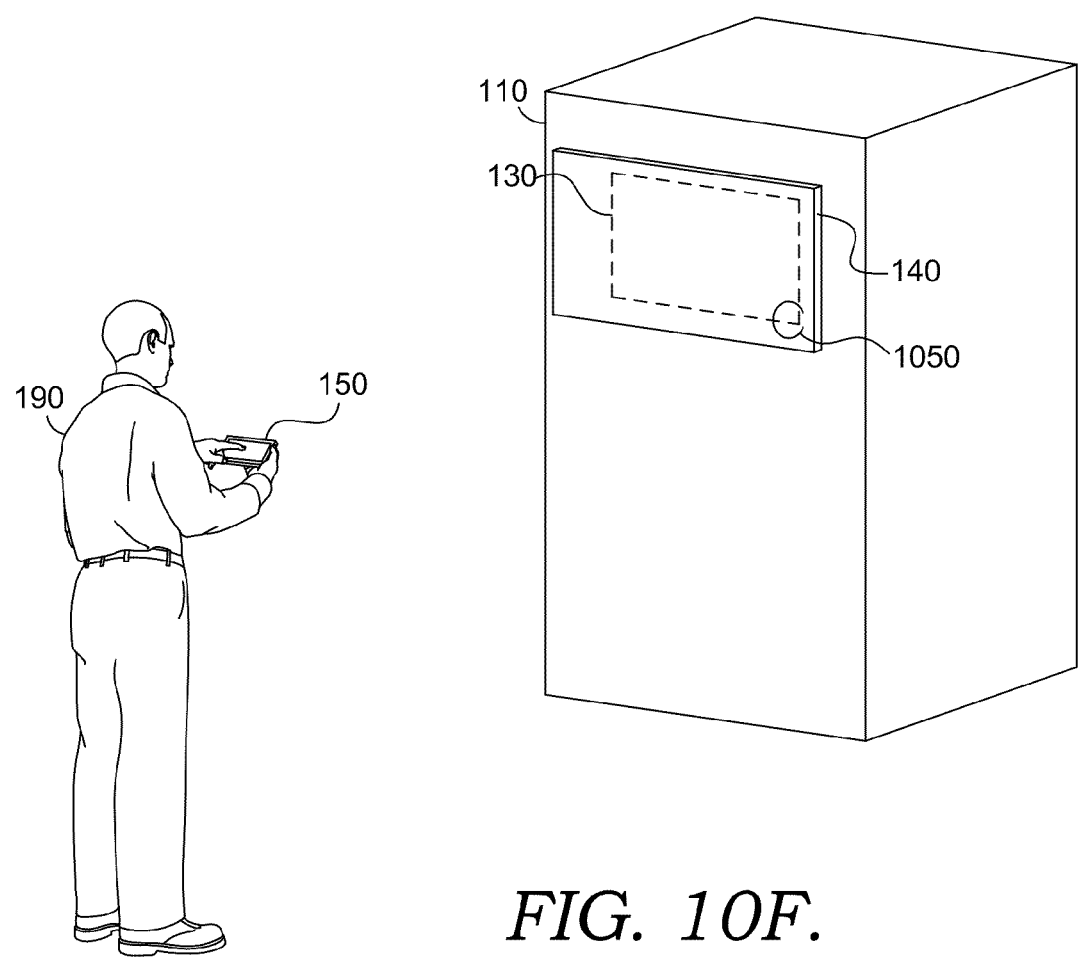
FIG. 10F illustrates saccadic target capture testing and/or training in accordance with the present invention.

Referring now to FIG. 10F, an example of a vision testing and/or training kiosk 110 in use for testing and/or training the saccadic target capture skills of an individual 190 is illustrated. As illustrated in the example of FIG. 10F, second display device 140 has been raised to occlude first display device 130 from the view of individual 190. As illustrated in the example of FIG. 10F, a visual indicia 1050 may occur at a position on second display device 140 unexpected by individual 190, requiring a quick and accurate saccadic eye movement and recognition by individual 190 to perceive the trait(s) possessed by visual indicia 1050. Individual 190 may register an input in response to visual indicia 1050 using first input device 150. Examples of possible saccadic capture testing and/or training tasks that may be implemented in conjunction with kiosk 110 are described further below.

Figure 10H:
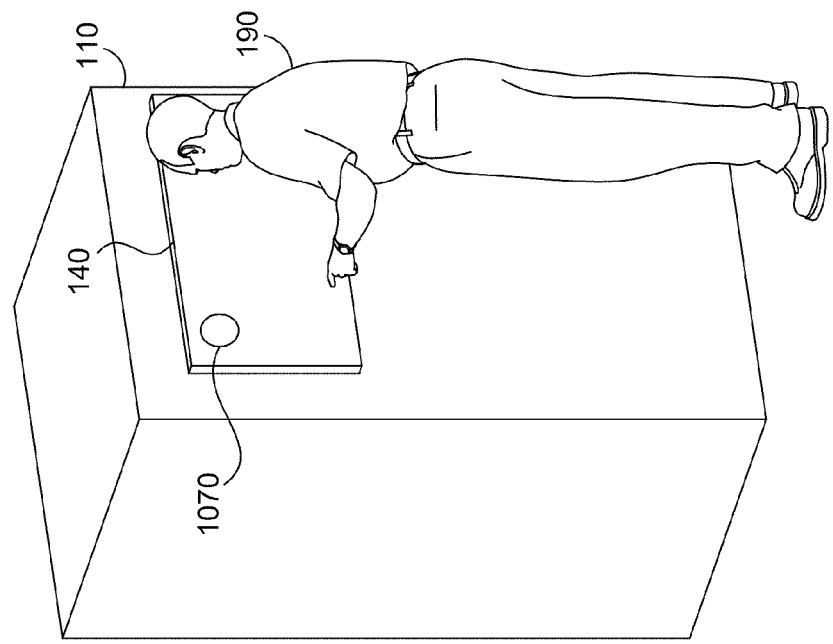
FIG. 10H illustrates eye-hand coordination testing and/or training in accordance with the present invention.
Figure 10G:
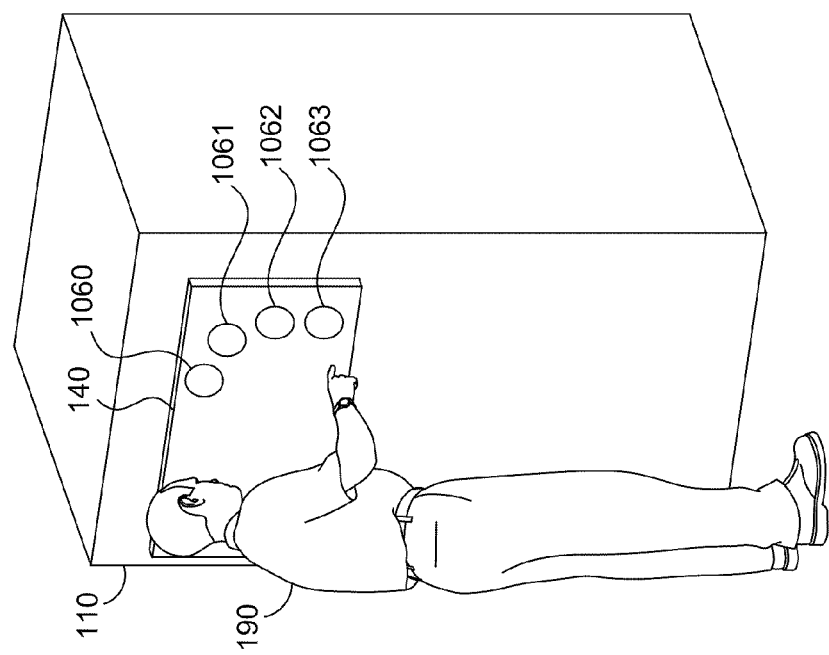
FIG. 10G illustrates visual perception span testing and/or training in accordance with the present invention.

Referring now to FIG. 10G, an example of a vision testing and/or training kiosk 110 in use for testing and/or training the visual perception span and/or speed of an individual 190 is illustrated. Individual 190 may be positioned visually near to second display device 140. Second display device 140 may display visual testing indicia possessing visual information perceivable by individual 190. In the example illustrated in FIG. 10G, the visual information may be the spatial distribution of the visual indicia. In the example of FIG. 10G, second display device 140 comprises a touch sensitive display device and individual 190 may respond to the display of the visual indicia on the second display device 140 by touching the second display device 140 at the location of the visual indicia after the display of the visual indicia have been terminated. In the example illustrated in FIG. 10G, a first visual indicia 1060, a second visual indicia 1061, a third visual indicia 1062, and a fourth visual indicia 1063 are illustrated. In visual perception span and/or speed testing and/or training in accordance with the present invention larger numbers of visual indicia may be utilized, particularly for individuals who demonstrate large visual perception span abilities. Examples of possible visual perception span and/or speed testing and/or training tasks that may be implemented in conjunction with kiosk 110 are described further below.

Referring now to FIG. 10H, an example of vision testing and/or training kiosk 110 in use for testing and/or training the eye-hand coordination of an individual 190 is illustrated. Second display device 140 may display visual indicia, such as visual indicia 1070, that individual 190 may attempt to contact with the hands of individual 190. Examples of possible visual eye-hand coordination testing and/or training tasks that may be implemented in conjunction with kiosk 110 are described further below.

Figure 10J:
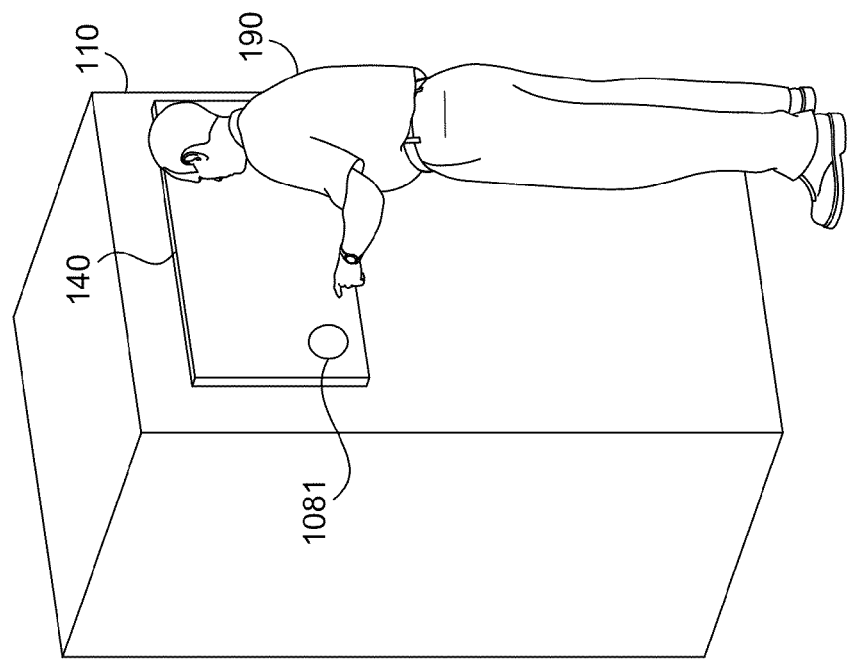
FIG. 10J illustrates a further portion of go/no-go testing and/or training in accordance with the present invention.
Figure 10I:
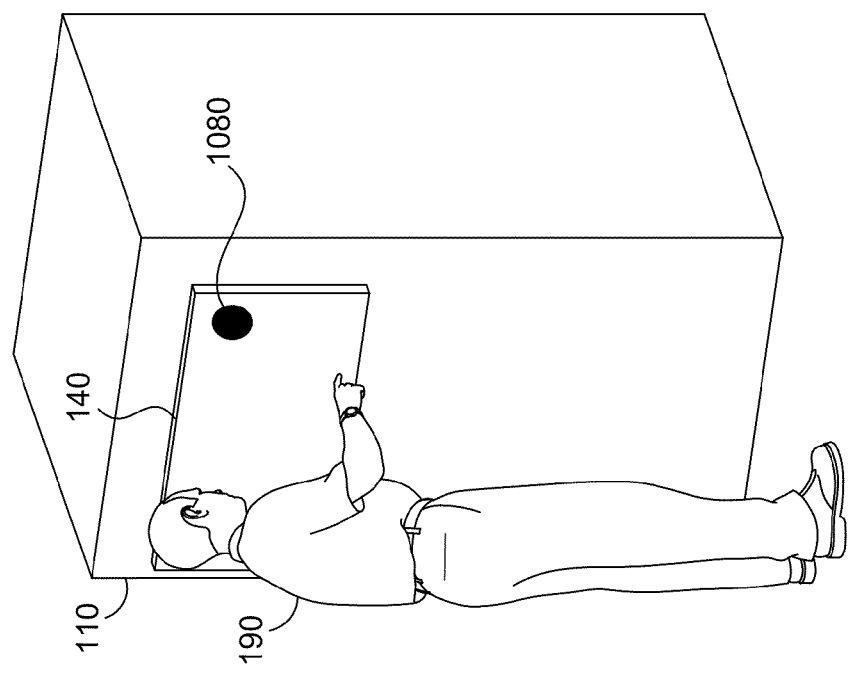
FIG. 10I illustrates a portion of a go/no-go testing and/or training in accordance with the present invention.

Referring now to FIGS. 10I and 10J, an example of a vision testing and/or training kiosk 110 in use for testing and/or training go/no-go abilities is illustrated. As illustrated in FIG. 10I, a visual indicia 1080 having a first property, such as being a solid circle, is displayed on second display device 140. Individual 190 may be instructed not to contact visual indicia processing the first property, such as being a solid circle. In the example illustrated in FIG. 10J, a second visual indicia 1081 possessing a second property, such as being an empty circle, is displayed on second display device 140. Individual 190 may be instructed to contact visual indicia possessing the second property, such as being an empty circle. Examples of possible go/no-go testing and/or training tasks that may be implemented in conjunction with kiosk 110 are described further below.

Figure 10L:
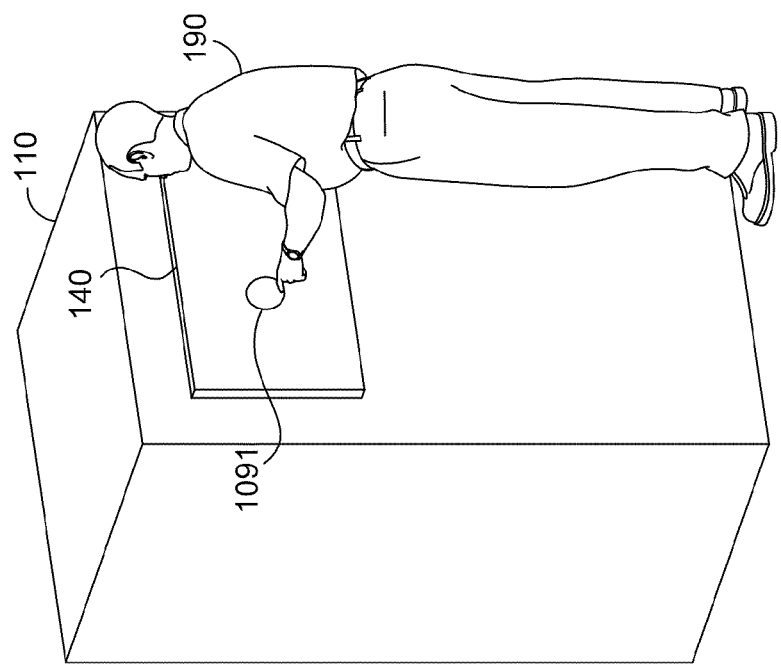
FIG. 10L illustrates a further portion of reaction time testing and/or training in accordance with the present invention.
Figure 10K:
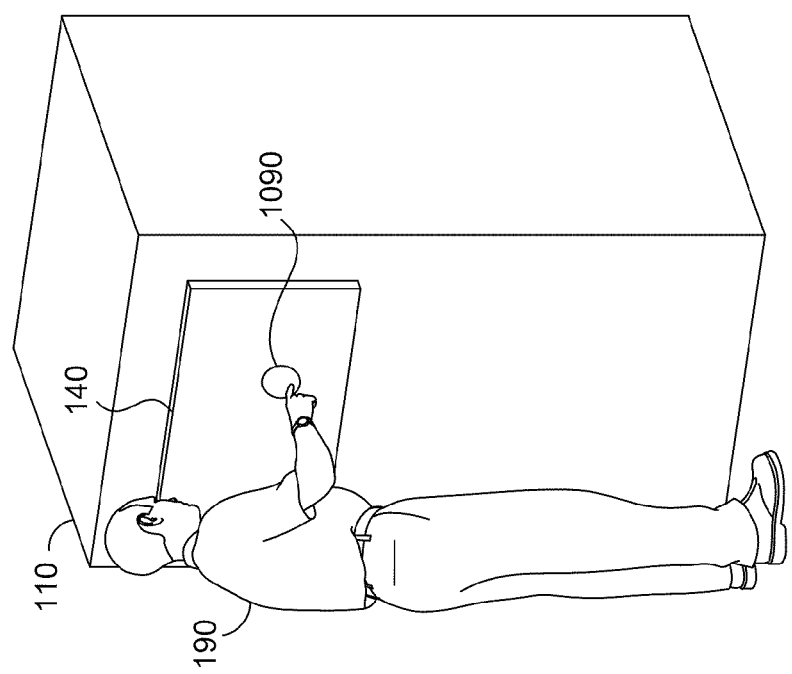
FIG. 10K illustrates a portion of reaction time testing and/or training in accordance with the present invention.

Referring now to FIG. 10K and FIG. 10L, an example of a vision testing and/or training kiosk 110 in use for testing and/or training the reaction time of an individual 190 is illustrated. Individual 190 may initially contact visual indicia 1090 with a hand. FIG. 10L illustrates a subsequent point in time at which visual indicia 1090 has ceased to be displayed and has been replaced with second visual indicia 1091. Individual 190 may attempt to move his or her hand to contact the newly displayed second visual indicia 1091. The time and or accuracy of the attempt by individual 190 to contact visual indicia 1091 may be measured and recorded using control unit 120. Examples of possible reaction time testing and/or training tasks that may be implemented in conjunction with kiosk 110 are described further below.

Figure 11:
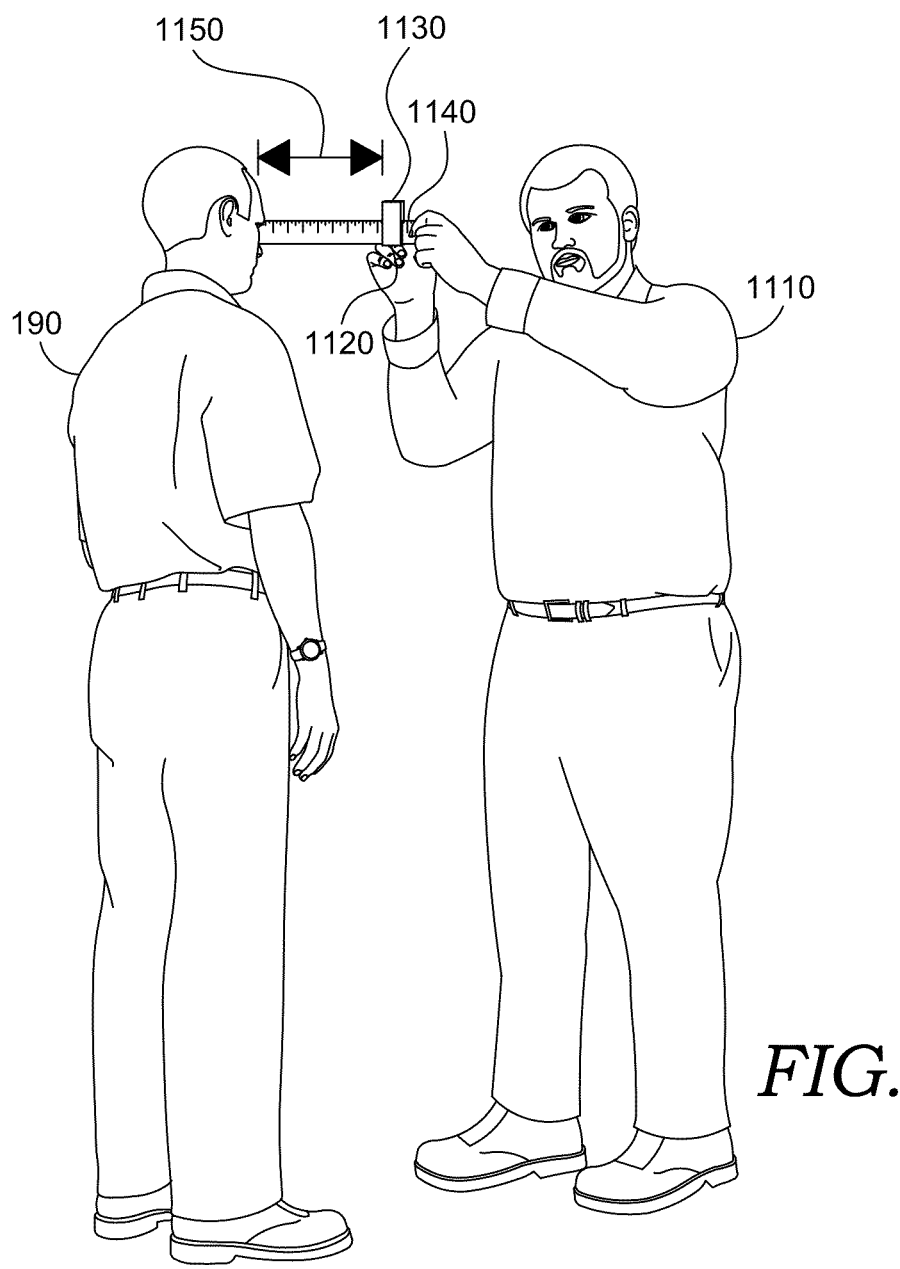
FIG. 11 illustrates near-point of convergence testing and/or training in accordance with the present invention.

Referring now to FIG. 11, an example of near-point of convergence testing and/or training of an individual using vision testing equipment 1120 in accordance with the present invention is illustrated. Near-point of convergence testing and/or training may also be referred to as visual endurance testing and/or training. Individual 190 whose visual skills are being tested and/or trained by trainer 1110 is illustrated. Trainer 1110 may use device 1120 to measure the near point of convergence of individual 190. Device 1120 may utilize measuring component 1140 and marker component 1130. Marker component 1130 may be slid along measuring component 1140 until individual 190 can no longer visually resolve a single image of marker component 1130. At this position, a distance 1150 may be determined. This distance 1150 provides a measure of the near point of convergence for individual 190. Data from testing and/or training using vision equipment, such as equipment 1120, may be entered by trainer 1110 into kiosk 110 using an input device such as a touch sensitive screen, which second display device 140 may comprise. Other types of testing and/or training data, instead of or in addition to near-point of convergence testing and/or training, may be similarly entered using kiosk 110.

Embodiments of the present invention contemplate completing two or more exercises in a predefined order. The order in which the exercises are presented to a subject may be structured so that skills tested earlier in the process are those skills that, when improved or corrected, have an impact on following skills. For example, results from a static visual acuity test may indicate that other skills may be severely impaired by a subject's poor visual acuity. Therefore, a waterfall type logic may be employed so that the order in which skills are tested or trained may be in an efficient manner.

In an exemplary embodiment, assessments may be conducted in the following order: static visual clarity, contrast sensitivity, depth perception, near-far quickness, target capture, near point of convergence (visual endurance), perception span, eye-hand coordination, go/no go, and reaction time. As the above order is merely exemplary, it is understood that any order may be implemented to achieve various efficiencies or advantages. For example, to reduce physical configuration changes (e.g., movement of displays, inputs, or subjects) to a unified vision testing system, the order may be altered, which could result in a shorter total assessment time. Or, alternatively, the assessments may be presented to a subject in a manner to prevent fatigue (e.g., muscle fatigue, eye fatigue, mental fatigue). Similarly, the assessments may be arranged in such a manner as to provide the greatest likely benefit in the shortest length of time or with the fewest number of assessments. Additionally, it is contemplated that the order in which assessments are presented is based on a particular sport or activity associated with a current subject. Similarly, the order of assessments may also be influenced by a tier system to which the subject belongs (e.g., amateur, professional, commercial). For example, additional assessments may be provided to one or more of the tiers based on the level of granularity desired to achieve for a subject within that tier. Therefore, at a professional level, the order of assessments may be optimized to result in fine-grained metrics, while the order of assessments at an amateur level may be optimized to minimize time required to complete.

As previously discussed, a number of testing and/or training activities may be implemented individually or in combination with a unified vision testing system as described herein. While a number of the activities have been discussed hereinabove, additional details are provided hereinafter as to one or more exemplary embodiments of one or more activities. However, it is understood that the following are exemplary embodiments and not necessarily limiting as to the scope of the present invention.

Static Visual Clarity Testing and/or Training

In accordance with the present invention, an adaptable indicia may be used to test and/or train visual sensitivity abilities such as static visual acuity. For example, an indicia may be presented to a subject on a display device at an initial size that is visually unable to be correctly perceived by the subject. The indicia may then increase in size until the subject correctly perceives the indicia. By presenting a series of indicia and receiving responses from the subject when those indicia may be correctly perceived, an accurate assessment of the static visual acuity of a subject may be made as part of vision testing and/or training.

Visual indicia presented to a subject may possess visual traits. For example, a presented visual indicia maybe be a Landolt C possessing an orientation of left, right, up or down. When a subject perceives the orientation of a presented Landolt C, the subject may create an input to a testing system. For example, the subject may push a joystick in a direction corresponding to the orientation of a Landolt C presented as a visual indicia. By way of further example, a subject may use a multi-touch device to "stroke" the touch-sensitive screen in a direction corresponding to the orientation of a presented Landolt C. By correlating the size of the Landolt C at the time the subject correctly input the perceived orientation of the Landolt C, the visual acuity of the subject may be measured as part of vision testing and/or training.

The present invention may use indicia with changing, or adaptable, characteristics to assess the visual sensitivity of a subject. The characteristics possessed by an indicia when an individual can correctly perceive the indicia may provide an indication of the visual sensitivity of the individual. Examples of the types of adaptable characteristics that an indicia may possess in accordance with the present invention are, for example, the size and speed of an indicia. Further examples of changing characteristics are an indicia may possess are different trajectories of movement, color, contrast with a background, duration of display, or any other characteristic that is subject to modification in testing and/or training. In general, systems and methods in accordance with the present invention may use a display device to present indicia that possess varying characteristics, with the characteristics of the indicia potentially varying during any given period of display, to be perceived by a subject. Upon receipt of an input from the subject indicating that the subject believes he or she has perceived the indicia, the input received from the subject may be examined to determine whether it corresponds to the correct input for a displayed indicia. For example, the subject may be provided with an input device capable of receiving any one of a plurality of inputs, with each possible input corresponding to a trait potentially possessed by a displayed indicia. A trait possessed by an indicia may be, for example, an orientation, an identity, etc. By determining whether the input received matches the trait of the indicia displayed, a system in accordance with the present invention may assess the accuracy of the subject's visual perception of the displayed indicia.

Figure 12A:
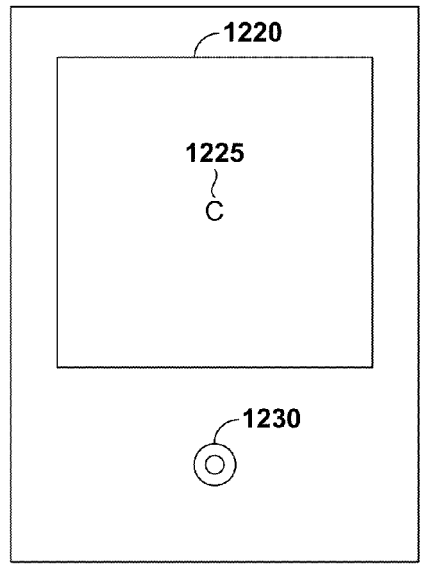
FIGS. 12A-12C illustrate the display of adaptable indicia in accordance with the present invention.
Figure 12B:
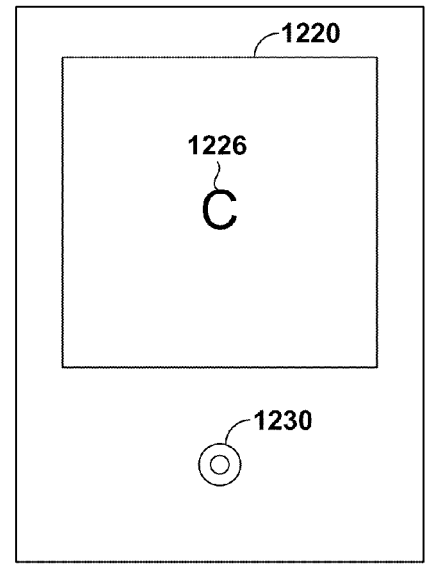
Figure 12C:
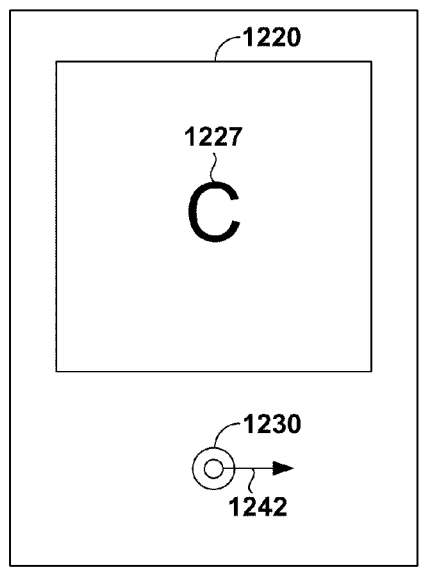

Referring now to FIGS. 12A-12C, an adaptable indicia 1225 at different times in its display on display device 1220 are illustrated. FIG. 12A illustrates indicia 1225 at a first time. At the time illustrated in FIG. 12A, indicia 1225 is displayed on display device 1225 at a size too small to be perceived by subject (not shown) and, therefore, no input is entered using joystick 1230. Indicia 1225 at a second time is illustrated in FIG. 12B. At the time illustrated in FIG. 12B, indicia 1226 remains at a size below that which may be perceived by subject (not shown), meaning that no input is registered on joystick 1230 at the time illustrated in FIG. 12B. At the time illustrated in FIG. 12C, indicia 1227 has increased in size so that subject (not shown) may perceive the visual trait possessed by indicia 1225. In the example illustrated in FIGS. 12A-12C, indicia 1225 comprises a Landolt C having an orientation to the right. Accordingly, when subject (not shown) perceives indicia 1225 as being oriented to the right joystick 1230 is depressed to the right as indicated by arrow 1242 in FIG. 12C. By subject (not shown) manipulating joystick 1230 to enter an input indicating the perceived orientation of indicia 1225 whenever indicia 1225 attains a size such that subject (not shown) may perceive indicia 1225, the visual acuity of subject (not shown) may be assessed as part of visual testing and/or training.

Referring now to FIGS. 13A-13D, a plurality of indicia possessing different visual traits are illustrated in conjunction with an input device 1330 capable of receiving a variety of inputs corresponding to the plurality of traits possessed by a displayed indicia. In the example illustrated in FIGS. 13A-13D the exemplary indicia illustrated are Landolt C's possessing the exemplary trait of one of four mutually exclusive orientations. Other types of indicia may be used in accordance with the present invention, and indicia may possess traits other than orientation. For example, indicia may be letters of the English alphabet that possess the trait of identity. Further, an indicia may possess a multitude of non-exclusive traits, such as identity and orientation. Of course, inputs corresponding to traits may be made in numerous fashions beyond the example of manipulating a joystick provided in FIGS. 13A-13D. For example, multi-touch devices, key boards, buttons, voice recognition, and the like may be used without departing from the present invention.

Figure 13A:
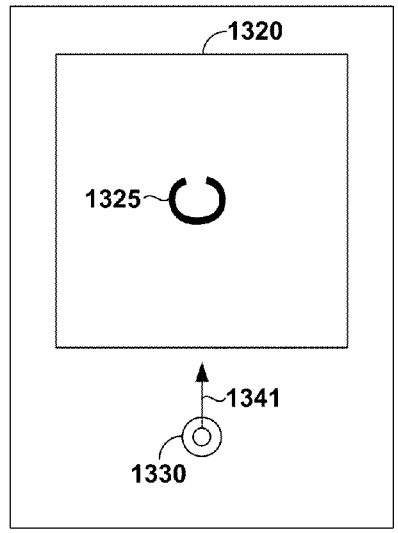
FIGS. 13A-13D illustrate the display of indicia in accordance with the present invention.

Referring now to FIG. 13A, a first indicia 1325 comprises a Landolt C having an upward orientation displayed by display device 1320. Joystick 1330 may be manipulated in a corresponding direction 1341 by subject (not shown) to indicate that subject (not shown) perceived first indicia 1325 and perceived the visual trait possessed by first indicia 1325.

Figure 13B:
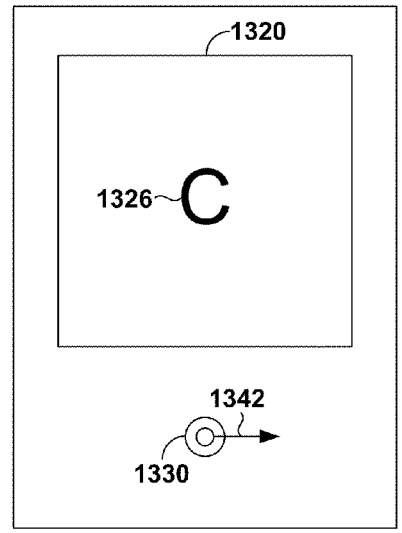

Referring now to FIG. 13B, a second indicia 1326 may comprise a Landolt C having an orientation to the right displayed by display device 1320. Joystick 1330 may be manipulated in a corresponding direction 1342 subject (not shown) perceived the second indicia 1326 and perceived the visual trait possessed by second indicia 1326.

Figure 13C:
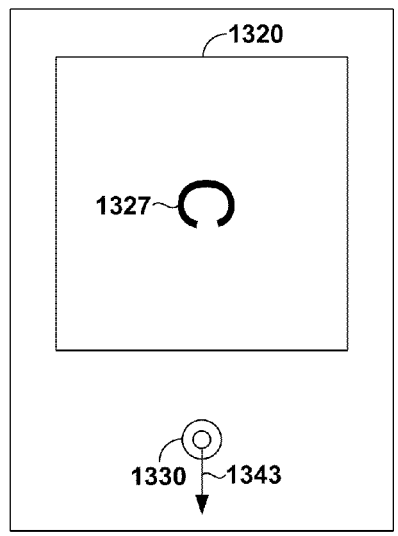

Referring now to FIG. 13C, a third indicia 1327 may comprise a Landolt C possessing a downward orientation displayed by display device 1320. Joystick 1330 may be manipulated in a downwards direction 1343 when subject (not shown) perceives the orientation of third indicia 1327.

Figure 13D:
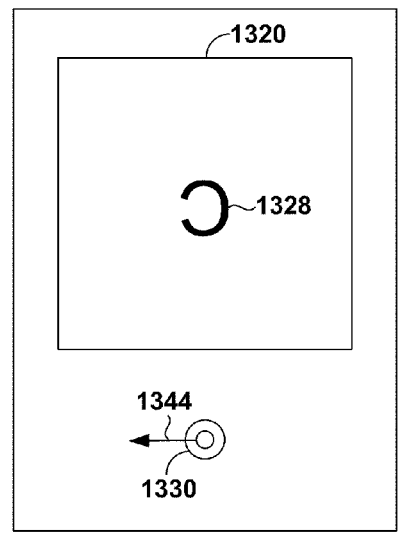

Referring now to FIG. 13D, a fourth indicia 1328 may comprise a Landolt C having a leftward orientation displayed by display device 1320. Joystick 1330 may be manipulated in a corresponding direction 1344 by subject (not shown) to indicate that subject (not shown) perceived fourth indicia 1328 and perceived the visual trait possessed by fourth indicia 1328.

Figure 14A:
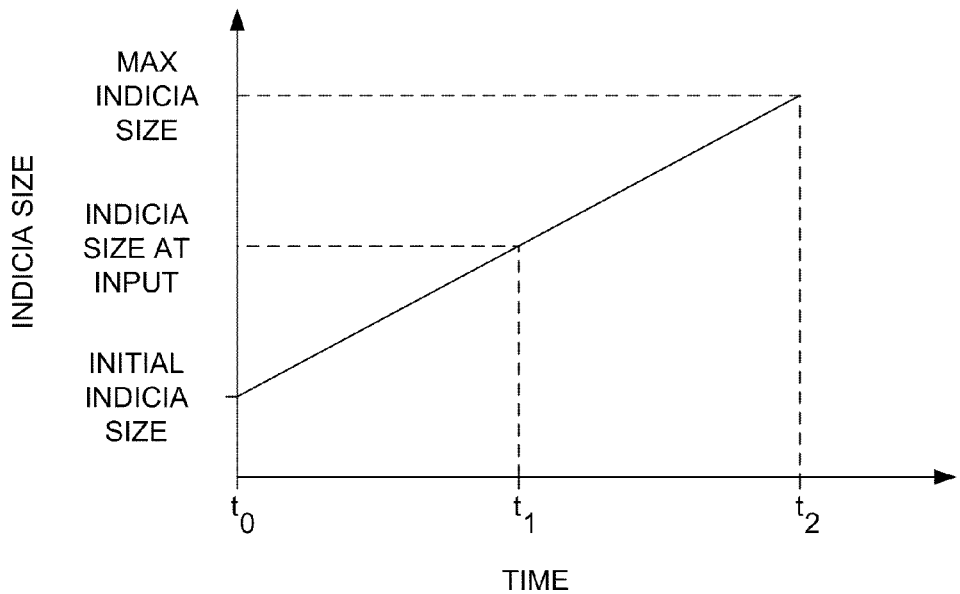
FIGS. 14A and 14B illustrate examples of the change in size of an adaptable indicia over time in accordance with the present invention.

Referring now to FIG. 14A, indicia size relative to time in an example of the changing indicia in accordance with the present invention is illustrated. In the example illustrated in FIG. 14A, the size of the indicia varies in a linear relationship with time. At a first time, "$t_1$", an indicia is displayed having an initial indicia size. The initial indicia size may be selected so as to be imperceptible to any individual to be tested. The indicia size may then grow at a substantially constant rate, such as the linear rate illustrated in FIG. 14A, until an input is received, for example, at time "$t_1$". At time "$t_1$" the indicia will possess a size. Both the time of input "$t_1$" and/or the size of indicia at input may be recorded and may be useful for assessing the visual acuity of an individual. At some point, such as, for example, time "$t_2$", an indicia will reach its maximum allowable size. The maximum allowable indicia size may be predetermined in the configuration of a visual sensitivity testing and/or training system. For example, there may be some point at which a given subject suffers from such serious deficiencies in visual acuity that no further increase in the size of a displayed indicia is warranted. Further, a given display device may limit or effectively limit the displayable size of an indicia. In either case, at some point an indicia may not be enlarged further, resulting in essentially a "timeout" scenario in a test methodology, which may result in the test being terminated, another indicia being displayed at an initial indicia size, an adjustment being made to the initial indicia size of a subsequently displayed indicia, or other measures being taken.

Figure 14B:
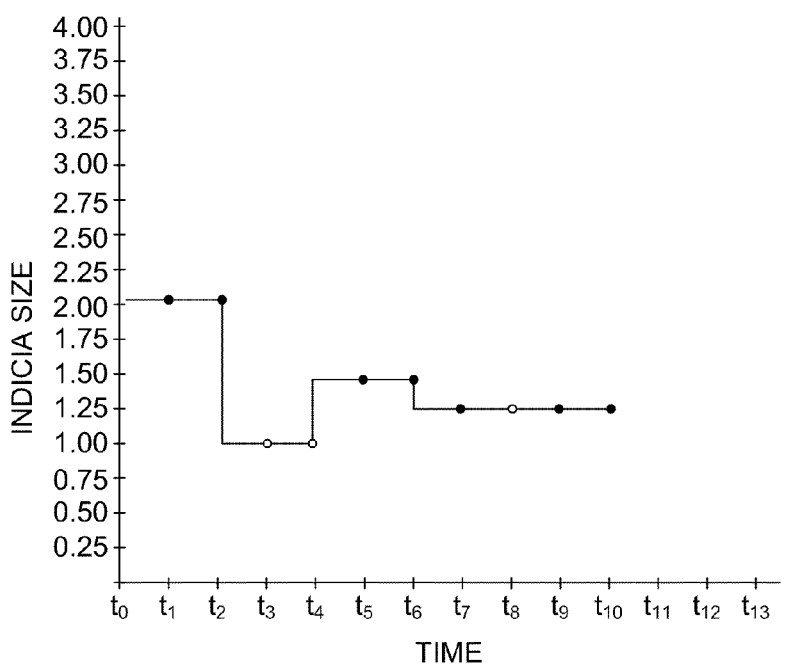

Referring now to FIG. 14B, indicia size relative to time in an example of the present invention that uses a step-wise indicia size adjustment is illustrated. In the example illustrated in FIG. 14B, an indicia may possess any of a plurality of specifically defined sizes, ranging in this example from a minimum of 0.25 to a maximum of 4.00 in increments of 0.25. A numerical description of the size of an indicia, such as the example illustrated in FIG. 14B, may refer to an absolute size (i.e., in inches, centimeters, etc.), an angular size in the field of view of a subject, or based on the number of pixels in size an indicia is on a display device. This size range is merely exemplary, however, and may be implemented using more or fewer discreet size levels. The possible indicia sizes may be selected based upon the distance a subject is to be positioned from a display device to provide an adequate range of visual sensitivity testing and/or training abilities. For example, there may be no need to assess or train the visual skills of an individual to better than a 0.25 level, so no indicia below that visual acuity level is necessary. Similarly, a particular embodiment of the present invention may not seek to test and/or train the visual acuity of a subject that is worse than 20/200. The specific size range of an indicia may be selected to provide adequate points of assessment between the minimum size needed and the maximum size needed. In the example illustrated in FIG. 14B, an indicia is initially displayed at time $t_0$ having a size of 2.00. The indicia will be displayed at that size for at least a predetermined period of time, during which subject (not shown) may respond. As indicated in FIG. 14B by the solid circle, that time $t_1$ the subject has provided a correct response. Thereafter, the indicia may be changed to possess a different trait while remaining at the same size. From time $t_1$ and time $t_2$ with indicia still at size 2.00, the subject has provided another correct response as is indicated by the solid circle. After two consecutive correct responses, the displayed indicia size may be decreased by an entire step to size 1.00 at time $t_2$. Thereafter, as indicated by the empty circle at time $t_3$, subject (not shown) may provide an incorrect response or fail to provide any response to the displayed indicia. At time $t_3$, the displayed indicia may be changed to possess a different trait while remaining at size 1.00. In the example illustrated in FIG. 14B, subject (not shown) has incorrectly responded or failed to respond to that displayed indicia by time $t_4$. Thereafter, the displayed indicia is increased in size by half a step to a size 1.50 at time $t_4$. As indicated by the solid circle, by time $t_5$, the subject has provided a correct response. Thereafter, the displayed indicia is changed to possess another trait and is again displayed still at size 1.50. As indicated by the solid circle, subject (not shown) has responded correctly at time $t_6$. Thereafter, the displayed indicia may be decreased in size by a quarter step to size 1.25. As illustrated in the example of FIG. 14B, subject (not shown) provides a correct response at time $t_7$ and size 1.25, an incorrect or no response at time $t_8$ at size 1.25, and correct responses at size 1.25 at times $t_9$ and $t_{10}$. At this point, the example illustrated in FIG. 14B may conclude with the determination that the visual acuity of subject (not shown) may be concluded to presently be that which corresponds to a displayed indicia size of 1.25.

Figure 15:
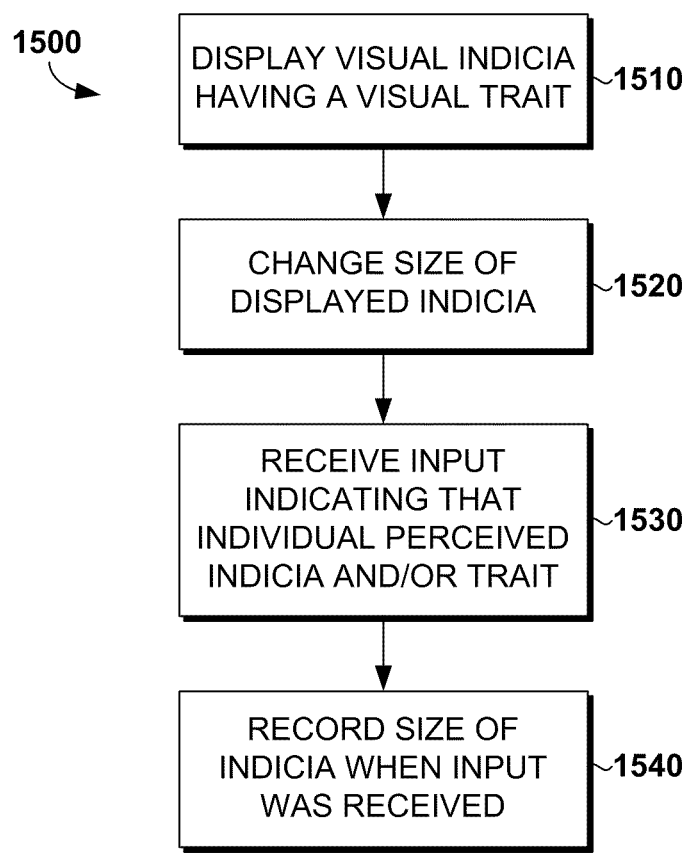
FIG. 15 illustrates a method in accordance with the present invention for testing and/or training static visual acuity.

Referring now to FIG. 15, a method 1500 for testing and/or training static visual acuity in accordance with the present invention is illustrated. In step 1510 a visual indicia having a visual trait may be displayed on a display device viewable by the subject. In step 1520 the size of the displayed indicia may be changed. For example, in step 1520 the displayed visual indicia may be increased in size. In step 1530 an input may be received from the subject indicating that the subject perceived the displayed indicia and/or the trait of the displayed indicia. The input may correspond to the trait possessed by the displayed indicia. In step 1540 the size of the indicia when the input was received may be recorded. Step 1510 may utilize a display device of any type, step 1530 may utilize any type of input device, and step 1540 may utilize any type of storage device. The performance of the steps of method 1500, and the additional methods described herein, may be controlled, directed, or monitored by one or more control units, as described herein.

Figure 16:
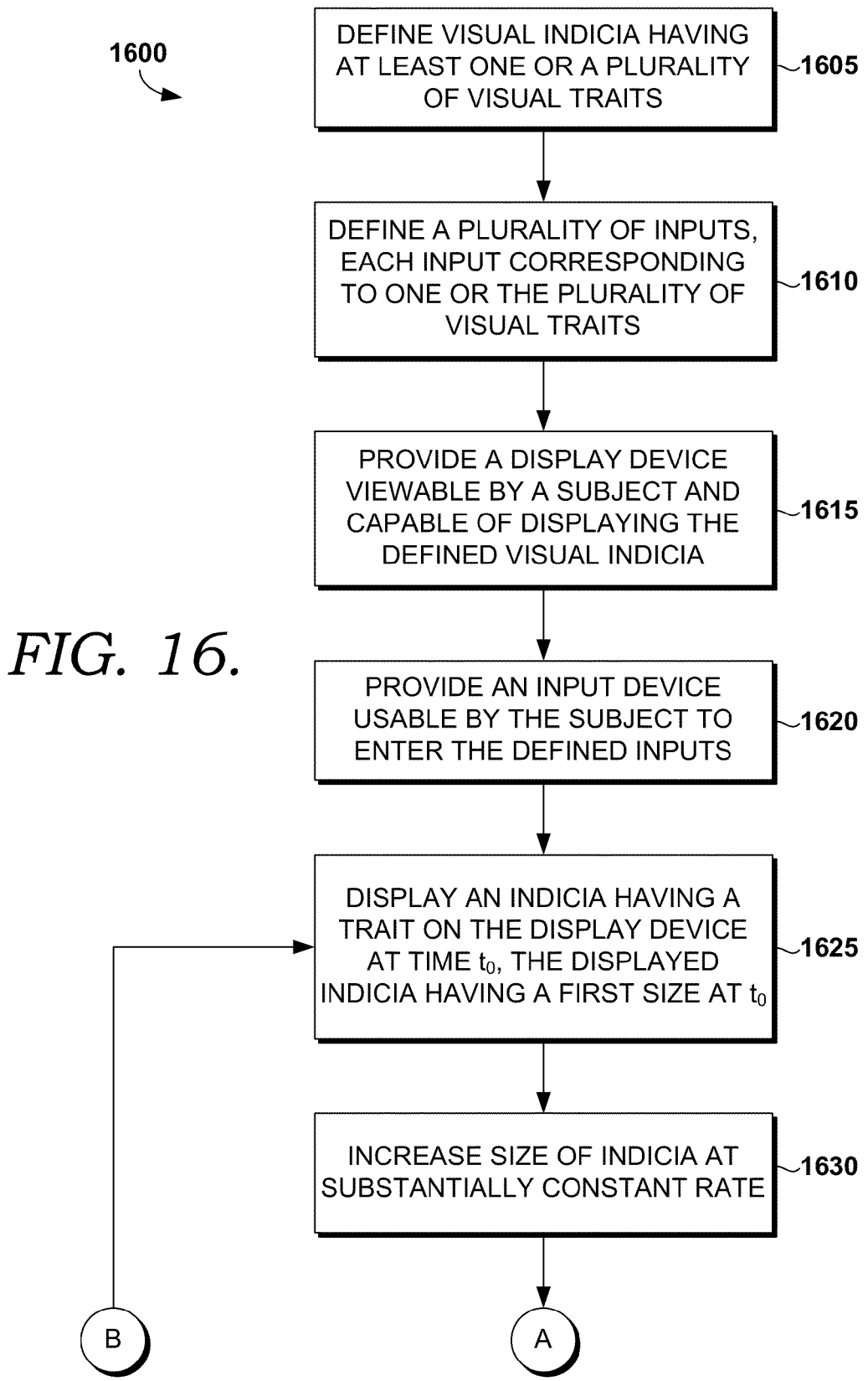
FIG. 16 illustrates a further method in accordance with the present invention for testing and/or training static visual acuity.
Figure 16:
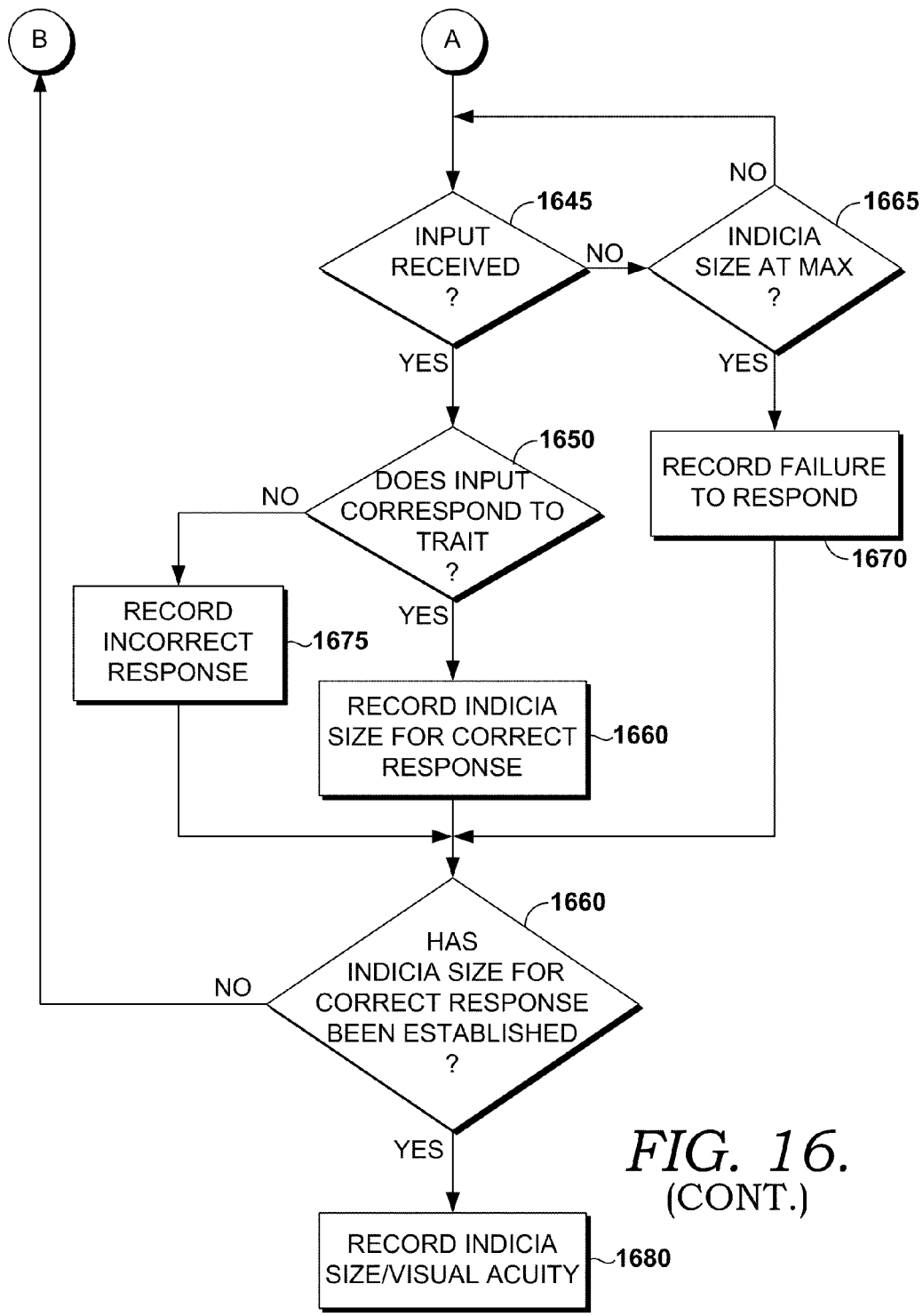

Referring now to FIG. 16, a further method 1600 in accordance with the present invention is illustrated. In step 1605, a visual indicia that may possess at least one of a plurality of visual traits may be defined. In step 1610 a plurality of inputs, each input corresponding to one of the plurality of visual traits may be defined. The inputs defined in step 1610 may correspond in a one to one fashion with the visual traits defined in step 1605. For example, step 1605 may define as visual indicia Landolt Cs having a plurality of visual traits, namely an orientation of upward, downward, leftward, or rightward. Similarly in this example, step 1610 may define a plurality of inputs, each input being a movement of the joystick up, down, left, or right in correspondence with a similar orientation of a displayed Landolt C. In step 1615 a display device may be provided to a subject such that the display device is viewable by the subject and capable of displaying the defined visual indicia. In step 1620 an input device may be provided to the subject that may be used to enter the defined inputs. Step 1620 may provide an input device capable of receiving inputs beyond those defined in step 1610. In step 1625 an indicia may be displayed on the display device having a trait at a time $t_0$, the displayed indicia having a first size at time $t_0$. In step 1630 the size of the displayed indicia may be increased at a substantially constant rate. The substantially constant rate of step 1630 may be linear or a constant stair-step. In step 1645 it is determined whether an input from the input device has been received. If no input has been received, method 1600 proceeds to step 1065 to determine whether the indicia has reached its size maximum. If the conclusion of step 1665 is that the indicia has not yet reached its size maximum method 1600 returns to step 1645 to determine whether an input has been received. If the conclusion of step 1665 is that the indicia has reached the size maximum, method 1600 proceeds to step 1670 of recording a failure to respond. If the conclusion of step 1645 as to whether an input has been received is yes, method 1600 proceeds to step 1650 to determine whether the input received corresponds to the trait of the displayed indicia. If the conclusion of step 1650 is that the input does not correspond to the trait of the displayed indicia, method 1600 proceeds to step 1675 to record an incorrect response. If the conclusion of step 1650 is to determine that the input does correspond to the trait of the displayed indicia, method 1600 proceeds to step 1655 to record the indicia size for the correct response and, optionally, that the response was correct and/or the trait possessed by the indicia. From any of steps 1655, 1670, and steps 1675, method 1600 may proceed to step 1660 to determine whether the indicia size for correct responses has been established. Step 1660 may determine, for example, that the responses of the subject permit a determination of the static visual acuity of the subject. If the determination of step 1660 is that the indicia size for correct responses has not been established method 1600 may return to step 1625 to display another indicia. If the conclusion of step 1660 is that the indicia size for correct responses has been established method 1600 may proceed to step 1680 of recording the indicia size/visual acuity measured for the subject.

Figure 17:
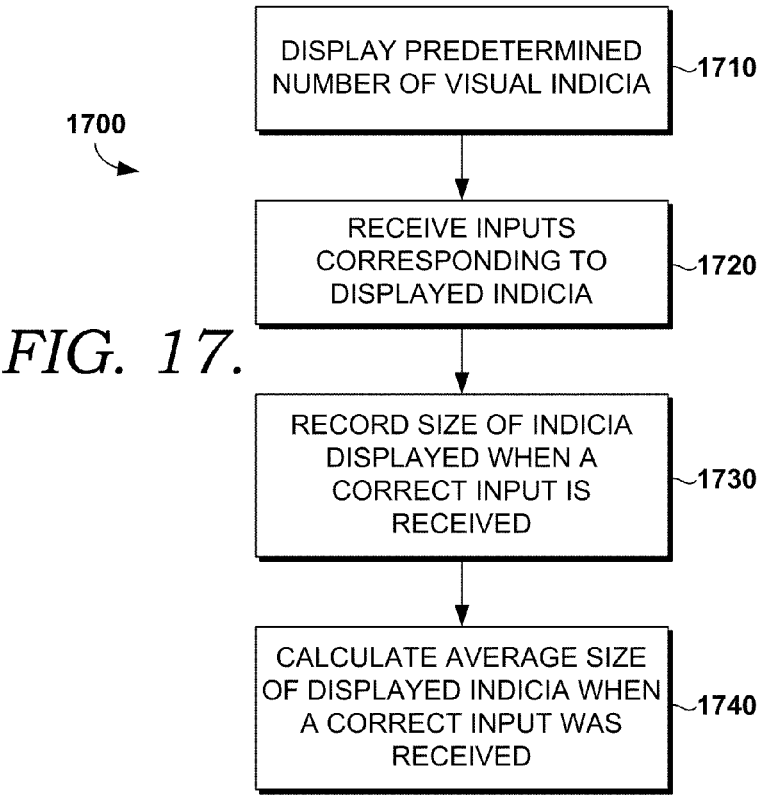
FIG. 17 illustrates a method in accordance with the present invention for testing and/or training the static visual ability of a subject.

Referring now to FIG. 17, a method 1700 for assessing whether the size of a perceptible indicia has been established is illustrated. In step 1710 a predetermined number of visual indicia are displayed. For example, the predetermined number of visual indicia may constitute ten indicia, which, as described further, may be used to attain an average size at which a subject provides a correct response. In step 1720 inputs may be received corresponding to each displayed indicia. In step 1730 the size of indicia displayed when a correct input is received may be recorded. In step 1740 the average size of displayed indicia when a correct input was received may be calculated. In this fashion, steps such as step 1660 of FIG. 16 may constitute simply averaging the size at which a correct response is received for a predetermined number of visual indicia.

Figure 18:
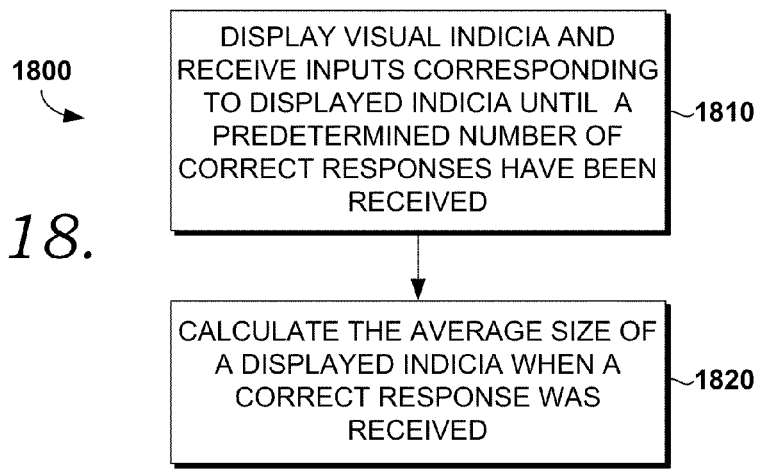
FIG. 18 illustrates a further method in accordance with the present invention for testing and/or training the static visual acuity of an individual.

Referring now to FIG. 18, a further method 1800 for assessing whether the size of a perceptible indicia has been established is illustrated. In step 1810 visual indicia may be displayed and inputs corresponding to the displayed indicia may be received until a predetermined number of correct responses have been received. For example, the display of indicia and the receipt of inputs may continue until a subject has provided ten correct responses. In step 1820 the average size of a displayed indicia when a correct response was received may be calculated. Similarly to method 1700, method 1800 may be utilized to determine at what size of indicia a subject may correctly perceive the indicia and/or its displayed traits. Unlike method 1700, method 1800 requires a predetermined number of correct responses, rather than a predetermined number of trials regardless of the correctness of the response.

Figure 19:
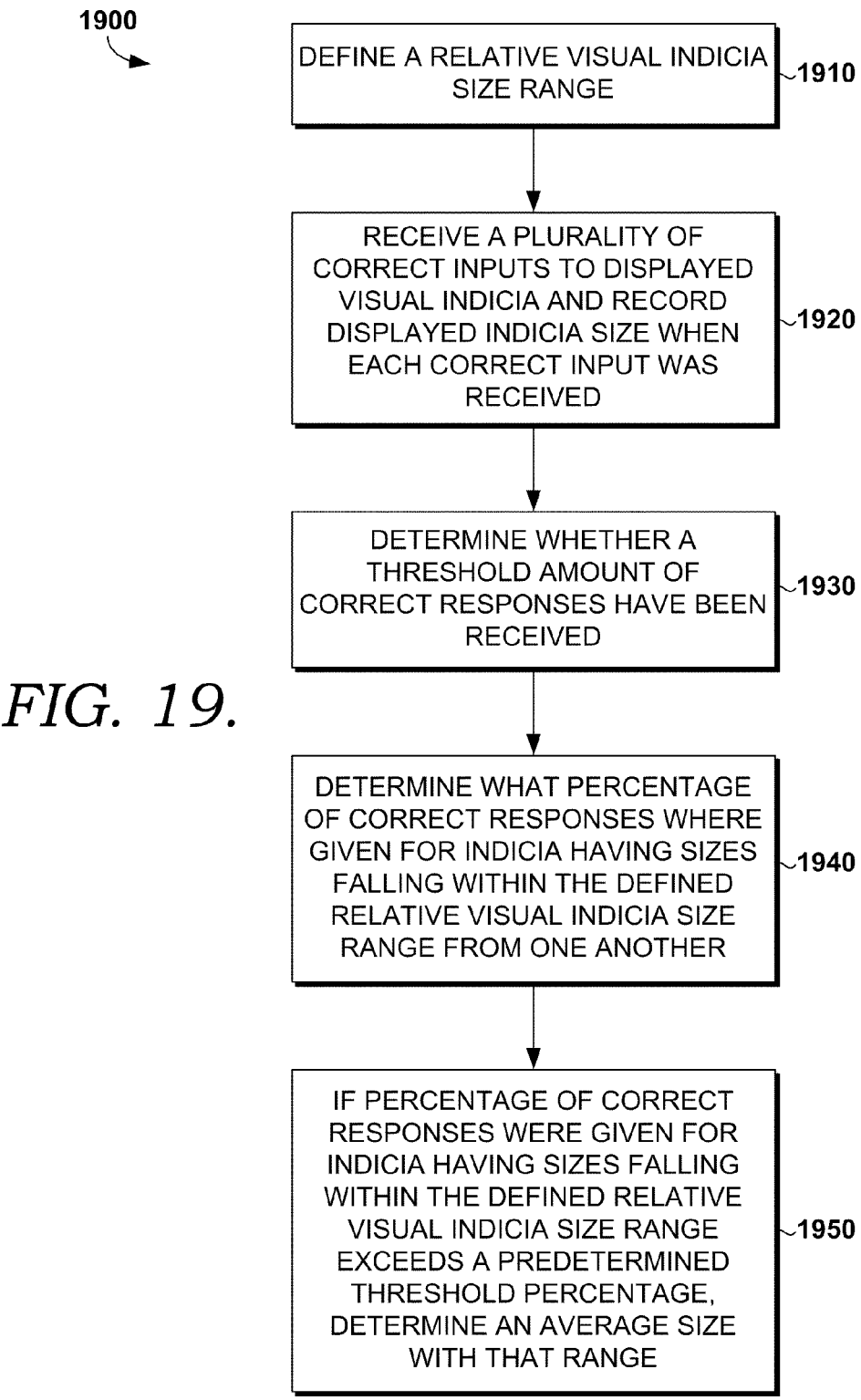
FIG. 19 illustrates a further method in accordance with the present invention for testing and/or training the static visual acuity of an individual.

Referring now to FIG. 19, a method 1900 for assessing the size of a perceptible indicia has been established is illustrated. In step 1910 a relative visual indicia size range may be defined. The size range defined in step 1910 may be absolute, such as an absolute size range of plus or minus two centimeters when displayed on a given display device. The size range defined in step 1910 may, alternatively, be relative, such as within ten percent of the diameter of a displayed indicia. In step 1920 a plurality of inputs correctly corresponding to displayed visual indicia may be received and the displayed indicia size may be recorded for each correct input. In step 1930 a determination may be made as to whether a threshold amount of correct responses have been received. In step 1940 a determination may be made as to what percentage of correct responses were given for indicia having sizes falling within the defined relative visual indicia size range from one another. In step 1950 if the percentage of correct responses to indicia having sizes falling within the defined relative visual indicia size range of step 1910 exceeds a predetermined threshold percentage, such as, for example, eighty percent, it may be determined that an average size within that range corresponds to the static visual acuity of the individual.

Figure 20:
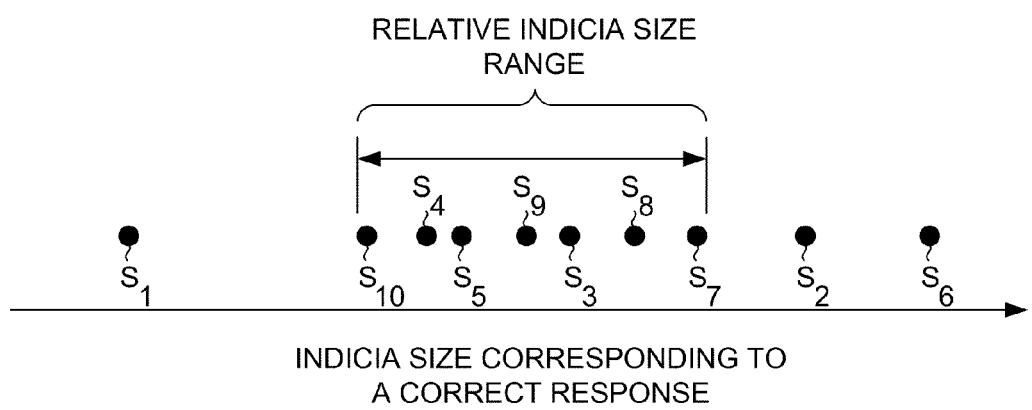
FIG. 20 illustrates an exemplary relative indicia size range attainable in testing and/or training static visual acuity in accordance with the present invention.

Referring now to FIG. 20, a defined relative indicia size range and test and/or training result are illustrated. In the example shown in FIG. 20, ten indicia sizes, denoted $S_1$ through $S_{10}$, are illustrated. Further, a relative indicia size range is shown graphically. Each size of indicia $S_1$-$S_{10}$ corresponds to a correct input from a subject. As illustrated in the example of FIG. 20, seventy percent, namely seven out of ten, of the correct responses were at an indicia size within the defined relative indicia size range. If the predetermined percentage threshold of step 1950 in method 1900 were seventy percent, then the receipt of a tenth correct input at size $S_{10}$ would permit the conclusion of testing with the calculation of the average of indicia sizes falling within the relative indicia size range as a measure of the static visual acuity of the individual. In the example illustrated in FIG. 20, the sizes of indicia corresponding to correct responses were sizes $S_3$, $S_4$, $S_5$, $S_8$, $S_9$, and $S_{10}$.

Figure 21:
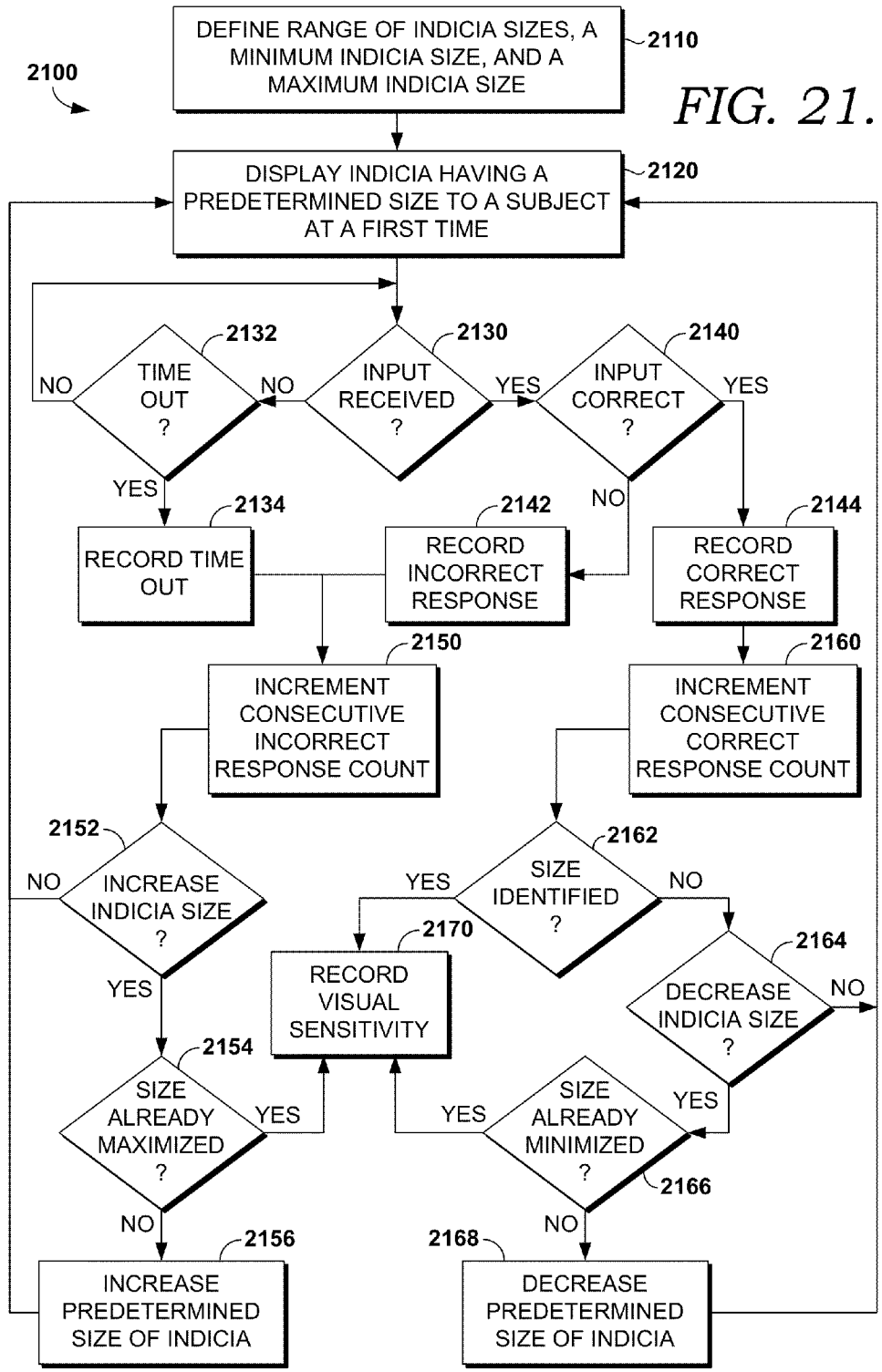
FIG. 21 illustrates a further method in accordance with the present invention for testing and/or training the visual sensitivity of a subject.

Referring now to FIG. 21, a further method 2100 in accordance with the present invention for testing and/or training visual sensitivity using adaptable indicia is illustrated. In step 2110 a range of indicia sizes, a minimum indicia size, and a maximum indicia size may be defined. The definition in step 2110 may be in terms of number of pixels, absolute physical size of an indicia on a display device, visual field occupied by the indicia from the point of view of a subject, or any other way of denoting size of an indicia. In step 2120 an indicia having a predetermined size is displayed to a subject at a first time. After the display of an indicia in step 2120, method 2100 proceeds to step 2130 to determine whether an input has been received. If no input has been received, step 2132 determines whether a timeout has occurred. The duration of time during which a system in accordance with the present invention may wait to receive an input from a subject before a timeout occurs may vary based upon the desires of the subject, the desires of those providing the visual sensitivity testing and/or training, the skill level of a subject, or other factors. If the conclusion of step 2132 is that no timeout has occurred, method 2100 may continue waiting to receive an input in step 2130. If the conclusion of step 2132 is that a timeout has occurred, method 2100 may proceed to record the timeout on a storage device. Step 2134 of recording the timeout condition may also record the circumstances of the timeout, such as the size of the displayed indicia, the orientation or other trait possessed by the displayed indicia, information identifying the subject participating in the testing and/or training, or any other information. If the conclusion of step 2130 is that input has been received, method 2100 may proceed to step 2140 to determine whether that input was correct. For example, an input may correctly identify a trait possessed by a displayed visual indicia. If the input was incorrect, method 2100 may proceed to step 2142 to record the incorrect response. Similarly to step 2134 of recording a timeout, step 2142 of recording an incorrect response may further record additional information regarding the circumstances and time at which the incorrect response was received. After either of steps 2134 and step 2142, method 2100 may proceed to step 2150 to increment a consecutive incorrect response count, should such a count be desired. An incorrect response count, such as may be incremented and kept in step 2150, may be used to determine whether or not to increase an indicia size or ultimately conclude that testing and/or training have reached the minimum visual threshold of an individual. Method 2100 may then proceed to step 2152 to determine whether to increase indicia size. Step 2152 may be based, for example, upon the number of consecutive incorrect responses that have been provided by a subject at a given indicia size. For example, if less than two consecutive incorrect responses have been given by a subject, step 2152 may determine not to increase the size of a displayed indicia for further iterations of method 2100, in which case method 2100 may return to step 2120 of displaying an indicia having the same predetermined size. If the conclusion of step 2152 is that the indicia size should be increased, method 2100 may proceed to step 2154 to determine whether the indicia size is already maximized, as previously defined in step 2110. If the conclusion of step 2154 is that the indicia size is already maximized, method 2100 may proceed to step 2170 of recording the visual sensitivity of the subject as being no better than that corresponding to accurately perceiving the largest maximum defined indicia size. If the conclusion of step 2154 is that the indicia size is not already maximized, method 2100 may proceed to step 2156 of increasing the predetermined size of an indicia. After increasing the predetermined size of an indicia in step 2156, method 2100 may return to step 2120 of displaying an indicia having a predetermined size using the indicia of increased size as defined by step 2156. Step 2156 may determine the amount of size increase of an indicia in any of a variety of fashions, such as, but not limited to, using a stair step function similar to that described in FIG. 14B. Additional functions or methodologies may be implemented to accomplish a similar result. Therefore, it is contemplated that the stair step function, as illustrated in FIG. 14B, is not limiting, but merely exemplary.

If, however, the conclusion of step 2140 is that a correct input has been received, method 2100 may proceed to step 2144 and record the correct response. Step 2144 may record additional information regarding the circumstances and time of the correct response, similarly to the recording of steps 2134 and 2142. Method 2100 may then proceed to step 2160 of incrementing the consecutive correct response count. Similar to the consecutive incorrect response count incremented and maintained in step 2150, the incremental consecutive correct response count incremented and maintained in step 2160 may be utilized to determine when to increase the size of a displayed visual indicia and/or when to determine that the visual sensitivity of the subject has been determined for testing and/or training purposes. For example, method 2100 may proceed to step 2162 to determine whether the size defining the visual sensitivity of the subject has been identified. Step 2162 may, for example, utilize prior recorded correct, incorrect, and timeout responses to conclude that the size of the indicia for the last correct response cannot be reduced without reaching a size at which the subject has provided one or more incorrect responses. If the conclusion of step 2162 is that the size of the indicia defining the visual sensitivity of the subject has been identified, method 2100 may proceed to step 2170 of recording that visual sensitivity. If the conclusion of step 2162 is that the size of the visual indicia defining the visual sensitivity of the subject has not yet been identified, method 2100 may proceed to step 2164 of determining whether to decrease the indicia size. Step 2164 may, for example, utilize the consecutive response count incremented in step 2160 to decrease the size of the next displayed indicia only if a predetermined number of consecutive responses, such as the two consecutive correct responses in the example illustrated previously in FIG. 14B, have been received. If the conclusion of step 2164 is that the indicia size should not be decreased, method 2100 may return to step 2120 of displaying an indicia having the predetermined size. If the conclusion of step 2164 is that the indicia size should be further decreased, method 2100 may proceed to step 2166 to determine whether the indicia size has already reached the minimum size defined previously in step 2110. If the conclusion of step 2166 is that the indicia size is not already minimized, method 2100 may proceed to step 2168 of decreasing the predetermined size of the indicia. Step 2168 may determine the size of the decrease in any of a variety of fashions, such as in the step-wise approach illustrated in the example of FIG. 14B previously. After decreasing the predetermined size of the indicia in step 2168, method 2100 may return to step 2120 of displaying an indicia having a predetermined size using the newly decreased predetermined size determined in step 2168. If the determination of step 2166 is that the indicia size has already been minimized, method 2100 may return to step 2170 of recording the visual sensitivity of the subject as being at worst that defined by the minimum indicia size. Of course, the various steps illustrated as part of exemplary method 2100 may be varied in order, and some may be omitted entirely.

Figure 22:
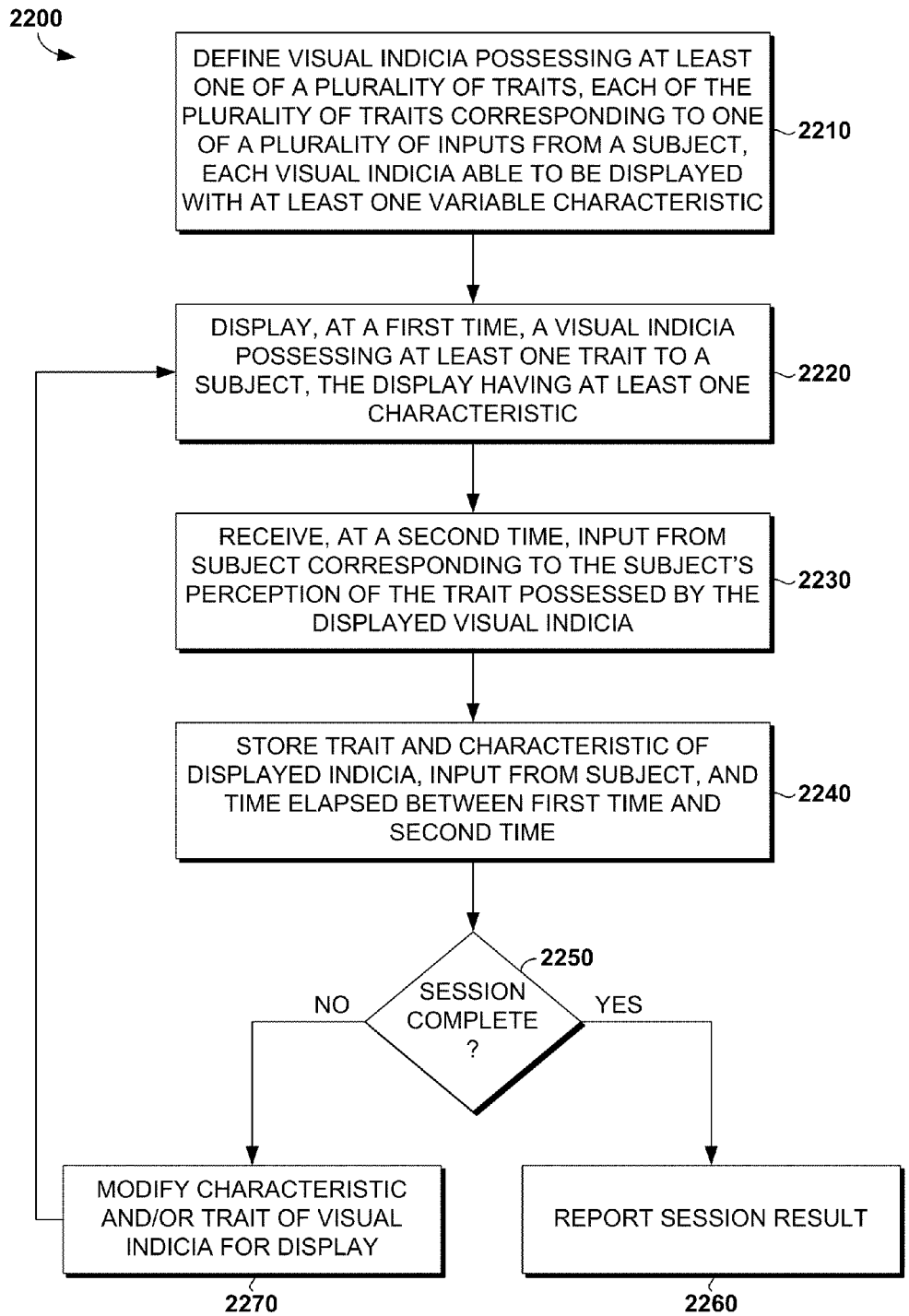
FIG. 22 illustrates a further method in accordance with the present invention for testing and/or training the visual sensitivity of a subject.

Referring now to FIG. 22, a further method 2200 of testing and/or training the visual sensitivity of a subject using adaptable indicia is illustrated. In step 2210, visual indicia possessing at least one of a plurality of traits, each of the plurality of traits corresponding to one of a plurality of inputs from a subject and each visual indicia able to be displayed with at least one variable characteristic may be defined. For example, the visual trait defined for indicia in step 2210 may comprise the orientation of a Landolt C, the identity of a letter or other displayed image, etc. The characteristic of a visual indicia defined in step 2210 may be characteristics such as the visual size of the indicia, the duration of display of the indicia, the location of the indicia on a display device, the contrast of the indicia relative to a visual background, the color of the indicia, the state of motion of the indicia, etc. Method 2200 may then proceed to step 2220 of displaying, at a first time, a visual indicia possessing at least one trait to a subject and having at least one characteristic. Method 2200 may then proceed to step 2230 of receiving, at a second time, an input from the subject corresponding to the subject's perception of the trait possessed by the displayed visual indicia. Step 2230 may include determining that a timeout has occurred due to the failure of a subject to respond to a displayed indicia during a predetermined amount of time. In step 2240, the trait and characteristic of the displayed indicia may be stored, as well as the input from the subject, and the time elapsed between the first time at which the indicia was displayed and the second time at which the input was received from the subject. If a timeout condition was received in step 2230, that information may be recorded as well in step 2240. Further, step 2240 may record and store additional information regarding the testing and/or training iteration, such as the identity of the subject, the time of day, other visual properties associated with the testing and/or training session, etc. Method 2200 may proceed to step 2250 to determine whether the session of testing and/or training is complete. If the conclusion of step 2250 is that the session is complete, method 2200 may proceed to step 2260 to provide a report of the session result. The report generated in step 2260 may describe the performance of the subject during testing and/or training in any degree of detail, including an evaluation of the visual sensitivity of the subject obtained through the use of method 2200. The report generated in step 2260 may comprise a data base entry on a storage device, any other type of electronic record in any kind of volatile or non-volatile electronic memory device, a summary of performance provided on the same display device used for method 2200, a summary of information displayed on any other display device, a physical printout of results on paper or other media, or any other type of report. If the conclusion of step 2250 is that the session was not complete, method 2200 may proceed to step 2270 of modifying a visual characteristic and/or trait of the visual indicia for display. With the modified characteristic and/or trait of the visual indicia from step 2270, method 2200 may return to step 2220 of displaying a visual indicia at a first time possessing the modified characteristic and/or trait.

The examples provided herein merely serve to illustrate some aspects of the present invention. For example, a variety of indicia, including letters, digits, pictures of common everyday objects, and the like may be utilized as a visual indicia. Further, any number of methods and approaches to determining at what size an indicia is being most accurately perceived by a subject may be utilized, and similarly a variety of methods and approaches may be used to determine the speed at which an individual may correctly perceive an indicia. Further, a displayed indicia may possess multiple visual traits, the perception of the desired trait may be part of the testing in accordance with the present invention. Of course, the present invention is not limited to any particular type of display device, input device, test unit, storage device, or other equipment. Further, any number of such devices or components may be used, and some devices or components described herein may be combined with others, or a single device may be implemented in numerous devices.

Contrast Sensitivity Testing and/or Training

In accordance with the present invention, contrast sensitivity testing and/or training may utilize a plurality of circular contrast zones, with one of the plurality of circular contrast zones possessing a contrast pattern greater or lesser than the other circular contrast zones. Contrast sensitivity testing and/or training may proceed by asking a subject to select the contrast zone of the plurality having the highest or lowest contrast pattern. Each of the contrast zones presented at a given time may possess a total amount of luminance that is equivalent, with only the contrast of any given circular contrast zone varying. The plurality of circular contrast zones used in accordance with the present invention may be presented in a spatially distributed manner on a display device. Input(s) identifying one of the plurality of circular contrast zones may be received on an input device that enables a subject to provide one or more input corresponding to the spatial distribution of circular contrast zones on the display device, thereby enabling the subject to uniquely identify one or more circular contrast zone with an input. Appropriate input devices may include touch sensitive screens, joysticks, buttons, multi-touch input devices, and the like.

In contrast sensitivity testing, a contrast pattern is displayed to a subject to determine whether or not the subject can perceive the contrast pattern. One challenge in testing the contrast sensitivity of a subject arises if the subject possesses astigmatism, which may prevent the subject from perceiving contrast patterns when they are aligned with vision defects arising from that astigmatism. This difficulty may be overcome by using circular contrast zones which possess circular contrast patterns. The circular contrast pattern of such a circular contrast zone may extend in a 360° fashion so that it cannot be aligned with a given subject's visual defects resulting from astigmatism.

The spatial frequency of a circular contrast zone in accordance with the present invention may vary for different embodiments or for different testing and/or training iterations within the same embodiment. The spatial frequency of a circular contrast zone depends upon the size of the circular contrast zone, the distance of the subject from the display device displaying the circular contrast zone, and the number of contrast pattern cycles within the circular contrast zone. While a variety of contrast patterns may be used in accordance with the present invention, a symmetrical sinusoidal grating contrast pattern can present a relatively significant challenge to a subject. One example of sinusoidal grating contrast patterns are Gabor patches, which are sometimes used in contrast sensitivity testing. However, Gabor patches are not symmetrical and, therefore, the perception of the contrast pattern of a Gabor patch can be compromised by astigmatism. If a relatively small challenge to a subject is desired, a square wave contrast pattern may be used. Any type of contrast pattern may be utilized in a circular contrast zone in accordance with the present invention. If an irregular contrast pattern is used, the spatial frequency of the contrast pattern may vary along the radius of the circular contrast zone. If a regular contrast pattern is used, any spatial frequency may be utilized. The spatial frequency of the contrast pattern of a circular contrast zone may be expressed as a number of cycles per degree of vision of the subject. Spatial frequencies such as 18 cycles per degree and/or 6 cycles per degree may be used, for example. A wide range of contrasts may be tested across a wide range of spatial frequencies using circular contrast zones in accordance with the present invention.

Figure 23A:
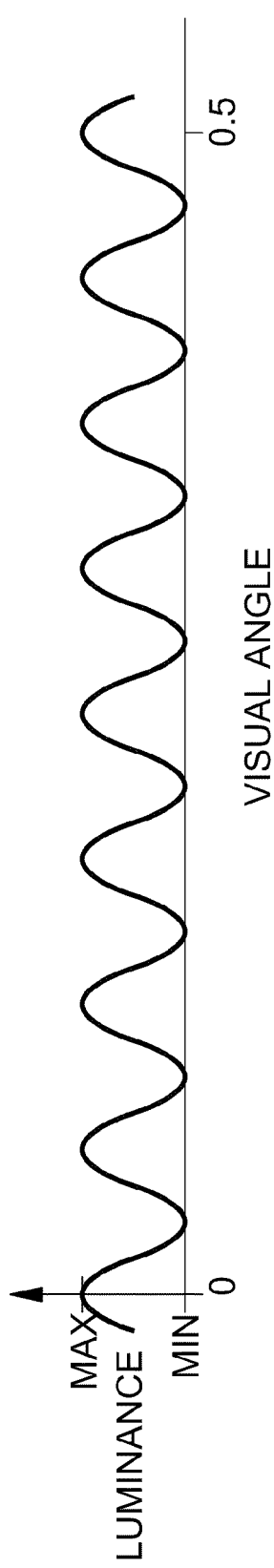
FIGS. 23A-23B illustrate graphical depictions of the luminance patterns of sinusoidally varying circular contrast zones as a function of visual angle.
Figure 23B:
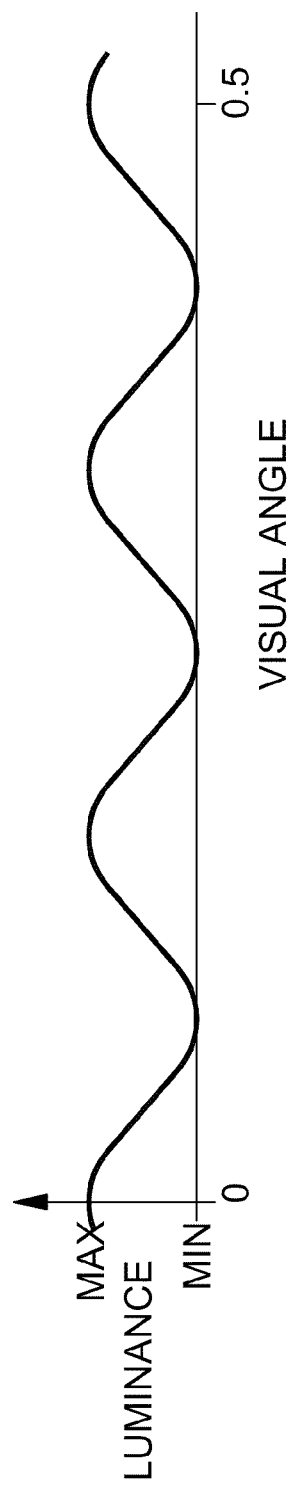
Figure 24A:
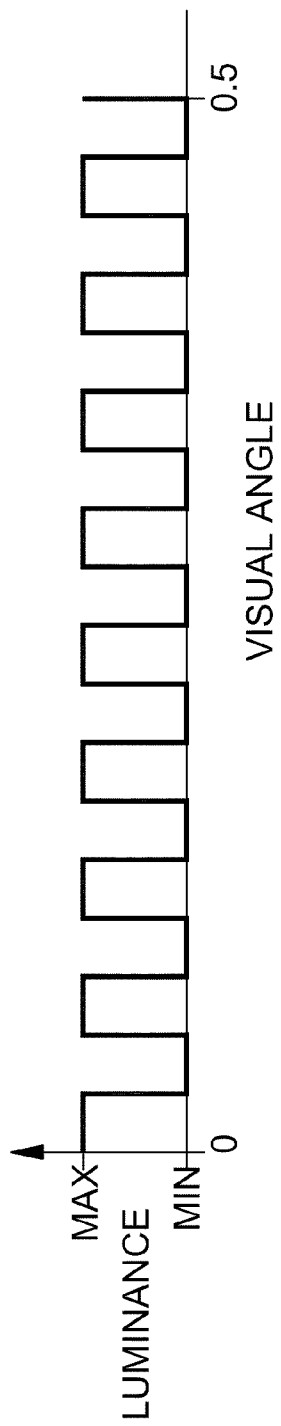
FIGS. 24A-24B illustrate graphical depictions of the luminance patterns of square wave varying circular contrast zones as a function of visual angle.
Figure 24B:
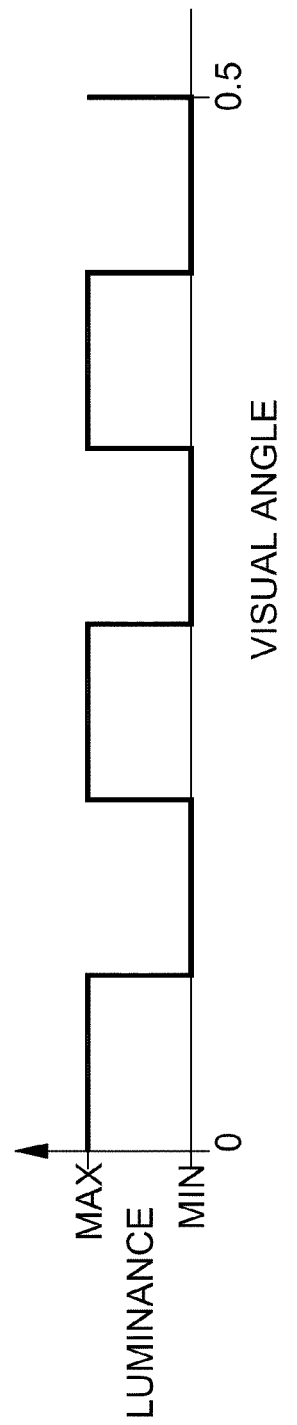

FIGS. 23A-23B and 24A-24B graphically illustrate exemplary luminance patterns that may be used in conjunction with circular contrast zones in accordance with the present invention as a function of visual angle. FIGS. 23A-23B and 24A-24B depict the luminance of a given contrast pattern as the luminance varies from the maximum luminance value within the circular contrast zone, denoted as "max," to the minimum luminance value within the circular contrast zone, denoted as "min," as the luminance varies across the angular field of view of a subject. While the maximum luminance and the minimum luminance depicted in FIGS. 23A-23B and 24A-24B may be the maximum luminance attainable by a display device and the minimum luminance attainable by a display device, respectively, the luminance of a given circular contrast zone need not vary over the full range of luminance possible for the display device utilized. FIGS. 23A-23B and 24A-24B depict the luminance of a circular contrast zone across one half of a degree of vision, although circular contrast zones may occupy more or less than this distance. FIGS. 23A-23B and 24A-24B depict the luminance across the diameter of exemplary circular contrast zones. FIG. 23A illustrates the sinusoidal variation of luminance with a frequency of 18 cycles per degree across the diameter of a circular contrast zone. FIG. 23B illustrates the sinusoidal variation of luminance with a frequency of 6 cycles per degree across the diameter of a circular contrast zone. FIG. 24A illustrates a square wave variation of luminance with a frequency of 18 cycles per degree across the diameter of a circular contrast zone. FIG. 24B illustrates a square wave variation of luminance with a frequency of 6 cycles per degree across the diameter of a circular contrast zone. Any cyclical or non-cyclical pattern may be used in conjunction with a circular contrast zone in accordance with the present invention beyond the patterns illustrated in FIGS. 23A-23B and 24A-24B. For example, a circular contrast zone may have a single portion with a luminance that differs from the rest of the circular contrast zone. By way of further example, a circular contrast zone may have a non-periodic variance in luminance.

Additionally, the present invention permits the use of a plurality of circular contrast zones simultaneously, from which a subject may select a single circular contrast zone. For example, a subject may be instructed to select the contrast zone having the highest or lowest contrast pattern. In this way, multiple testing and/or training iterations may display a plurality of circular contrast zones with the test subject selecting one, such as the highest contrast pattern or the lowest contrast pattern. The difference in contrast may vary for different iterations in accordance with the present invention to assess the degree of contrast difference that is just noticeable, thereby accurately measuring the contrast sensitivity of a subject, rather than merely determining whether a subject may perceive a given degree of contrast, such as may be utilized for some screening purposes. The contrast of a circular contrast zone may be defined in a variety of ways. One useful measure of the contrast of a contrast zone is sometimes referred to as "modulation" or "Michelson contrast." The Michelson contrast, denoted M, may be calculated based on the maximum and minimum luminances of a contrast zone based on the equation: $M=(^L max-^L min)/(^L max+^L min)$. In some instances, a contrast zone may be uniform, such that $(^L max=^L min)$, in which case M=0. Of course, other measures/definitions of contrast may be used. The contrast sensitivity testing in accordance with the present invention may utilize an input device that may receive inputs corresponding to a spatial distribution of the displayed circular contrast zones. In this fashion, a subject may easily and rapidly select an individual contrast zone that the subject believes to be the correct response to a given display of a plurality of contrast zones. An analysis of the time elapsed between the display of a plurality of contrast zones and the receipt of an input indicating the selection of one of the plurality of circular contrast zones may provide additional information regarding the contrast sensitivity abilities of a subject. A variety of input devices may be utilized in conjunction with contrast sensitivity testing in accordance with the present invention. Some of the examples of appropriate input devices are joysticks, buttons, touch sensitive screens, and gesture recognition. However, any other type of input device may be utilized, such as voice recognition, foot pedals, balance boards, and the like.

Figure 25:
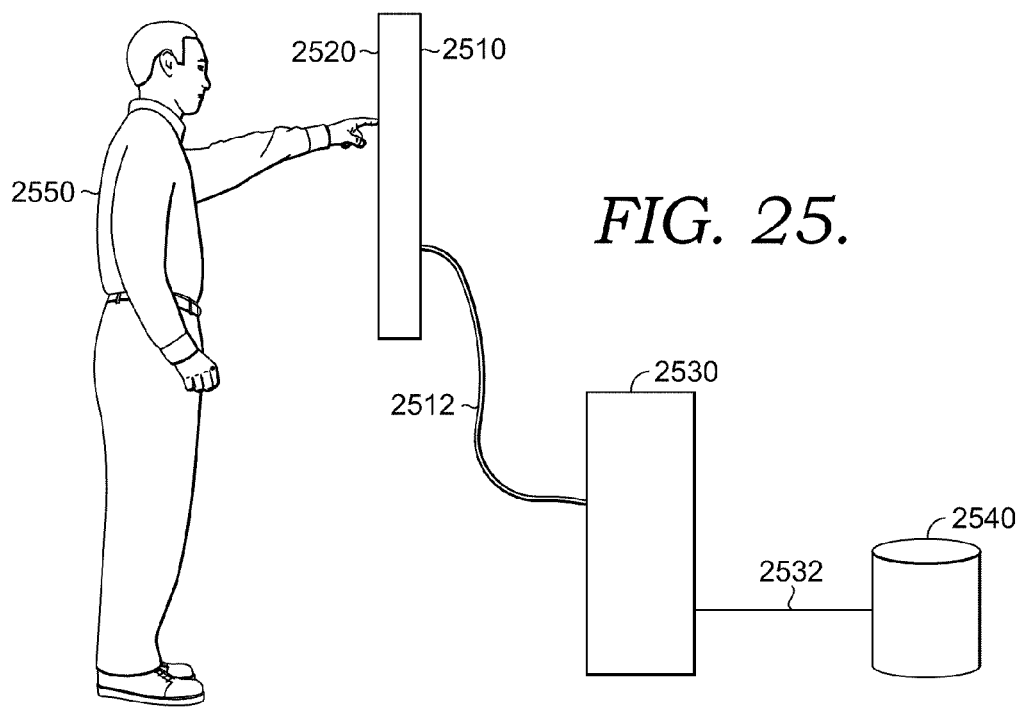
FIG. 25 illustrates a further system for testing and/or training contrast sensitivity in accordance with the present invention.

Referring now to FIG. 25, a further system 2500 in accordance with the present invention for testing and/or training the contrast sensitivity of a subject 2550 is illustrated. System 2500 may utilize display device 2510 having a touch sensitive screen 2520. In this way, display device 2510 may display a plurality of circular contrast zones to subject 2550, and subject 2550 may register a selection of one of the plurality of circular contrast zones by touching touch sensitive screen 2520, for example at or near the selected circular contrast zone. Cable 2512 may connect display device 2510 to control unit 2530. Control unit 2530 may operate to cause display device 2510 to display a plurality of circular contrast zones and may receive inputs from touch sensitive screen 2520. Testing unit 2530 may communicate testing data to storage unit 2540 via connection 2532, but any other type of media or protocol may be used.

Figure 26:
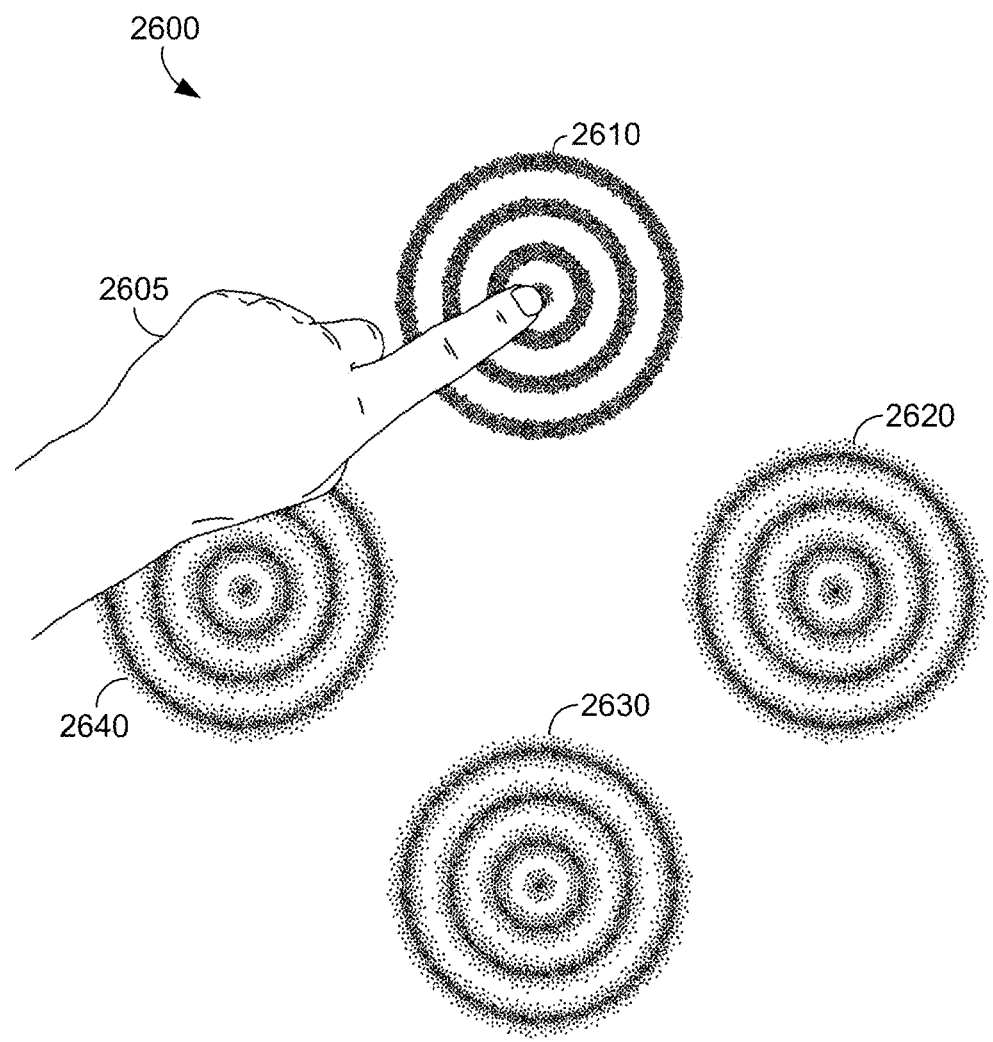
FIG. 26 illustrates various touch screen contrast sensitivity testing and/or training systems in accordance with the present invention.

Referring now to FIG. 26, a plurality 2600 of circular contrast zones may comprise a top contrast zone 2610, a right contrast zone 2620, a bottom contrast zone 2630, and a left contrast zone 2640. In the example illustrated in FIG. 26, top contrast zone 2610 possesses the highest contrast pattern of the plurality 2600 of circular contrast zones. Subject (not illustrated) may select top contrast zone 2610 by touching the screen where top contrast zone 2610 is displayed, for example by using the hand 2605 of subject.

Figure 27:
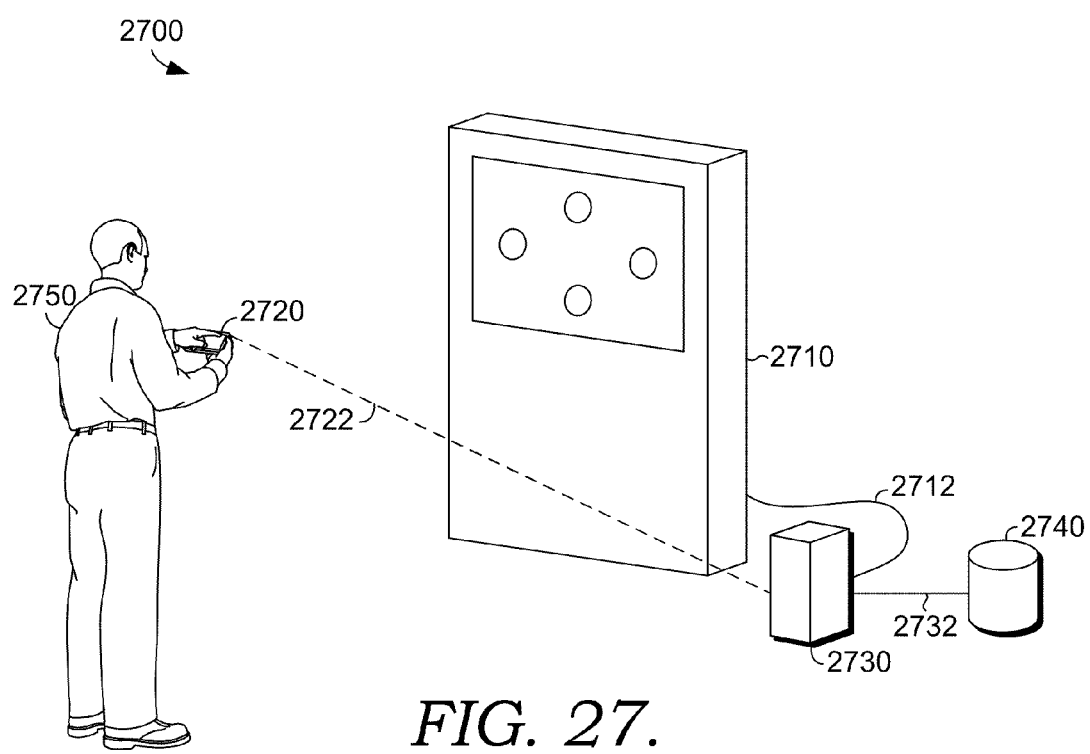
FIG. 27 illustrates a further system for testing and/or training contrast sensitivity in accordance with the present invention utilizing a multi-touch input device.

Referring now to FIG. 27, a further system 2700 for testing and/or training the contrast sensitivity of a subject 2750 is illustrated. Circular contrast zones may be displayed to subject 2750 on display device 2710. Subject 2750 may register a selection of a circular contrast zone displayed on display device 2710 using a multi-touch device 2720, such as an iPod® touch. Multi-touch device 2720 may connect to control unit 2730 over a wireless link 2722. Wireless link 2722 may utilize Bluetooth, 802.11, or any other standard or nonstandard wireless communication protocol. Control unit 2730 may connect to display device 2710 via connection 2712. Control unit 2730 may control the display of circular contrast zones on display device 2710 when inputs are registered by subject 2750. Control unit 2730 may transmit data to storage device 2740 via connection 2732 for storage.

Referring now to FIGS. 28A-28D, various arrangements of circular contrast zones and input receipts using a multi-touch device are illustrated.

Figure 28A:
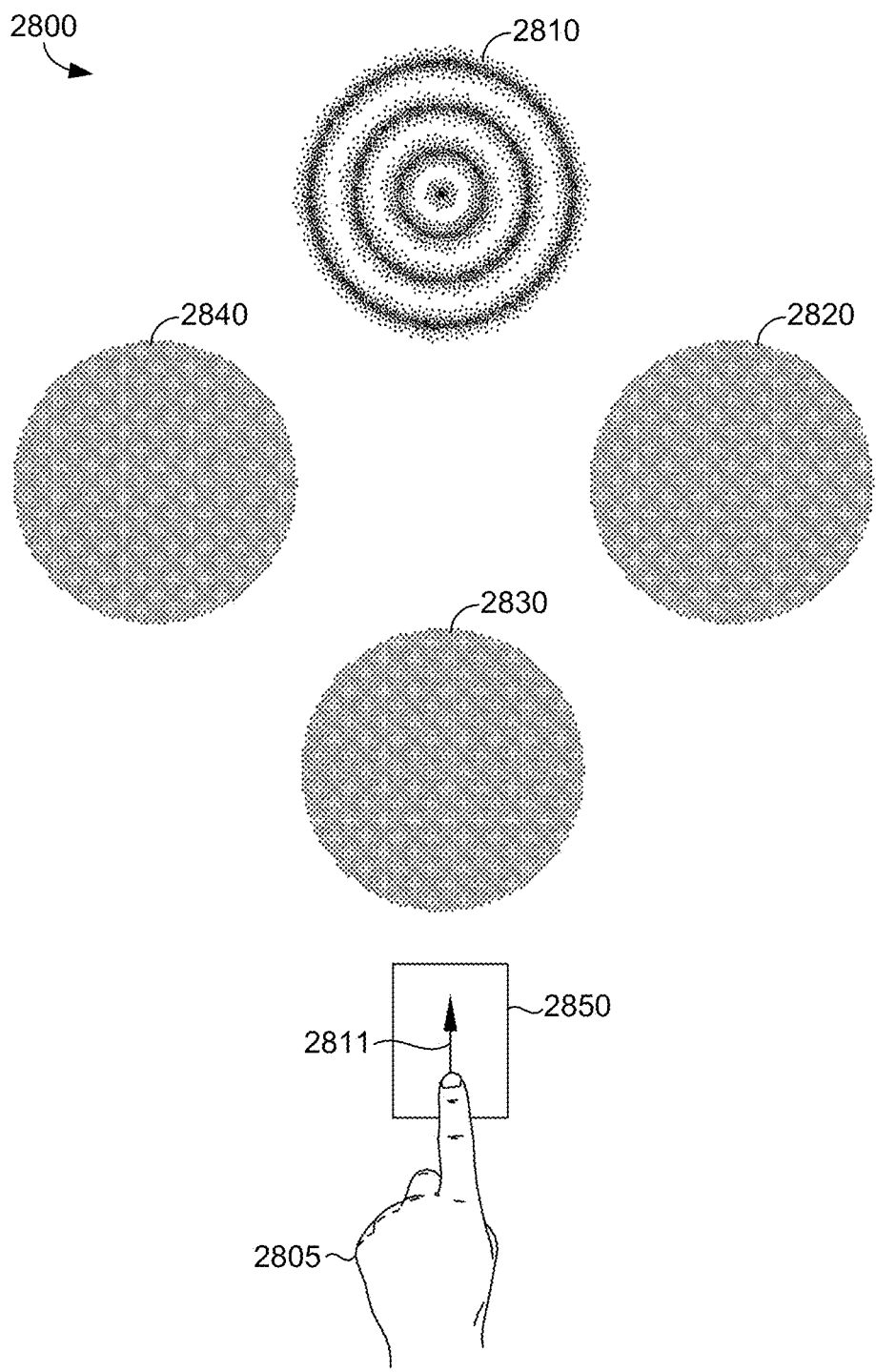
FIGS. 28A-28D illustrate various pluralities of circular contrast zones and inputs using a multi-touch input device in accordance with the present invention.

Referring now to FIG. 28A, a plurality 2800 of circular contrast zones may comprise a top contrast zone 2810, a right contrast zone 2820, a bottom contrast zone 2830, and a left contrast zone 2840. In the example of FIG. 28A, top contrast zone 2810 possesses a higher contrast pattern than the other contrast zones of plurality 2800. In the example of FIG. 28A, right contrast zone 2820, bottom contrast zone 2830, and left contrast zone 2840 possess zero contrast, in that they are uniform in luminance. In the example of FIG. 28A, subject (not illustrated) may indicate the selection of top contrast zone 2810 by contacting multi-touch device 2850 in an upward direction 2811 using hand 2805.

Figure 28B:
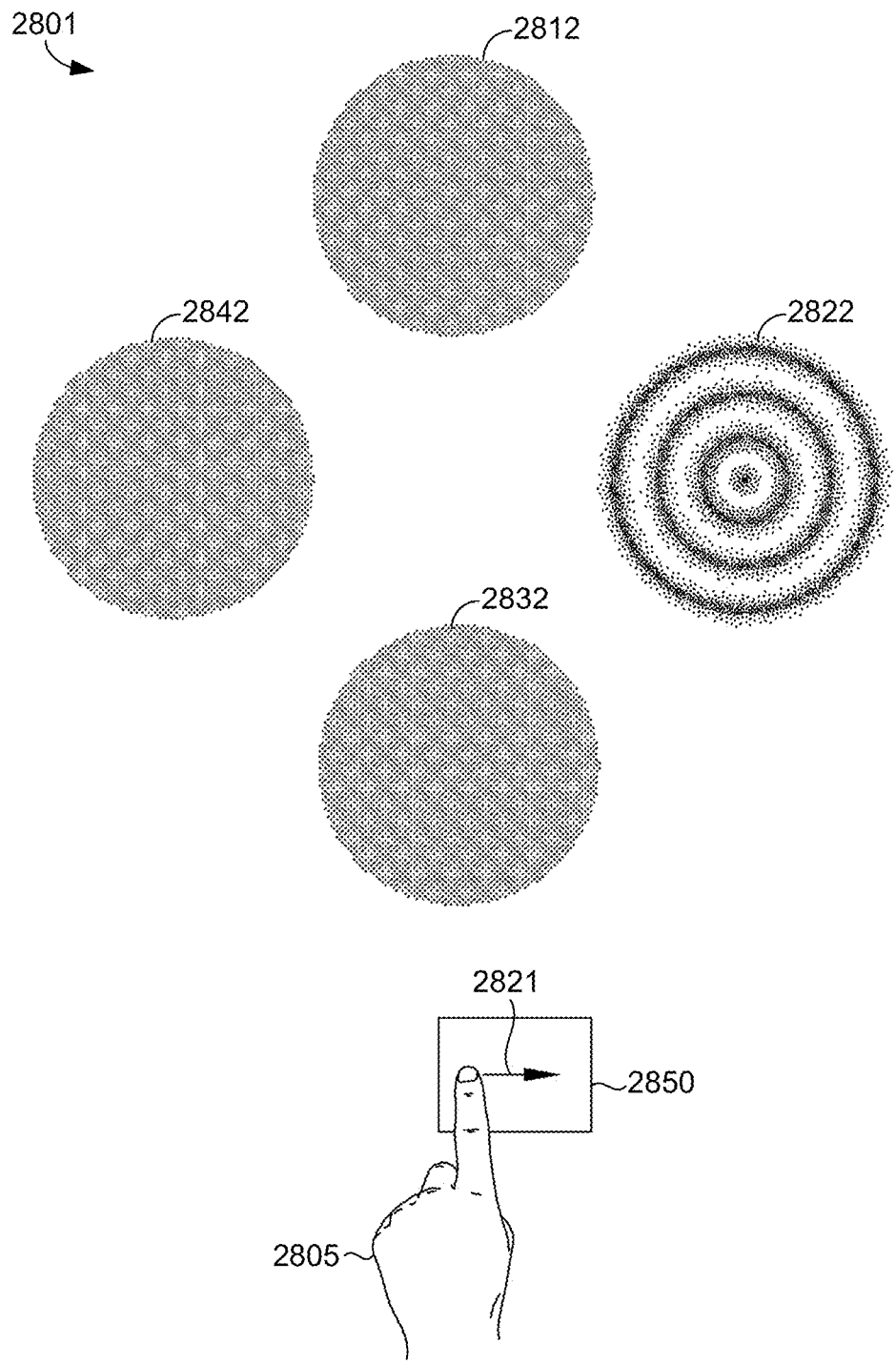

Referring now to FIG. 28B, a plurality 2801 of contrast circular zones may comprise a top contrast zone 2812, a right contrast zone 2822, a bottom contrast zone 2832, and a left contrast zone 2842. In the example of FIG. 28B, right contrast zone 2822 possesses a higher contrast pattern than the other circular contrast zones of plurality 2801. Subject (not illustrated) may indicate the selection of right contrast zone 2822 by contacting multi-touch device 2850 in a rightward direction 2821 with hand 2805.

Figure 28C:
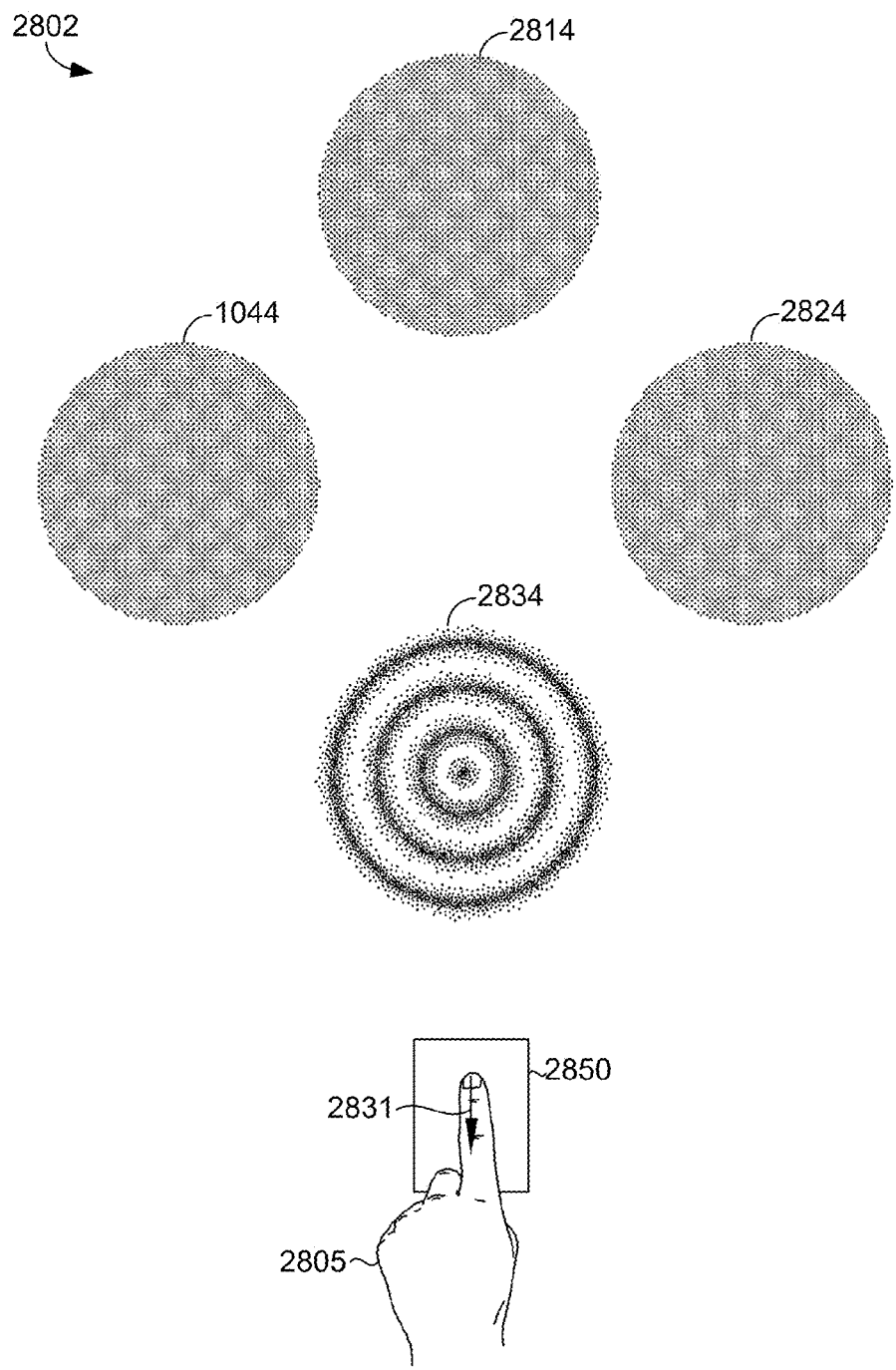

Referring now to FIG. 28C, a plurality 2802 of circular contrast zones is illustrated. Plurality 2802 comprises top contrast zone 2814, right contrast zone 2824, bottom contrast zone 2834, and left contrast zone 2844. In the example illustrated in FIG. 28C, bottom contrast zone 2834 possesses a higher contrast pattern than the other circular contrast zones of plurality 2802. Subject (not illustrated) may indicate the selection of bottom contrast zone 2834 by contacting multi-touch device 2850 in a downwards direction 2831 with hand 2805.

Figure 28D:
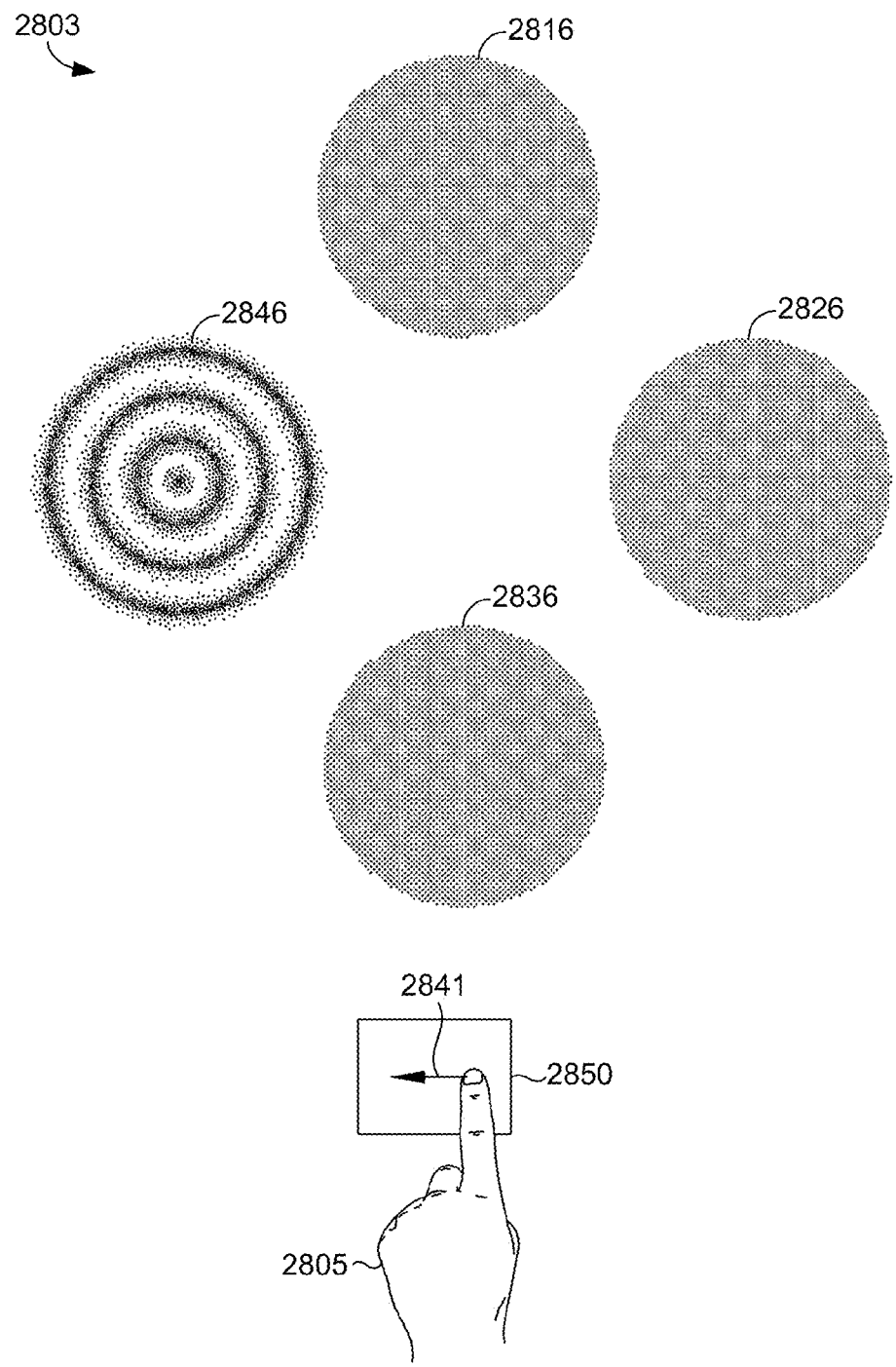

Referring now to FIG. 28D, a plurality 2803 of circular contrast zones is illustrated. Plurality 2803 may comprise a top contrast zone 2816, a right contrast zone 2826, a bottom contrast zone 2836, and a left contrast zone 2846. In the example of FIG. 28D, left contrast zone 2846 possesses a higher contrast pattern than the other contrast zones of plurality 2803. Subject (not illustrated) may indicate the selection of left contrast zone 2846 by contacting multi-touch device 2850 in a leftward direction 2841 with hand 2805.

Figure 29:
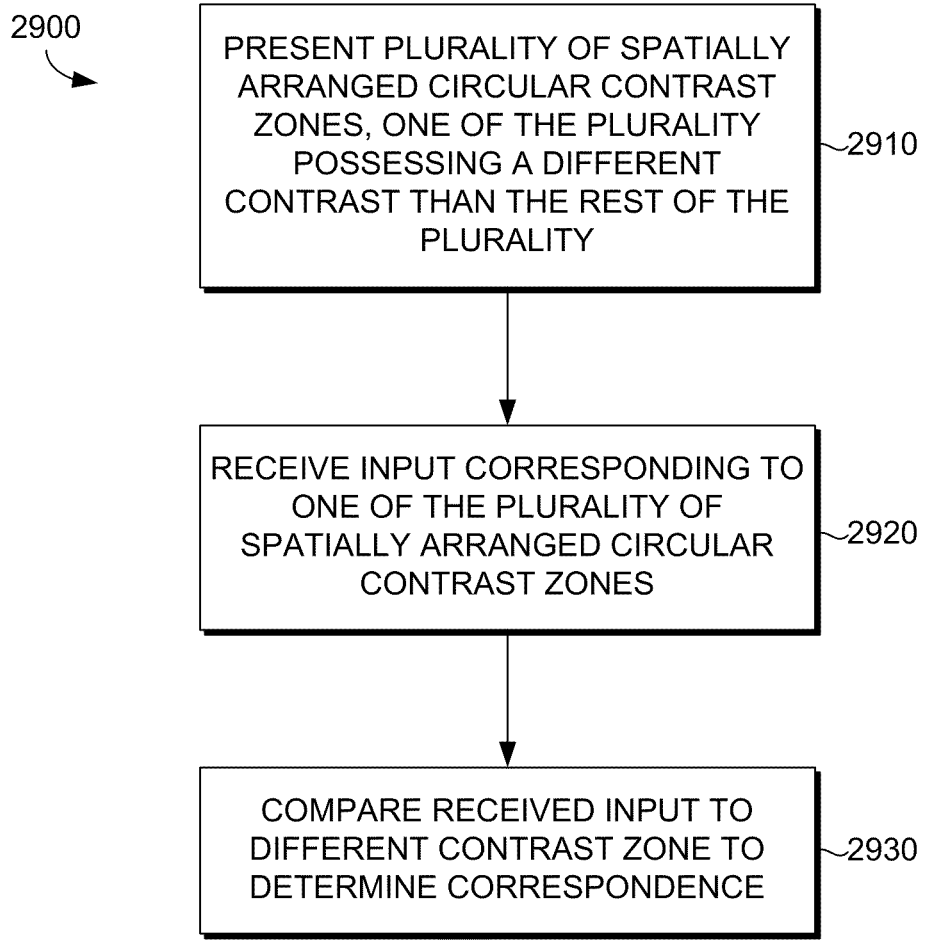
FIG. 29 illustrates a method for testing and/or training contrast sensitivity in accordance with the present invention.

Referring now to FIG. 29, a method 2900 for testing and/or training contrast sensitivity in accordance with the present invention is illustrated. In step 2910 a plurality of spatially arranged circular contrast zones are presented to a subject, one of the plurality of circular contrast zones possessing a different contrast then the rest of the plurality. In step 2920, an input is received from a subject corresponding to one of the plurality of spatially arranged circular contrast zones. In step 2930, the received input is compared to the circular contrast zone having a different contrast pattern to determine the correspondence between the input and the differing circular contrast zone. Step 2930 effectively determines whether the subject correctly perceived the presented plurality of circular contrast zones.

Figure 30:
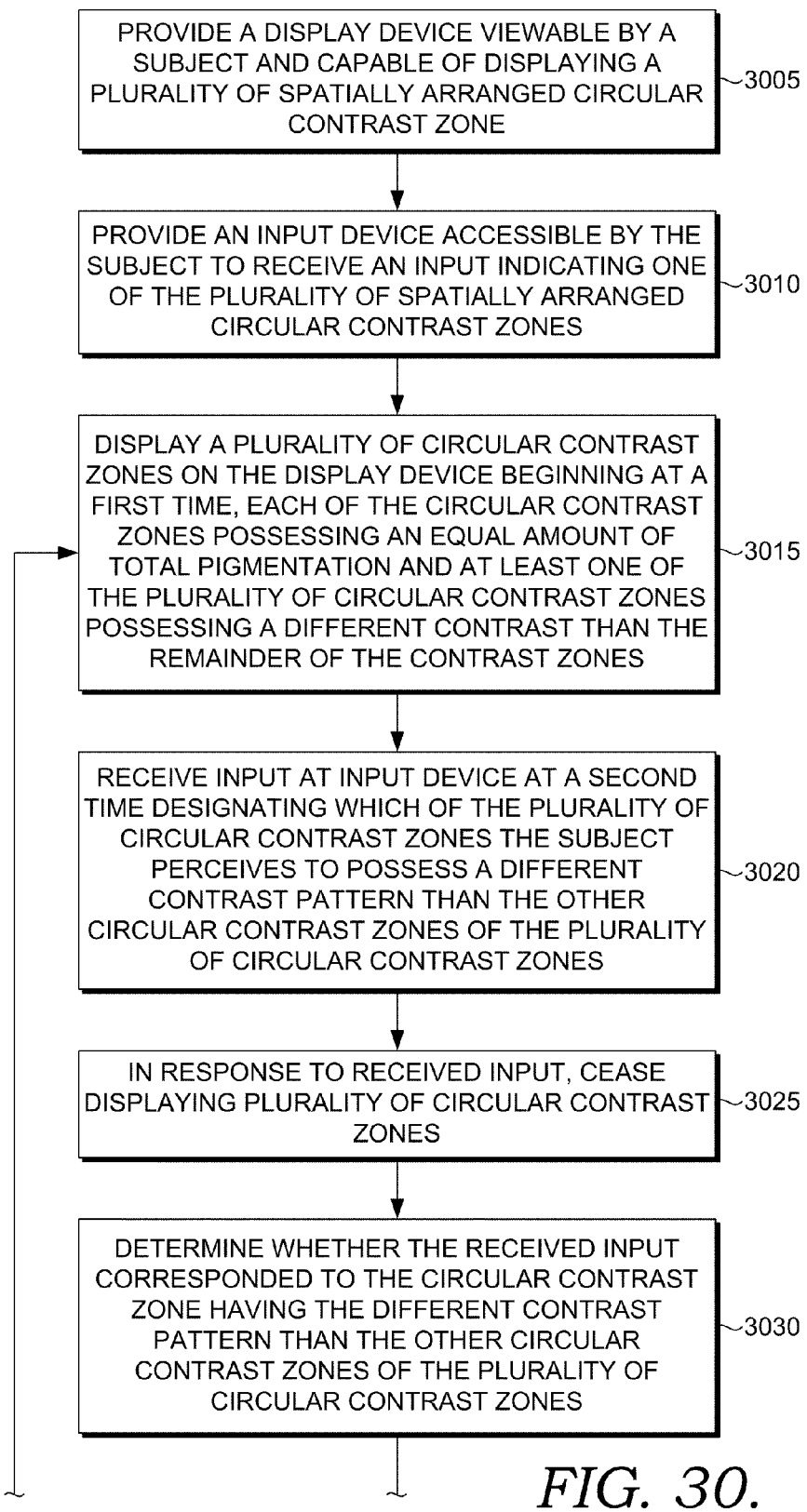
FIG. 30 illustrates a further method for testing and/or training contrast sensitivity in accordance with the present invention.
Figure 30:
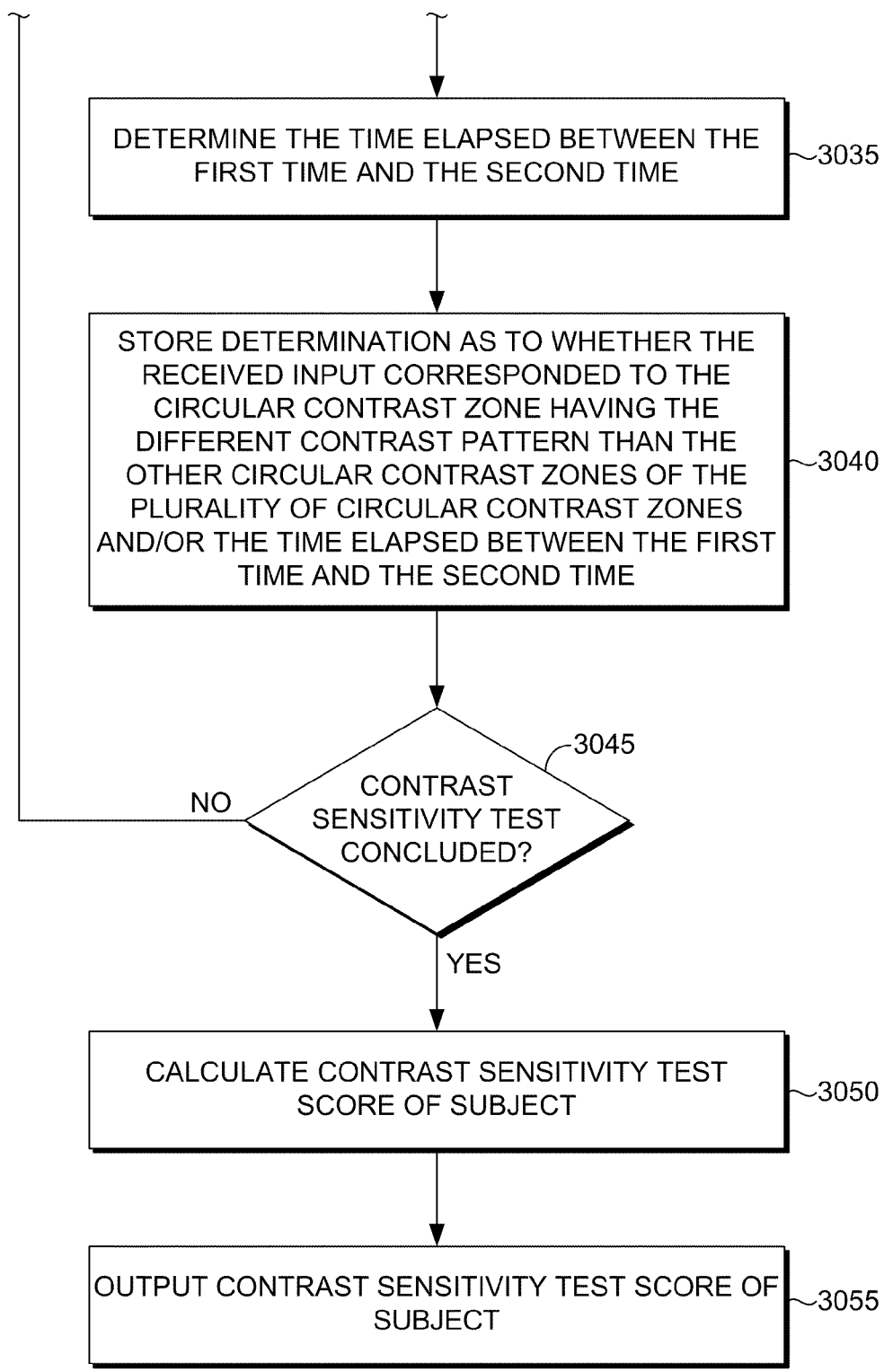

Referring now to FIG. 30, a further method 3000 for testing or training the contrast sensitivity of a subject is illustrated. In step 3005 a display device is provided that is viewable by a subject and capable of displaying a plurality of spatially arranged circular contrast zones. In step 3010, an input device is provided that is accessible by the subject to receive an input from the subject indicating one of the plurality of spatially arranged circular contrast zones. For example, the input device provided may be capable of receiving any of a plurality of inputs, each of the inputs corresponding in a spatial fashion to one of the plurality of circular contrast zones via display device provided in step 3005 is capable of displaying.

In step 3015, a plurality of circular contrast zones are displayed on the display device beginning at a first time, each of the circular contrast zones possessing an equal amount of total luminance and at least one of the plurality of circular contrast zones possessing a different contrast than the remainder of the contrast zones. For example, in step 3015 a testing unit may cause the display device to display a top contrast zone, a right contrast zone, a bottom contrast zone, and a left contrast zone, with one of the contrast zones differing in its total contrast from the other contrast zones by having higher contrast than the other zones. For example, one contrast zone may possess a non-zero contrast, while the other contrast zones may possess zero contrast. Of course, more than one, or even all, of the contrast zones may have a non-zero contrast zone, with one contrast having a higher contrast than the other contrast zones. In step 3020, an input is received at the input device at a second time after the first time, the input designating which of the plurality of circular contrast zones the subject perceives to possess a different contrast pattern than the other circular contrast zones of the plurality of circular contrast zones displayed in step 3015. Any manner of input may be used in conjunction with step 3020. In step 3025, in response to receiving an input step 3020, the displaying of the plurality of circular contrast zones ceases.

In step 3030, it is determined whether the received input corresponded to the circular contrast zone having the different contrast pattern than the other circular contrast zones of the plurality of circular contrast zones. Step 3030 provides a measure of the accuracy of the subject's contrast sensitivity. In step 3035, the time elapsed from the first time at which the plurality of circular contrast zones are first displayed and the second time at which an input is received is determined. Step 3035 provides a measure of the speed of the subject's contrast sensitivity. In step 3040, a determination is stored as to whether the received input corresponded to the circular contrast zone having the different contrast pattern than the other circular contrast zones. Step 3040 may additionally/alternatively store a measure of the time elapsed between the first time and the second time. The measures of accuracy and/or speed stored in step 3040 may be useful in both testing and training the contrast sensitivity of a subject.

In step 3045, a determination may be made as to whether the contrast sensitivity testing and/or training session has been concluded. The result of the determination of 3045 may be based upon any of a number of possible considerations. For example, the contrast sensitivity testing and/or training session may be designed to operate for predetermined number of iterations, possibly each at a different contrast differential between the one circular contrast zone having a different contrast than the other contrast zones. In such an example, the conclusion of step 3045 would be that the contrast sensitivity test/training session is not completed until it has been iterated the predetermined number of times. Alternatively, a contrast sensitivity testing and/or training session may be designed such that it increases in difficulty until the subject incorrectly identifies the circular contrast zone having a different contrast a certain number of times, which may be one or more. In this additional example, the determination of step 3045 would be based upon the accuracy of the input received in step 3020 and the determination of step 3030, possible in conjunction with prior iterations of these steps. A "stair step" methodology may alternatively be used whereby the first iteration presents a high contrast circular contrast zone, the next iteration(s) decreases the contrast a "full" step until an incorrect response is made, after an incorrect response is made contrast is increased a "half" step, and thereafter decreased by a "quarter" step is a correct response is received and increased by a "quarter" step if an incorrect response is received, and so on until a contrast difference just perceivable to a subject is identified. Of course, the size of a "step" may vary. in a "step" may vary. Any number of variations may be used in step 3045 to determine whether the contrast sensitivity test has concluded. If the result of step 3045 is a determination that the contrast sensitivity test has not concluded, method 3000 returns to step 3015 of displaying a plurality of circular contrast zones. The iteration of steps 3015 through 3040 may utilize different contrast patterns, and even different arrangements of circular contrast zones, possibly having different total numbers, than prior iterations, but need not. If the conclusion of step 3045 is that the contrast sensitivity testing and/or training has concluded, method 3000 may proceed to step 3050.

In step 3050, a contrast sensitivity assessment score of the subject may be calculated. The contrast sensitivity assessment score calculated in step 3050 may simply comprise the number of correct responses of a subject, or may be more complicated. Such an assessment score may account for the degree of contrast of the circular contrast zones during the test, the time elapsed between time one and time two, and any other factors.

In step 3055, the contrast sensitivity assessment score for the subject may be output. Step 3055 may output the assessment score directly to the subject of the test, to a trainer, a medical specialist, a vision specialist, other individual, data base, storage device, etc.

Depth Perception Testing and/or Training

Depth perception testing and or training include providing a subject one or more indicia that are perceived to have a difference in depth. For example, eye covering liquid crystal displays ("LCD") may provide a flicker effect such that when a first LCD covering a first eye is activated (may either obscure or be translucent) and a second LCD covering a second eye is not activated (opposite effect of the first LCD), this is referred to as shutter glasses for ease of discussion herein. This flicker effect ensures that each eye is only able to receive visual information of a displayed indicia at alternating times. Therefore, when the first eye is able to view an indicia, the second eye has an obscured view of the indicia. In an exemplary embodiment, a display screen that presents the indicia is synchronized with the shutter glasses so that a first indicia may be shown to the first eye and a second indicia may be shown to the second eye. This ability allows for one or more indicia that are displayed to be perceived as having depth. Additional methods are contemplated herein for achieving a similar effect. For example, as previously discussed, three-dimensional eyewear, such as anaglyphic type glasses may also be employed to achieve a similar experience.

Referring back to FIG. 10C, an exemplary embodiment of the present invention includes the user 190 positioned a defined distance from the second display 130. The second display is functional to present a plurality of indicia, such as the four indicia 1030-1033. The subject 190 provides an input indicating which of the four indicia are perceived to have depth (or the greatest or least amount of depth). In an exemplary embodiment, the indicia intended to be indicated by the subject's input may be located at a systematic or random location. For example, defined location may exists for presenting indicia, but none of the defined locations are the exclusive location for providing an indicia that is to be identified. Therefore, all indicia may be presented in a known location, but the indicia to be identified may rotate among those known locations. In yet another exemplary embodiment, the locations of displayed indicia may change in a random or pseudo random manner.

As previously discussed with respect to other testing and/or training activities, timing of a displayed indicia as well as timing in which an input is valid may be constant, variable, or randomized. Additionally, the timing may be systematically changed to provide an additional variable within the framework of testing or training depth perception.

Additionally, it is contemplated that the difference in perceived depth between an indicia that is to be indicated by a subject and the perceived depth of remaining indicia simultaneously presented may vary. For example, a large discrepancy in the perceived depth of the indicia may be provided to a subject initially, but the discrepancy may be methodically changed based, in part, to the subject's progression or ability. Therefore, the indicia displayed to the subject may adapt to one or more factors. Further, timing for displaying the indicia or receiving an input may also change as a result of one or more of the factors.

Near-Far Focus Testing and/or Training

Systems and methods in accordance with the present invention may be used to test and/or train the visual abilities of a subject in changing the subject's focus from near to far and from far to near. Systems and methods in accordance with the invention may utilize at least one near display device and at least one far display device. A far display device may be located at or near optical infinity from a subject. A near display device may be located at differing distances from a subject, ranging from a few inches to several feet. Additionally, multiple display devices at multiple distances may be used, such as a near display device, a far display device, and a mid-range display device located between the near display device and the far display device. Also, multiple near display devices and/or multiple far display devices may be used. Further, display devices may be located in differing directions from a subject. For example, the angle of vision of display devices may differ, with some to the left of a subject's line of vision and some to the right of a subject's line of vision. Display devices may also be positioned higher or lower than the subject's normal line of vision. One skilled in the art will appreciate that different positioning of display devices may be suitable for testing and/or training individuals for particular activities. For example, a baseball shortstop might have to quickly shift visual focus from a batter striking a pitched ball (essentially at optical infinity) to a position towards the ground at approximately the shortstop's knees to field a ground ball. For this reason, visual testing and/or training of an individual playing shortstop might focus on the individual's abilities to focus visually in those two positions. The various aspects of systems and methods in accordance with the present invention are described more fully in association with the attached figures.

Figure 31:
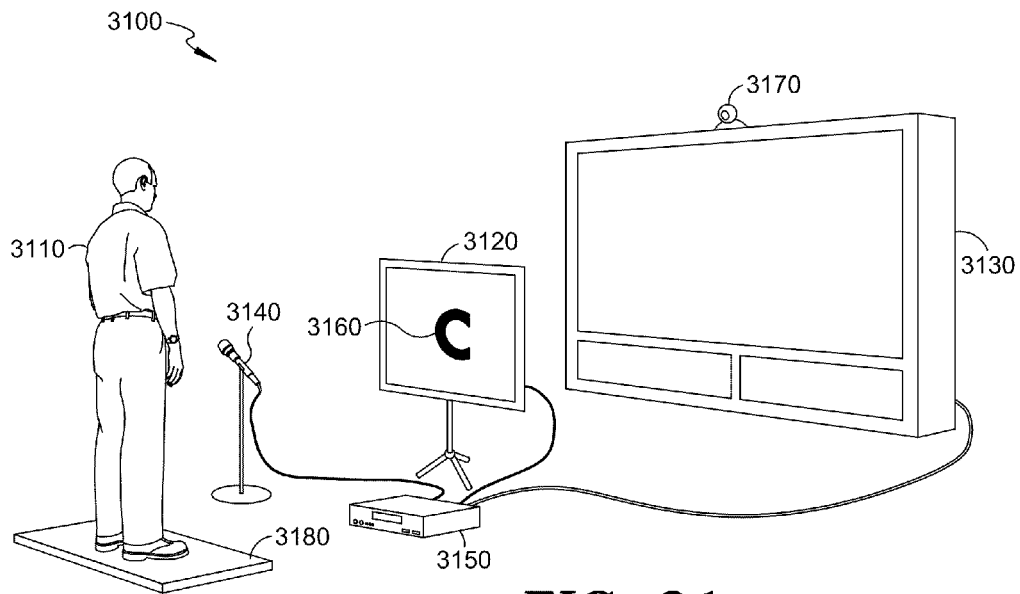
FIG. 31 is an illustration of a system for near-far focus testing and/or training in accordance with the present invention.

Referring now to FIG. 31, a system 3100 for testing and/or training the near and far visual abilities of a subject is illustrated. A first display device may comprise a multi-touch device 3120 (also referred to as the near display device) may be located visually near to subject 3110. A second display device 3130 may be located visually far from subject 3110. Second display device 3130, alternatively referred to as the far display device 3130 or distant display device 3130, may be located at or near optical infinity relative to subject 3110. Multi-touch device may receive inputs from subject 3110 in response to visual indicia displayed on multi-touch device 3120 and/or far display device 3130. A control unit 3150 may connect to near display device 3120 and far display device 3130.

As illustrated in FIG. 31, an indicia 3160 may be displayed on near display device 3120. As illustrated in FIG. 31, indicia 3160 comprises a Landolt C. As illustrated in FIG. 31, the Landolt C of indicia 3160 is oriented to the right as viewed by subject 3110. Subject may respond to indicia 3110 by stroking multi-touch device to the right.

Figure 32:
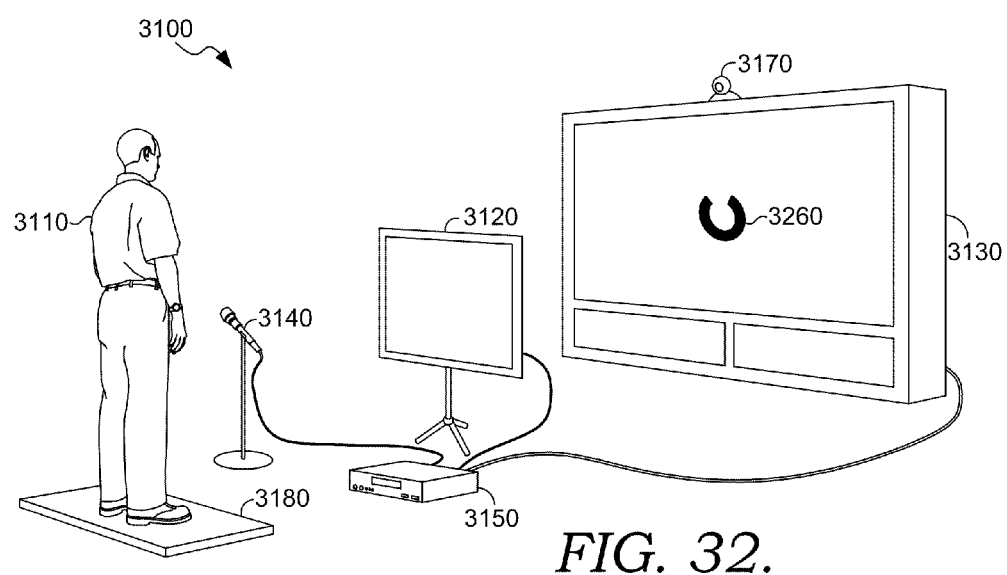
FIG. 32 further illustrates a system for near-far focus testing and/or training in accordance with the present invention.

Referring now to FIG. 32, system 3100 is illustrated with indicia 3160 removed from near display device 3120. For example, subject 3110 may have correctly identified the indicia 3160 displayed in FIG. 31 as oriented to the right, by example by stroking multi-touch device to the right. Upon receiving a correct input, or alternatively upon receiving an incorrect input or receiving no input during a pre-determined amount of time, control unit 3150 may remove the display of an indicia upon near display device 3120 and commence the display of an indicia 3260 on far display device 3130. In the example illustrated in FIG. 32, indicia 3260 is a Landolt C, this time with an upwards orientation. Subject may respond to indicia 3260 by stroking multi-touch device upward. Of course, the orientation of the Landolt C shown as indicia 3260 may vary from that shown and described herein. Indicia other than Landolt C's, as illustrated in FIG. 31 and FIG. 32, may be used in accordance with the present invention. For example, numerals, letters, pictures, photographs, or other types of indicia that may be recognized by a subject 3110 may be utilized.

Figure 33A:
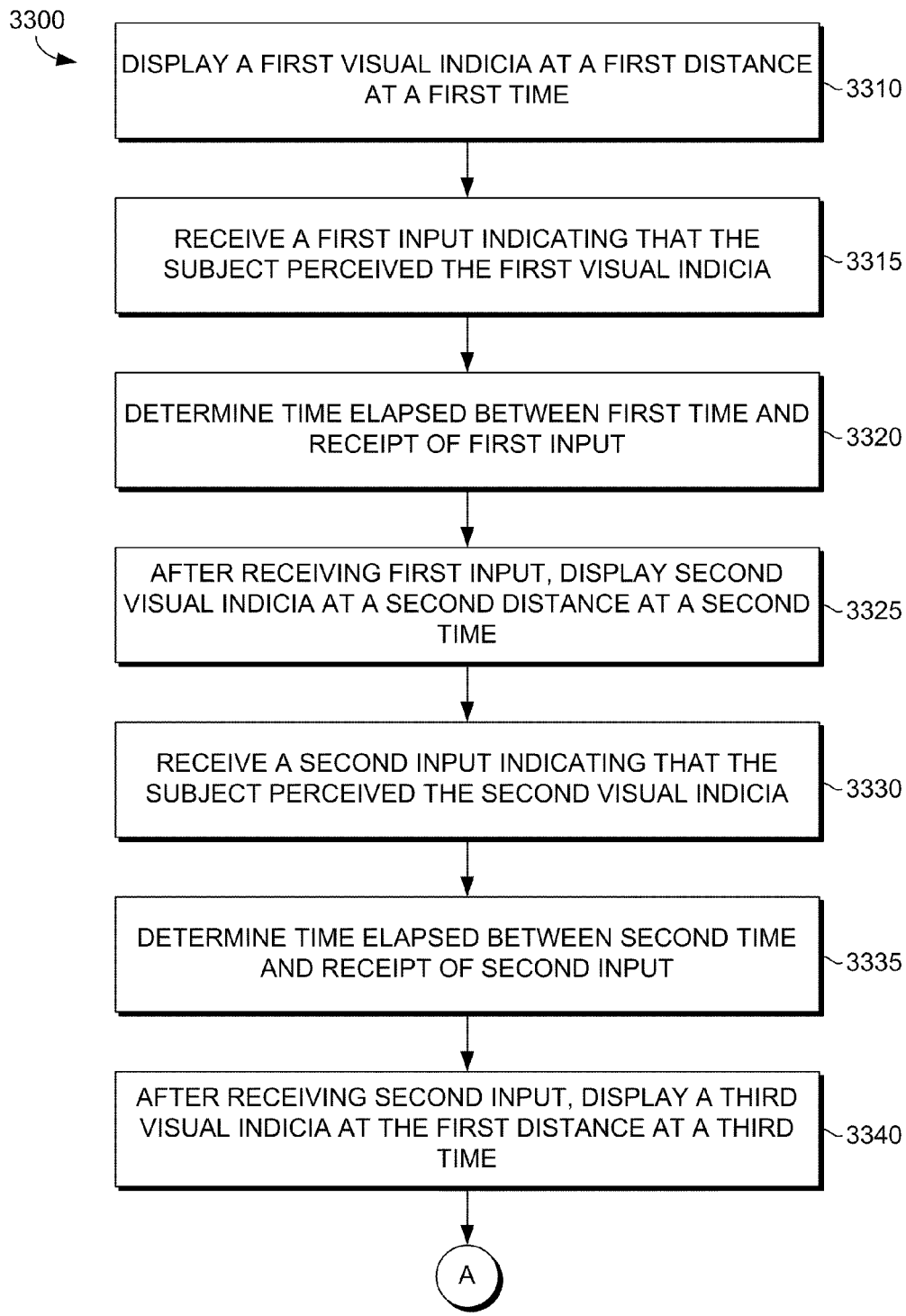
FIGS. 33A and 33B illustrate a method for near-far focus testing and/or training in accordance with the present invention.
Figure 33B:
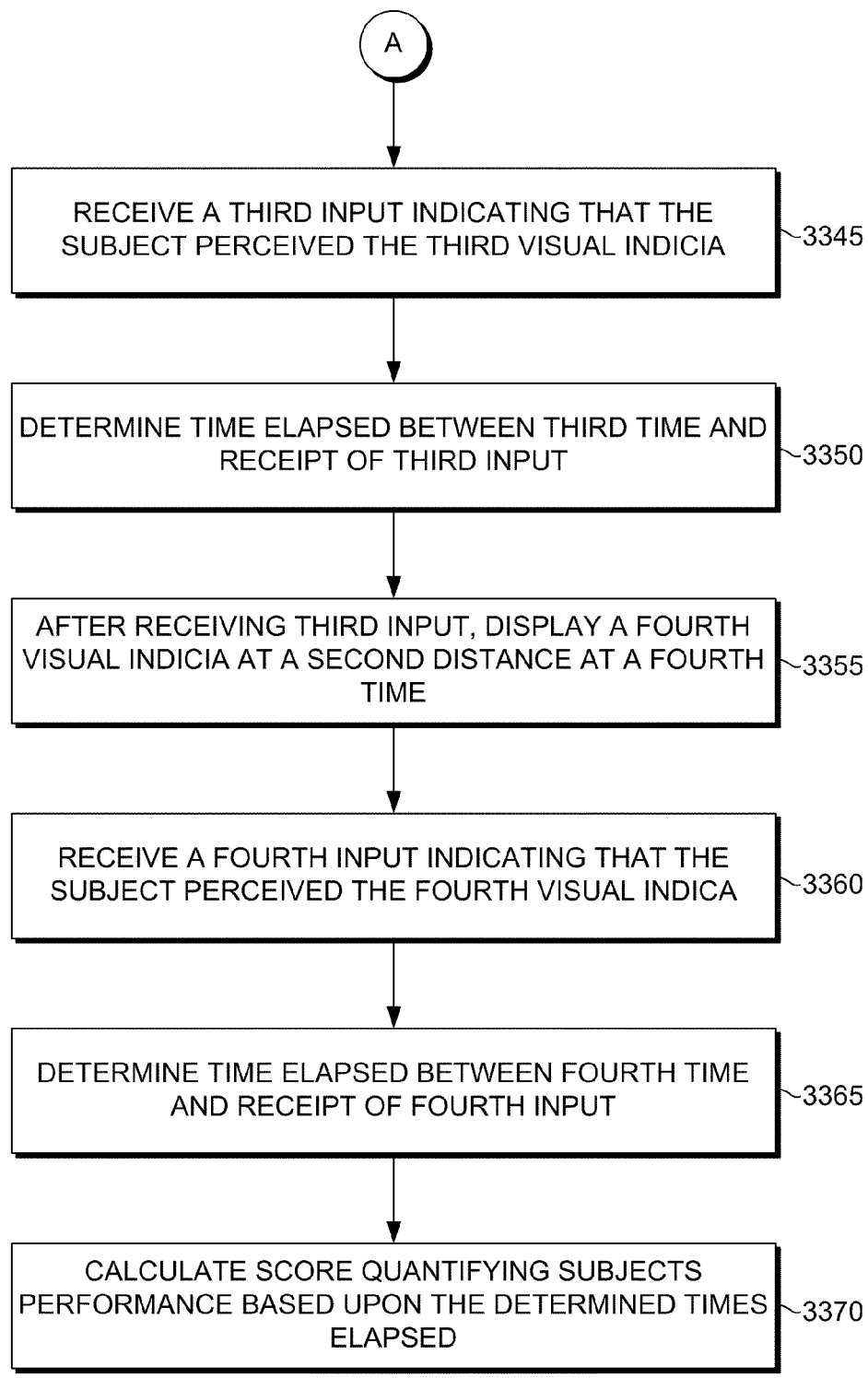

Referring now to FIG. 33A and FIG. 33B, a method 3300 in accordance with the present invention is illustrated. In step 3310 a first visual indicia may be displayed at a first distance at a first time. For example, step 3310 may display a visual indicia on a near display device at a first time.

In step 3315 a first input may be received indicating that the subject perceived the first visual indicia. Step 3315 may, for example, utilize a multi-touch device coupled to control unit to detect an input from a subject. The input may, for example, identify a characteristic possessed by a displayed indicia, such as the orientation of a Landolt C.

In step 3320 the time elapsed between the first time at which the indicia was displayed and the receipt of the first input may be determined. Step 3320 may be appropriately performed by a control unit that controls the display of the first visual indicia in step 3310 and that operates in conjunction with a microphone to receive the first input in step 3315.

In step 3325, after receiving the first input a second visual indicia may be displayed at a second distance at a second time. For example, a visual indicia may be displayed at a far display device at a second time. In step 3330 a second input may be received indicating that the subject perceived the second visual indicia.

Step 3330 may resemble step 3315 in terms of the types of inputs that may be received and the manner in which the input may be received, although the characteristic, if any, identified for the displayed indicia may differ based upon the characteristic possessed by different displayed indicia.

In step 3335, the time elapsed between the second time at which the second visual indicia was displayed and the receipt of the second input may be determined. Step 3335, as with step 3320, may be appropriately performed by a control unit.

In step 3340, after receiving a second input a third visual indicia may be displayed at the first distance and at a third time. For example, step 3340 may display a third indicia on the near display device after a subject has responded in step 3330 to a displayed indicia on the far display device. In step 3345 a third input may be received indicating that the subject perceived the third visual indicia. Step 3345 may resemble step 3315. In step 3350, the time elapsed between the third time at which the third indicia was displayed and the receipt of the third input may be determined. Step 3350 may resemble step 3320.

In step 3355, after receiving the third input a fourth visual indicia may be displayed at a second distance and at a fourth time. For example, step 3355 may display a fourth visual indicia at the far display device after receiving an input responsive to the display of the third visual indicia on the near display device. Step 3355 may resemble step 3325. In step 3360, an input may be received indicating that the subject perceived the fourth visual indicia. Step 3360 may resemble step 3330. In step 3365 the time elapsed between the fourth time and the receipt of the fourth input may be determined. Step 3365 may resemble step 3335.

In step 3370 a score may be calculated quantifying the subject's performance based upon the determined times elapsed. Further iterations of displays of indicia and receipts of appropriate inputs, along with a determination of elapsed times, may be performed prior to step 3370. Step 3370 may indicate, for example, that a subject responds slowly to indicia displayed at a first distance but does not respond slowly to the display of indicia at a second distance, which would be indicative of a subject with focusing or vergence difficulties at the first distance but not at the second distance.

Figure 34A:
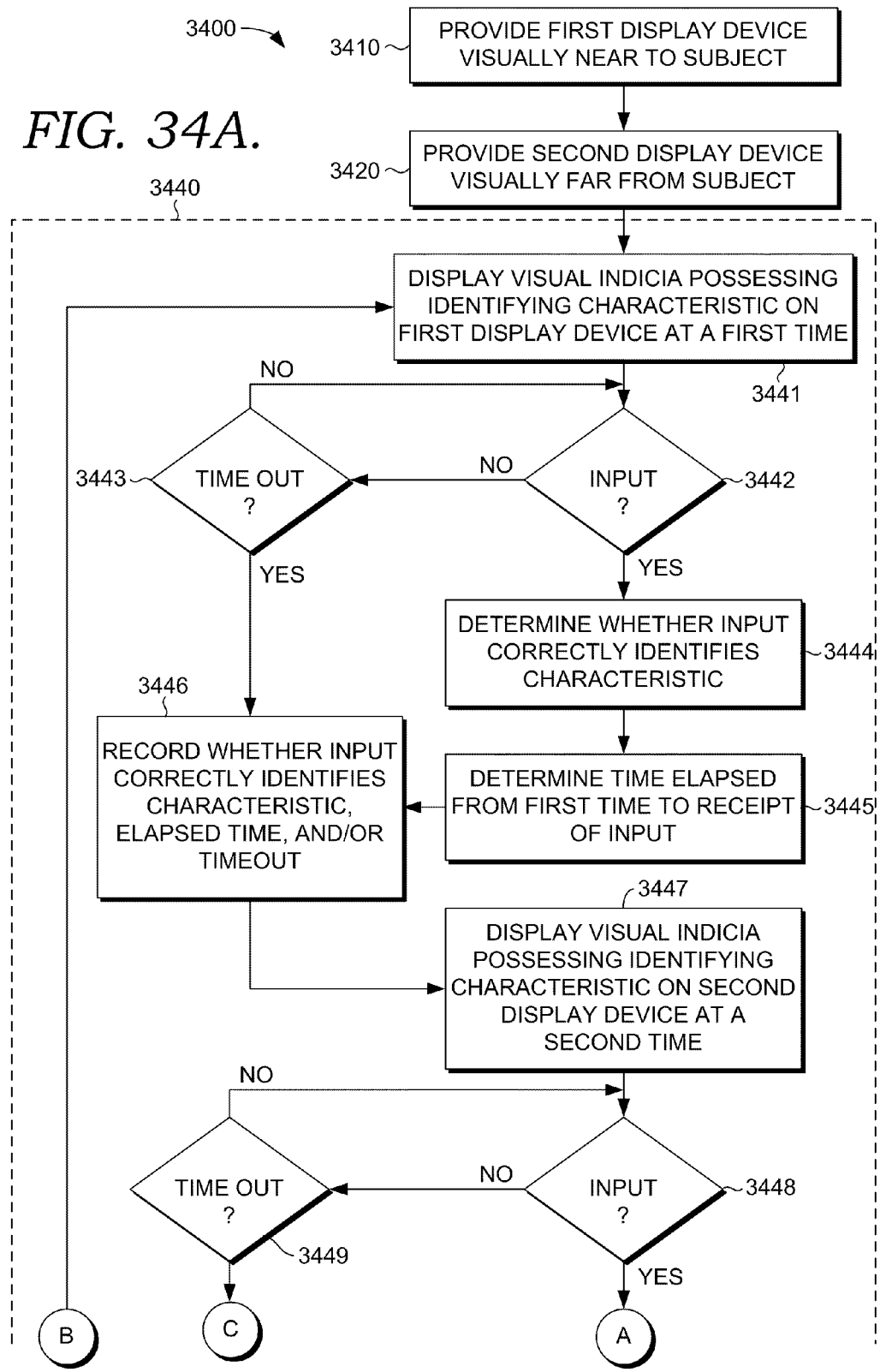
FIGS. 34A and 34B illustrate a further method for near-far focus testing and/or training in accordance with the present invention.
Figure 34B:
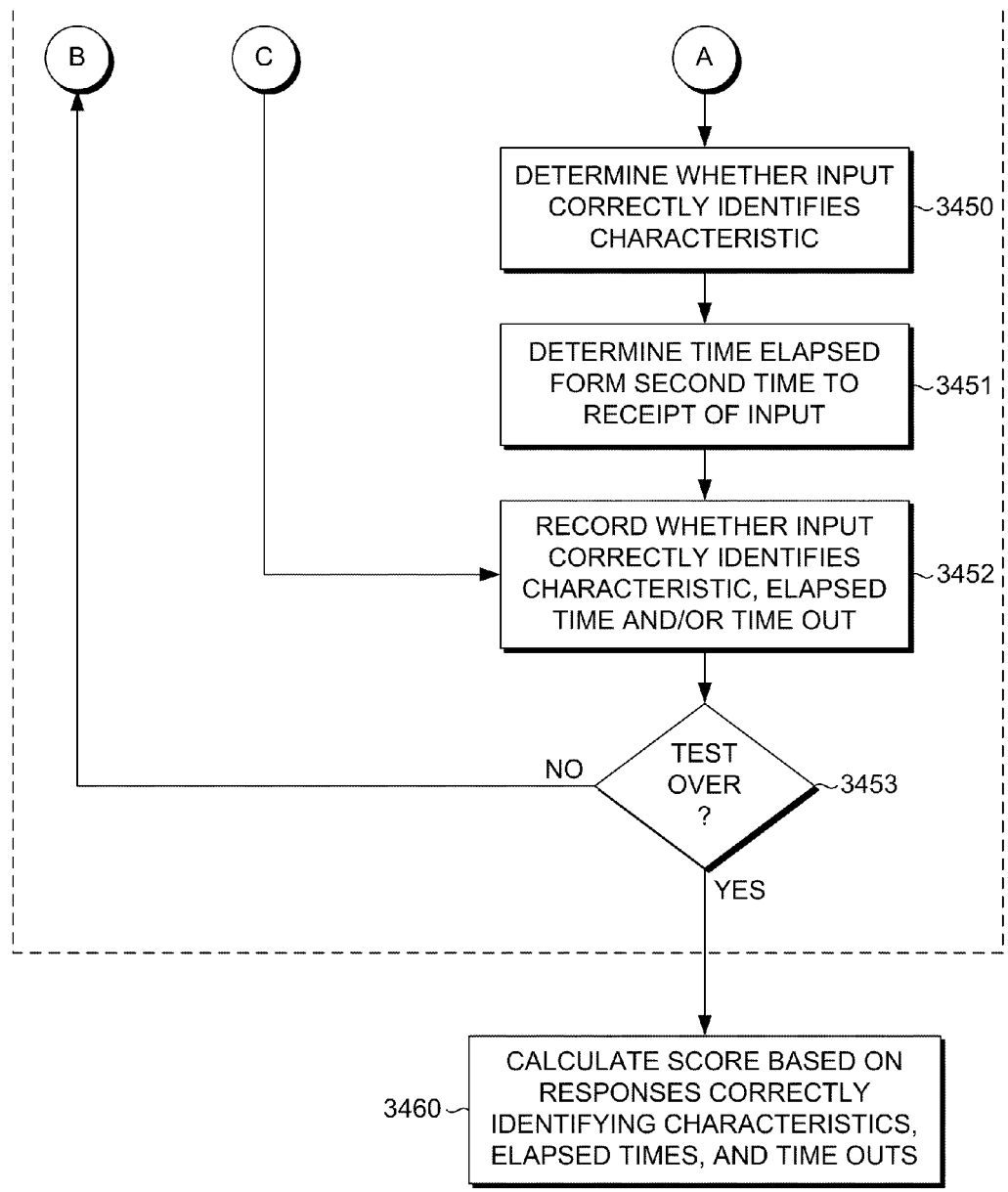
Figure 35A:
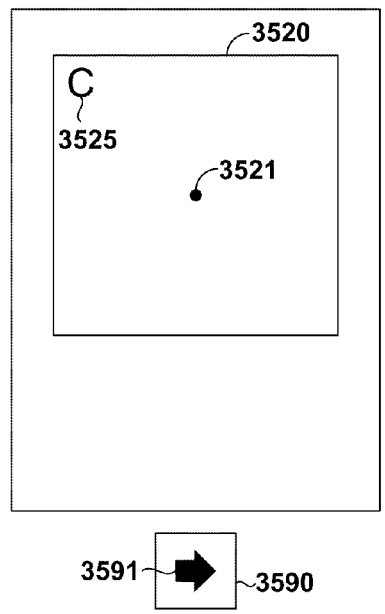
FIGS. 35A-35D illustrate an adaptable indicia used for testing and/or training target capture abilities in accordance with the present invention.
Figure 35B:
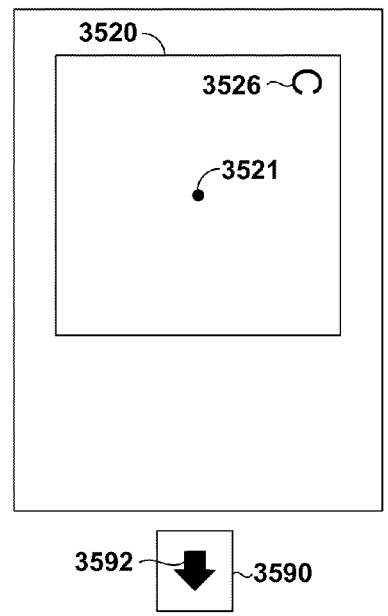
Figure 35C:
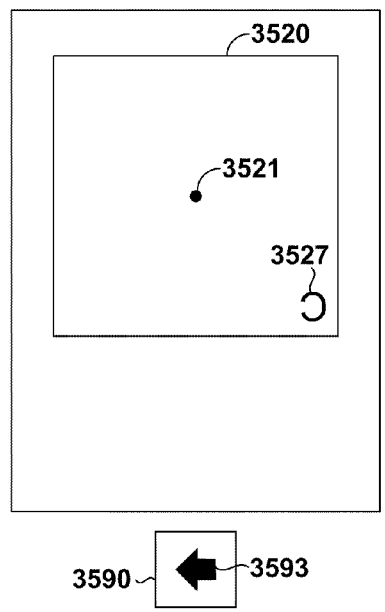
Figure 35D:
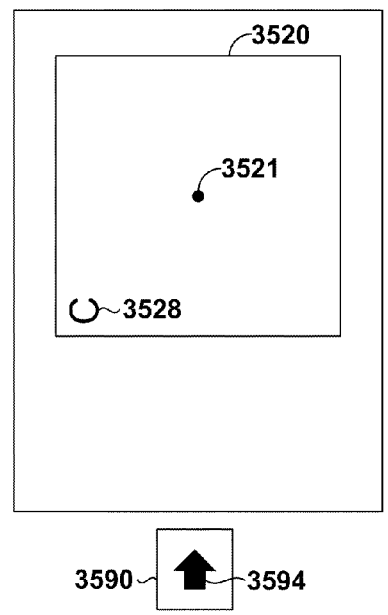

Referring now to FIGS. 34A and 34B, a further method 3400 in accordance with the present invention is illustrated. In step 3410 a first display device visually near to a subject may be provided. In step 3420 a second display device visually far from the subject may be provided. Step 3420 may provide a display device at or near optical infinity from a subject.

In testing and/or training step 3440, which may comprise a number of sub-steps, a visual indicia may be displayed on the display devices and inputs may be received until testing and/or training has concluded. In sub-step 3441 a visual indicia possessing an identifying characteristic may be displayed on the first display device at a first time. Sub-step 3442 determines whether an input has been received from a subject. Step 3442 may be performed, for example, by a control unit in conjunction with a multi-touch device that functions as both a near display device and an input device. If the result of sub-step 3442 is that no input has been received a timeout determination may be made in sub-step 3443. The timeout determination of sub-step 3443 may be made, for example, by a control unit. If no timeout has been reached in sub-step 3443, method 3400 may continue to wait for an input in sub-step 3442. If a timeout determination is made in sub-step 3443, method 3400 may proceed to sub-step 3446, which will be described subsequently. If in sub-step 3442 an input is received, method 3400 may proceed to sub-step 3444. Sub-step 3444 determines whether the input correctly identifies the characteristic of the displayed indicia. For example, the displayed indicia may have a given orientation that may be identified in the input.

Method 3400 may then proceed to sub-step 3445 to determine the time elapsed from the first time to receipt of the input in sub-step 3442. Method 3400 may then proceed to sub-step 3446, which may also be reached as a result of a timeout decision in sub-step 3443. In sub-step 3446 whether a input correctly identified a characteristic, the elapsed time prior to receiving the input, and/or whether a timeout occurred may be recorded. Sub-step 3446 may be performed, for example, by a control unit and may utilize an electronic recording media such as a hard drive, memory, removable storage such as a compact disk, a DVD, a floppy disk, printing to a physical media such as paper, or other type of recording device. Method 3400 may thereafter proceed to sub-step 3447 of displaying a visual indicia possessing an identifying characteristic on the visually far display device at a second time. Method 3400 may then proceed to sub-step 3448, which determines whether an input has been received. Sub-step 3448, like sub-step 3442, may be performed by a control unit in conjunction with a multi-touch device. If the conclusion of sub-step 3448 is that no input has been received, method 3400 may proceed to sub-step 3449 of determining whether a timeout has occurred. If no timeout has occurred, method 3400 may return to sub-step 3448 of determining whether an input has been received. Sub-step 3449 may, for example, be performed by a testing unit, as was sub-step 3443. If the result of sub-step 3448 was to determine that an input was received, method 3400 may proceed to sub-step 3450. Sub-step 3450 determines whether an input correctly identified the characteristic of the displayed indicia. Method 3400 may then proceed to sub-step 3451, which determines the time elapsed from the second time to the receipt of the input. Method 3400 may then proceed to sub-step 3452, which may also be reached if the conclusion of sub-step 3449 is that a timeout has occurred. Sub-step 3452 may record whether an input correctly identified the characteristic, record the elapsed time and/or record that a timeout occurred. As with sub-step 3446, sub-step 3452 may be performed by testing unit using any kind of recording media. Method 3400 may then proceed to sub-step 3453 to determine whether a test or training session has concluded. If the outcome of sub-step 3453 is that the testing and/or training is not over, method 3400 may return to sub-step 3441 and then the testing and/or training may continue. If the result of sub-step 3453 is the determination that the testing and/or training has concluded, step 3440 may conclude and method 3400 may proceed to step 3460, which calculates a score based on responses correctly identifying characteristics, the elapsed times, and timeouts. A score may particularly identify the performance of a subject at a given distance. One skilled in the art will further appreciate that method 3400 may utilize additional display devices at additional distances and directions from subject. In such an embodiment, additional sub-steps would be included in step 3440 for the display devices at additional distances.

Saccadic Target Capture Testing and/or Training

In an exemplary embodiment, a unified vision testing device may be functional for testing and/or training saccadic target capture abilities of a subject. Referring now to FIG. 35A-35D, target capture testing and/or training using adaptable indicia are illustrated. In the example illustrated in FIGS. 35A-35D, a display device 3520 displays a focal point 3521 at or near the center of display device 3520. A subject (not shown) may visually focus on focal point 3521 and, at a time while subject is engaged in viewing focal point 3521, an adaptable indicia may be displayed at some location of display device 3520, such as a corner. However, an indicia may be displayed at any location on display device and, in fact, the location of a displayed indicia may be an adaptable characteristic in accordance with the present invention, i.e., training and/or testing may develop the target capture abilities of an individual at varying distances from focal point 3521 and/or at different gaze angles on display device 3520. Generally speaking, subject (not shown) focusing on focal point 3521 will make a saccadic eye movement to visually acquire a displayed indicia and perceive a trait possessed by the indicia. In the examples illustrated in FIGS. 35A-35B, the indicia comprises a Landolt C possessing an orientation. The size of an indicia displayed for target capture testing and/or training may be based upon prior assessments of visual sensitivity determined using adaptable visual indicia as described herein, such as static visual acuity. Further, the examples illustrated in FIGS. 35A-35D utilize a multi-touch device 3590 as an input device. Multi-touch device 3590 may be swiped with a finger of subject (not shown) to indicate the direction of orientation of a displayed Landolt C. In the example illustrated in FIG. 35A, a first visual indicia 3525 has appeared in the upper left corner of display device 3520, and subject (not shown) has swiped multi-touch device 3590 to the right as indicated by arrow 3591. In the example illustrated in FIG. 35B, visual indicia 3526 comprises a Landolt C appearing in the upper right hand corner of display device 3520 and possessing a downward orientation, to which subject (not shown) responds by swiping multi-touch device 3590 in a downward direction indicated by arrow 3592. In the example illustrated in FIG. 35C, a visual indicia 3527 has appeared in the lower right corner of display device 3520 and comprises a Landolt C with a leftward orientation, to which subject (not shown) responds using multi-touch 3590 by swiping to the left as indicated by arrow 3593. In the example illustrated in FIG. 35D, the visual indicia 3528 comprises a Landolt C in the lower left corner of display device 3520 and possessing an upward orientation, to which subject (not shown) responds using multi-touch device 3590 by swiping in an upward direction as indicated by arrow 3594. In the examples illustrated in FIGS. 35A-35D, the displayed visual indicia 3525, 3526, 3527, 3528, may possess characteristics that vary in different iterations of testing and/or training. For example, the duration of time during which a given indicia is displayed may vary, the distance and/or direction of the displayed indicia from focal point 3521 may vary, the color of an indicia may vary, the contrast of an indicia trait background may vary, the size of the indicia may vary, or any other visual characteristic of a displayed indicia either alone or in conjunction with its visual background may be varied.

Figure 36:
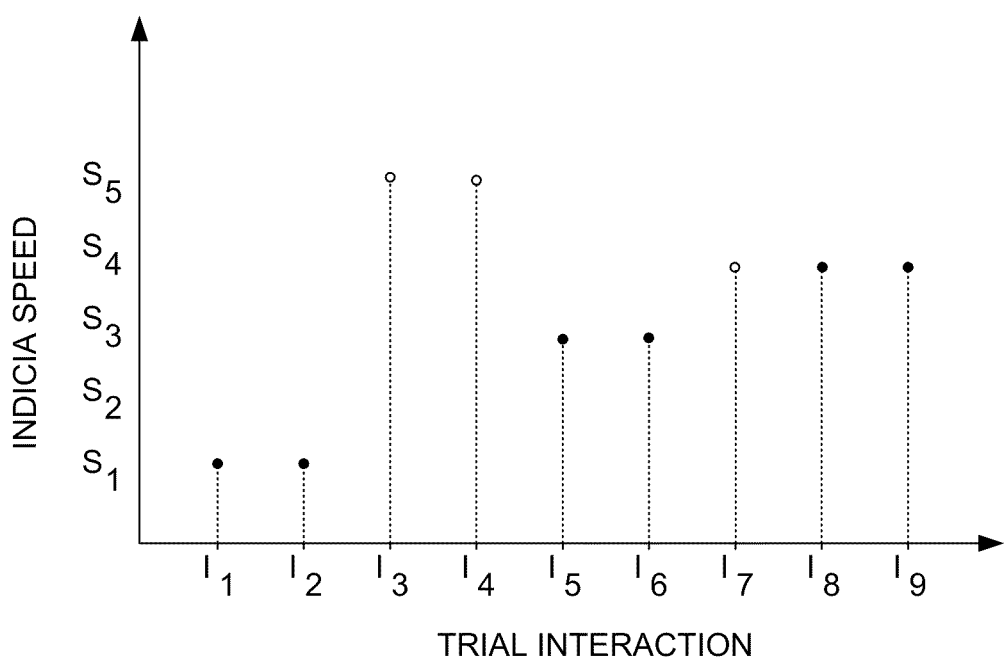
FIG. 36 illustrates the change in speed of a dynamic visual indicia over multiple iterations in accordance with the present invention.

Referring now to FIG. 36, indicia speed for different trial iterations is illustrated. In FIG. 36, a solid dot indicates a correct input corresponding to a displayed indicia trait, while an open/empty dot/circle indicates either an incorrect response not corresponding to a displayed indicia trait or no response. In the example illustrated in FIG. 36, a plurality of trials are illustrated. In the example illustrated in FIG. 36, indicia moved at one of five speeds, denoted from slowest to fastest as $S_1$, $S_2$, $S_3$, $S_4$, and $S_5$. In this example, trial iteration $I_1$ involved an indicia moving $S_1$ and, as indicated by the solid dot, a subject provided a correct input in response to the displayed indicia. As further illustrated in the example of FIG. 36, a second iteration denoted $I_2$ involved an indicia moving at the first speed denoted $S_1$. Iteration $I_2$ resulted in a correct response from subject, as denoted by the solid dot. In the example of FIG. 36, iteration $I_3$ occurred at speed $S_5$ and resulted in either an incorrect response from subject or no response from subject, as indicated by the open dot. In the example illustrated in FIG. 36, iteration $I_4$ occurred at speed $S_5$, which also resulted in either an incorrect response from subject or no response from subject, as indicated by the open dot. Thereafter in this example, subject provided an accurate response to iteration $I_5$ and $I_6$ at a speed $S_3$, an incorrect or no response for iteration $I_7$ at speed $S_4$, and two consecutive correct responses to iteration $I_8$ and $I_9$ at speed $S_4$. The dynamic visual acuity test illustrated as an example in FIG. 36 could proceed further after iteration $I_9$, but could also be determined to be concluded, with the dynamic visual acuity of a subject being measured as capable of resolving traits of indicia move at speed $S_4$.

Visual Perception Span Testing and/or Training

The visual perception span of an individual may be tested and/or trained using systems and/or methods to present one or more two-dimensional representations to the individual, receive inputs from the individual based upon the individual's perception of the one or more two-dimensional representations, and process the received input(s). Visual perception span testing and/or training may be configurable so that the assessments administered may vary based on the needs of the individual. The received input may then, for example, be used to compute data related to the individual's visual perception span, both overall and for each individual assessment. Further, the visual perception speed of an individual may be tested and/or trained by determining how quickly an individual can perceive one or more two-dimensional representations.

Figure 37:
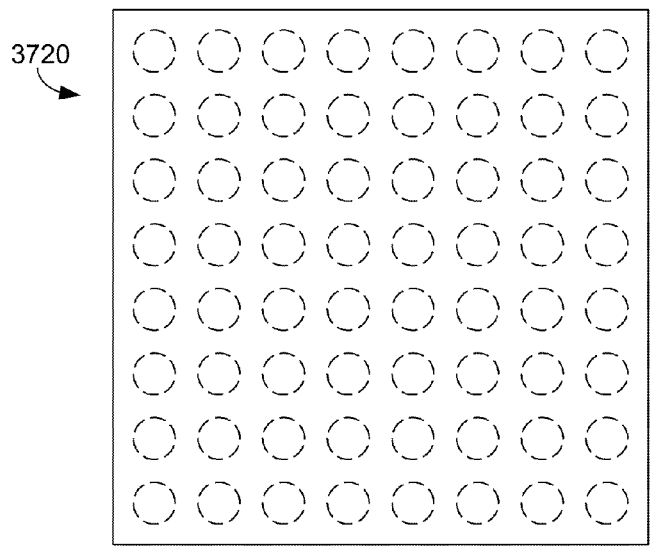
FIG. 37 illustrates a display device that provides visual information in accordance with an embodiment of the present invention.

Referring now to FIG. 37, second display device 3720, which in this example comprises a touch-sensitive screen is further illustrated in accordance with an embodiment of the present invention. Second display device 3720 may comprise a plurality of output portions 3725. Portions 3725 presented in FIG. 37 are shown in an inactive state. Output portions 3725 may be portions of a screen with the ability to indicate a distinction between an active state and an alternative state, such as an inactive state. Output portions 3725 of second display device 3720 may be arranged in a two-dimensional representation. Output portions 3725 may also or alternatively comprise more than one color, wherein the more than one color of output portions may be used to distinguish between active and inactive states. The activation status of output portions 3725 of display device may determine, the amount of information provided to a subject by second display device 3720, and the duration of the activation of output portions 3725 of second display device 3720 may determine the time available for a subject to perceive information displayed. As presented in FIG. 37, each output portion 3725 is in an "inactive" state.

Figure 38:
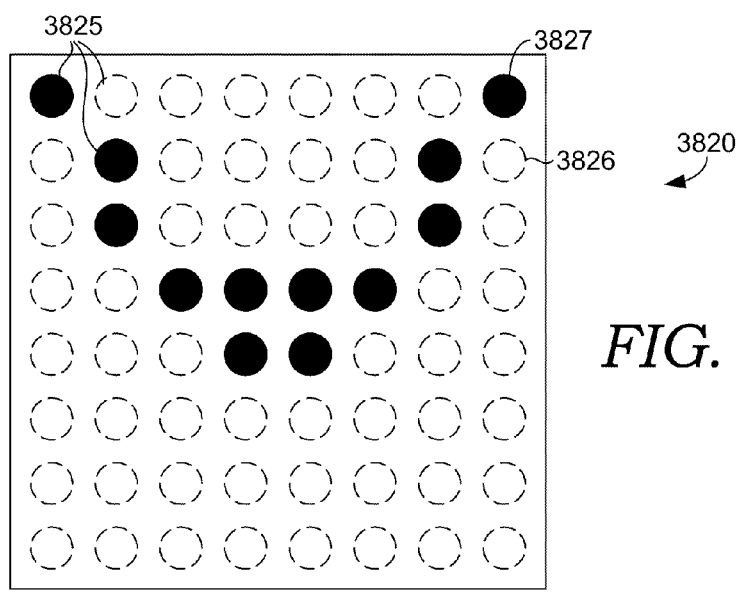
FIG. 38 illustrates another display device that provides visual information in accordance with an embodiment of the present invention.

Referring to FIG. 38, second display device 3820 is further illustrated in accordance with an embodiment of the present invention. Second display device 3820 illustrates a distinction between active output portions 3827 and inactive output portions 3826. In addition to active output portions 3827, inactive output portions 3826 are represented as comprising the rest of the grid on display device 3820, wherein inactive output portions 3826 may be represented by their empty characteristic.

Figure 39:
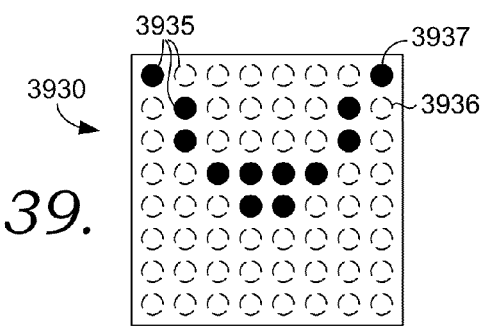
FIG. 39 illustrates another input device that receives inputs in response to visual information in accordance with an embodiment of the present invention.

FIG. 39 illustrates second display device while used to input a response from subject after the display of two-dimensional visual information has ceased. Input device 3930 and display device 3820 may comprise a single touch-sensitive screen. As shown in FIG. 39, input device 3930 has been used to indicate a test subject's response inputs, for example, in response to the stimuli displayed on display device 3820. Input device 3930 may comprise input portions 3935, wherein input portions may be classified as active input portions 3936 and inactive input portions 3937. The input portions 3935 in FIG. 39 may be similar to the output portions 3725 as indicated in FIG. 37.

Figure 40:
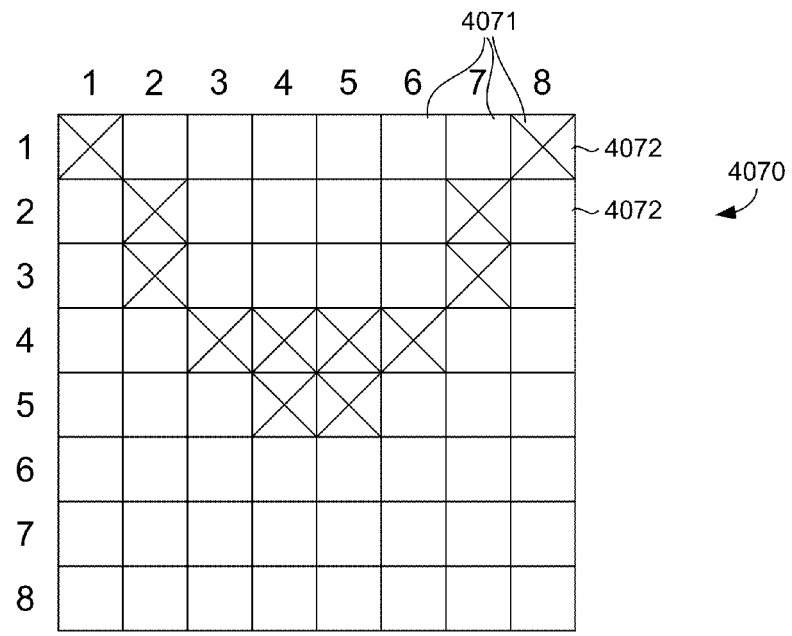
FIG. 40 depicts a visual perception span assessment in accordance with an embodiment of the present invention.

Referring to FIG. 40, a visual perception span and/or speed assessment 4070 is illustrated in accordance with an embodiment of the present invention. FIG. 40 depicts the accuracy of a subject's inputs in response to displayed visual information which may be used to test and/or train the visual perception span and/or the subject. FIG. 40 illustrates a collection of input squares 4071 that may have been used to indicate input portions selected by the subject. As seen in FIG. 40, blank input squares 4072 indicate areas where the subject did not enter an input. In contrast, non-blank input squares, such as square 4073, indicate areas where the subject did enter an input. As shown in FIG. 40, all non-blank input squares are indicated as correct input squares, similar to square 4073. Correct input squares may be marked with an "X" to indicate subject has entered an accurate input into an input device in response to one or more images presented on a display device. Such a visual characterization of a subject's result as illustrated in FIG. 40 may not be needed or desired as part of the testing and/or training of the visual perception span and/or speed of a subject, but is presented to facilitate the description of the present invention.

Figure 41:
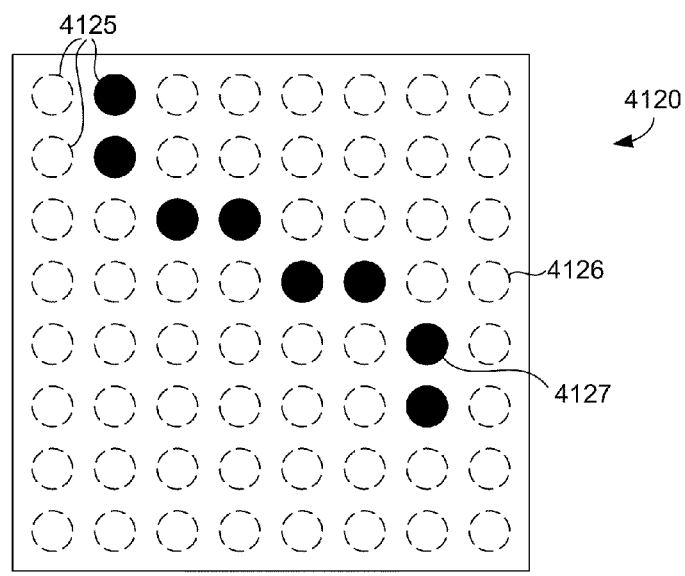
FIG. 41 illustrates a further display device that provides visual information in accordance with an embodiment of the present invention.

FIG. 41 depicts a further illustration of second display device 4120 in accordance with an embodiment of the present invention. Second display device 4120 may comprise a plurality of output portions 4125. Similar to FIG. 38, FIG. 41 further illustrates a distinction between active input portions 4127 and inactive output portions 4126. In distinguishing between output portions 4125, FIG. 41 illustrates a two-dimensional representation of active output portions 4127. In addition to active output portions 4127, inactive output portions 4126 are represented as comprising the rest of the grid on second display device 4120. In alternative embodiments, the distinctions between output portions need not be limited to binary characteristics, such as filled-in portions vs. empty portions. In alternative embodiments, output portions may be distinguished based on a number of factors across output portions. For example, four categories of output portions may be distinguished based on two characteristics such as those seen in cards: output portions that are red vs. output portions that are black, and an additional distinction between output portions that are diamonds, hearts, clubs and spades, the embodiment leaving open the possibility for examples such as red spades and black diamonds.

Figure 42:
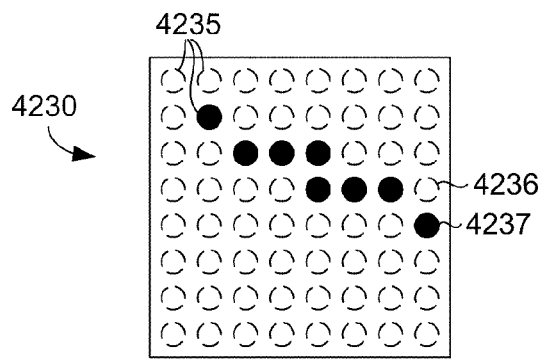
FIG. 42 illustrates an input device that receives inputs in response to visual information in accordance with a further embodiment of the present invention.

Input device 4230 illustrated in FIG. 42 shows exemplary responses by subject entered on touch-sensitive screen of second display device, such as those illustrated on display device 4120 in FIG. 41. Input device 4230 may comprise a plurality of input portions 4235. Similar to FIG. 38, FIG. 42 further illustrates a distinction between active input portions 4237 which have been touched by subject and inactive portions 4236. As shown in FIG. 42, input device 4230 reflects a test subject's inputs. When the two-dimensional input representation of FIG. 42 is compared against the two-dimensional output representation of FIG. 41, it is seen that the subject's responsive input as seen in FIG. 42 is of a different form than the two-dimensional display as shown in FIG. 41.

Figure 43:
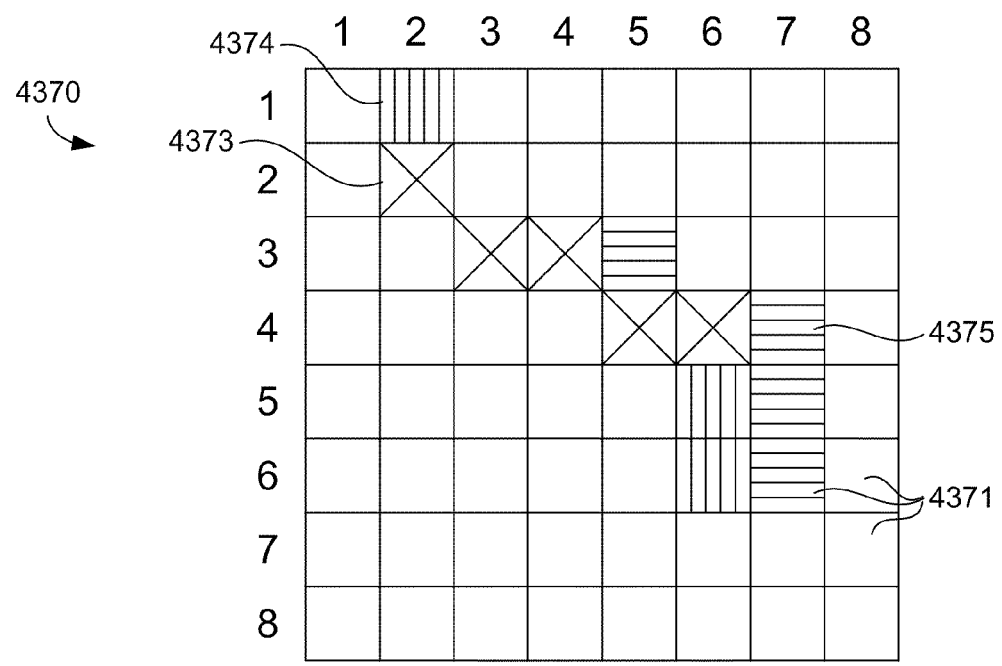
FIG. 43 depicts a representation of a visual perception span assessment in accordance with a further embodiment of the present invention.

FIG. 43 illustrates a visual perception span and/or speed assessment 4370 that compares the output depicted in FIG. 41 to the input depicted in FIG. 42 in accordance with an embodiment of the present invention. FIG. 43 is similar to FIG. 40 insofar as it also depicts a comparison of the inputs received from a subject in response to visual information displayed to a subject. In contrast to FIG. 40, however, FIG. 43 depicts a scenario wherein some of the responses input by the subject are incorrect in comparison to the visual information illustrated in FIG. 41. Similar to FIG. 40, FIG. 43 illustrates input squares 4371 that indicate areas where the subject did not enter an input in response to visual information displayed by a display device. FIG. 43 illustrates blank input squares, such as square 4372, and non-blank input squares, such as squares 4373, 4374 and 4375, that indicate areas where the subject did enter an input in response to visual information displayed by a display device or where the test subject failed to enter a response at a location corresponding to visual information displayed by a display device.

Non-blank squares are illustrated with different symbols to indicate whether the subject correctly registered an input. As shown in FIG. 43, some non-blank squares indicate a correct input, such as square 4373. Correct input squares are illustrated with an "X" to indicate that the subject entered an accurate input into an input device in response to visual information presented on a display device. As also shown in FIG. 43, some non-blank squares indicate incorrect input squares, such as squares 4374 and 4375. Incorrect input squares similar to square 4375 are shown with vertical lines to indicate the test subject failed to enter a response in that input portion corresponding to an active output portion on the second display device 4130. Incorrect input squares similar to square 4374 are shown with horizontal lines to indicate the subject entered an input on an input portion that did not correspond to an active output portion on the second display device. The illustration of FIG. 43 and the examples of indication markers as described above are examples only, and are not meant to limit the breadth of the invention. Further, a visual characterization of a subject's test result may not be needed or desired, and is illustrated to facilitate understanding of the present invention.

Figure 44:
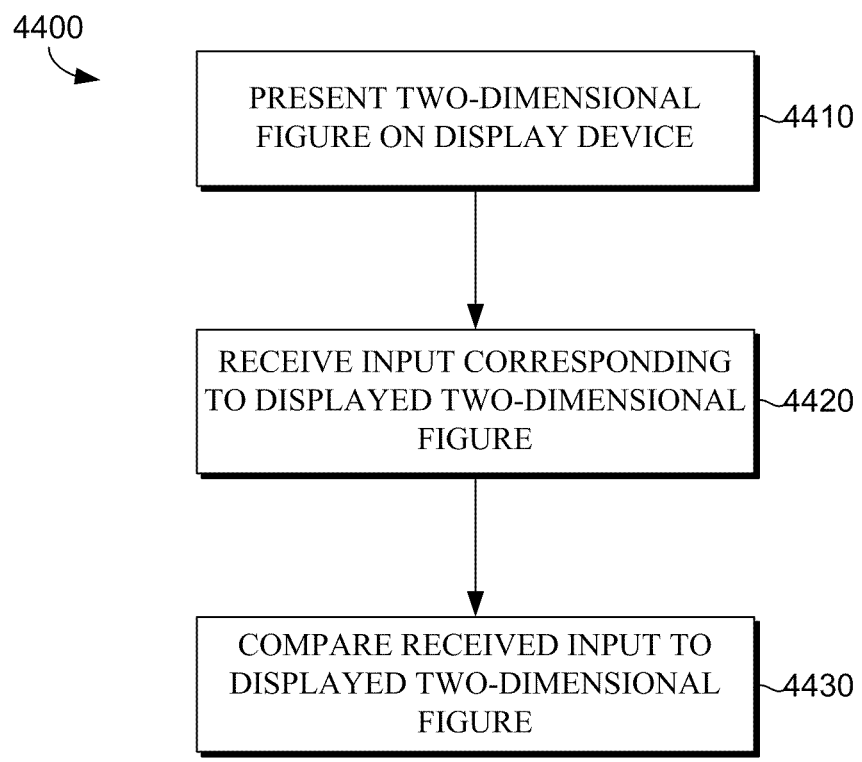
FIG. 44 illustrates a method for testing and/or training the visual perception span and/or speed of a subject in accordance with an embodiment of the present invention.

Referring now to FIG. 44, a method 4400 of testing and/or training the visual perception span and/or speed of a subject in accordance with an embodiment of the present invention. Although the terms "step" and "block" are used herein below to connote different portions of methods employed, the terms should not be interpreted as implying any particular order among or between various steps herein disclosed unless and except when the order of individual steps is explicitly described.

At step 4410, visual information comprising a two-dimensional figure is presented to a subject on a display device. At step 4420, the responsive input corresponding to the displayed two-dimensional figure may then be received by an input device. In embodiments, a single touch-sensitive screen may be used as both a display device and an input device. At step 4430, a processing component may then compare the received input with the displayed two-dimensional figure. The steps of method 4400 may be performed, for example, by a computing device such as control unit 120 shown in FIG. 1A, in conjunction with one or more display device and one or more input device.

Figure 45:
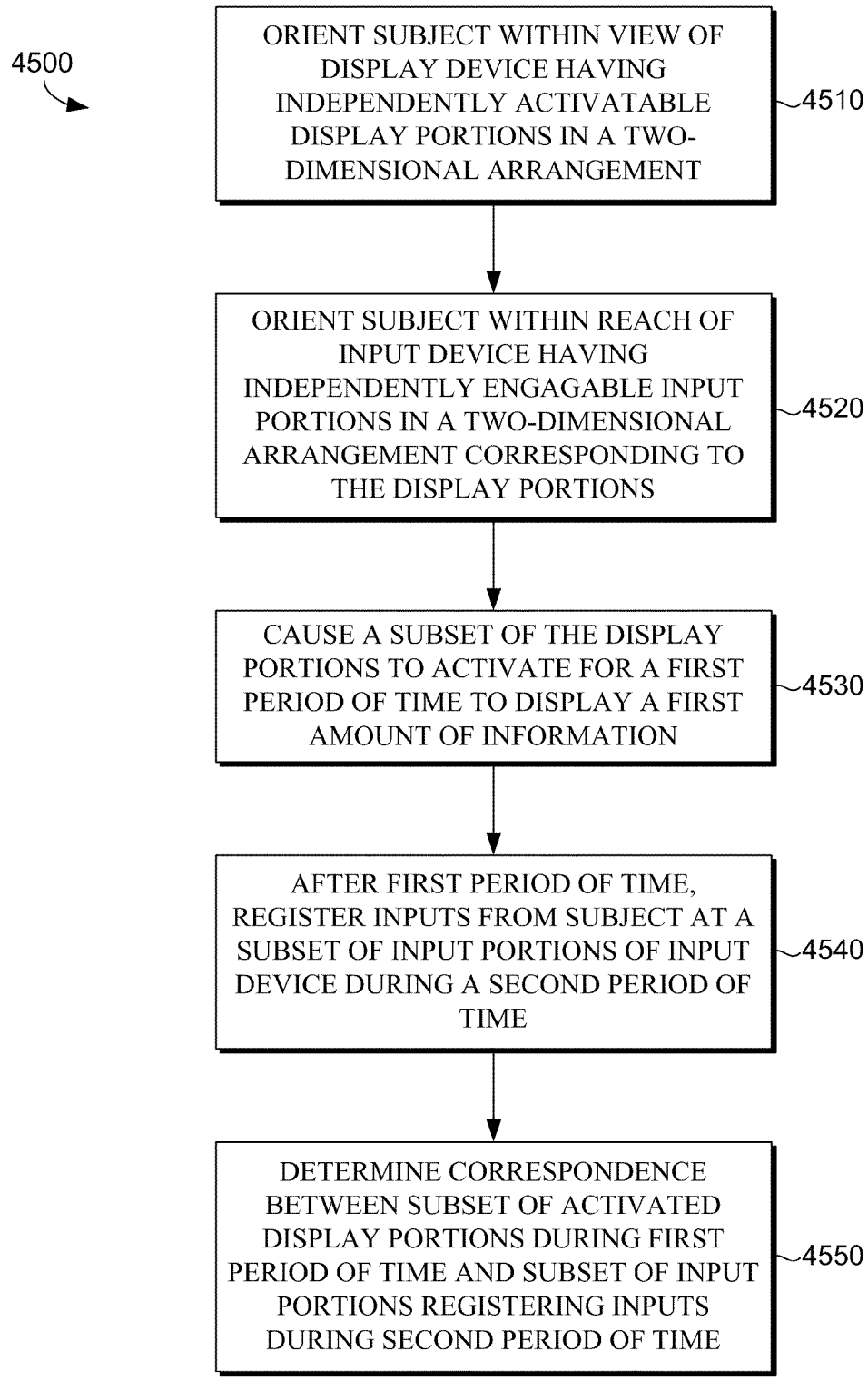
FIG. 45 illustrates another method for testing and/or training the visual perception span and/or speed of a subject in accordance with an embodiment of the invention.

FIG. 45 illustrates a method 4500 for testing and/or training the visual perception span and/or speed of a subject in accordance with an embodiment of the present invention. In step 4510, a subject may be oriented within view of a display device. The display device may have independently activatable display portions in a two-dimensional arrangement. In step 4520, the subject may be oriented within reach of an input device. The display device of step 4510 and the input device of step 4520 may comprise a single touch-sensitive display device that both displays information to and receives inputs from the subject. The input device may have independently engagable input portions in a two-dimensional arrangement. The two-dimensional arrangement may correspond to the display portions of the display device. Alternatively, the two-dimensional arrangement may be more extensive than the display portions, such that the two-dimensional arrangement may correspond to the dimensions of a number of different display devices.

At step 4530, a subset of the portions of the display device may be activated for a first period of time to provide a first amount of visual information to subject. In embodiments, "period of time" may refer to a discrete amount of time. The subset may comprise display portions that may possess varied characteristics, such as different colors, different sizes, etc. The amount of information displayed during step 4530 may directly relate to the amount of portions included in the subset activated and/or the characteristics that subset possesses. After a first period of time, the inputs from the subset may be registered in an input device in step 4540. A single touch-sensitive screen may comprise both a display device and an input device. The inputs registered may comprise a subset of the input portions of a input device. Step 4540 may occur during a second period of time subsequent to the period of time of step 4530. After the expiration of the second period of time, the subject may be locked from adding any additional inputs. Once inputs have been registered on an input device, a correspondence between a subset of activated display portions and a subset of input portions may be determined based on the inputs registered during the second period of time.

Method 4500 may be repeated any number of times to test and/or train the visual perception speed and/or span of a subject. The amount of information displayed in step 4530 may vary in different iterations of method 4500 to test/train the perception span of the subject. The first period of time during which a subset of the portions of the display device are activated in step 4530 may vary in different iterations of method 4500 to test and/or train the perception speed of a subject.

Figure 46:
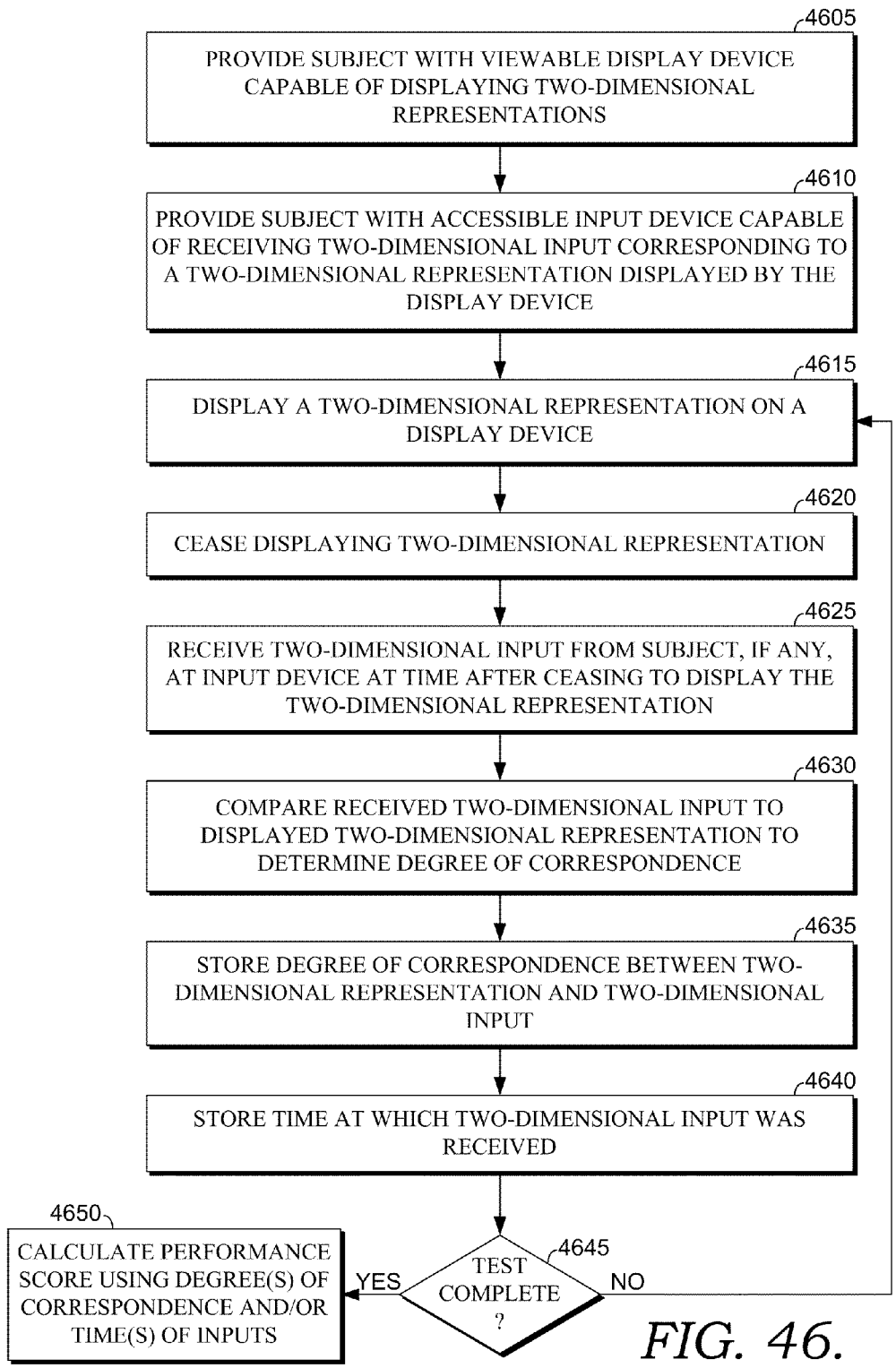
FIG. 46 illustrates a further method for testing and/or training the visual perception span and/or speed of a subject in accordance with an embodiment of the invention.

Referring to FIG. 46, a further method 4600 for testing and/or training the visual perception span and/or speed of a subject in accordance with an embodiment of the present invention. In step 4605, a subject is provided with a viewable display device capable of displaying two-dimensional representations. In step 4610, the subject is provided with an accessible input device capable of receiving two-dimensional input. A single touch-sensitive screen may comprise both a display device and an input device. Alternatively, the two-dimensional input may comprise a series of buttons and/or touch screen portions at which a subject may indicate the location on an input device that corresponds with the location at which the subject saw an active portion on the display device, and the display device may comprise any type of monitor, display, etc. In step 4615, visual information comprising a two-dimensional representation is displayed on the display device. The amount of visual information displayed in step 4615 may be controlled for testing and/or training the visual perception span of an individual. The display of the two-dimensional representation on the display device may cease in step 4620. The duration of step 4615 prior to step 4620 may be controlled for testing and/or training the visual perception speed of an individual.

In step 4625, a two-dimensional input from the subject is received at the input device. One or more responses may be input at a time after the display of the two-dimensional representation has ceased in step 4620. After the two-dimensional response inputs have been received at the input device, the responses may be compared to the two-dimensional representation displayed on the display device in step 4630. The comparison may be used to make a determination as to the degree of correspondence between the two-dimensional response inputs and the two-dimensional representation displayed on the display device. The degree of correspondence may be stored in step 4635. In addition, the time at which the responsive two-dimension input was received may be stored in step 4640, which may be used as a indication of quickness of a response.

At step 4645, a determination may be made as to whether the testing and/or training of the visual perception span and/or speed of the subject is complete. If the testing and/or training is not complete, method 4600 may return to step 4610. If, however, the testing and/or training is complete, method 4600 may proceed to step 4650 and calculate a performance score using information such as, for example, the degree of correspondences between the two-dimension response inputs and the two-dimensional representations displayed on the display device. The duration of time during which visual information was displayed, the quickness of a response, prior testing and/or training by the subject or others, etc., although only a portion of these types of information may be used.

Figure 47A:
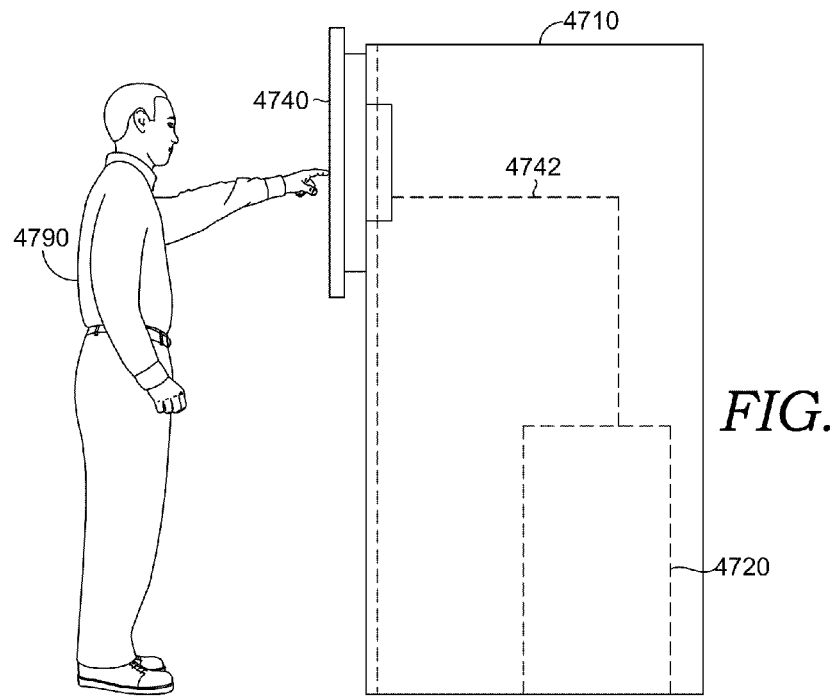
FIGS. 47A-47C illustrate an embodiment of the invention utilizing a single touch sensitive display device as both a display device and as an input device in accordance with embodiments of the present invention.
Figure 47B:
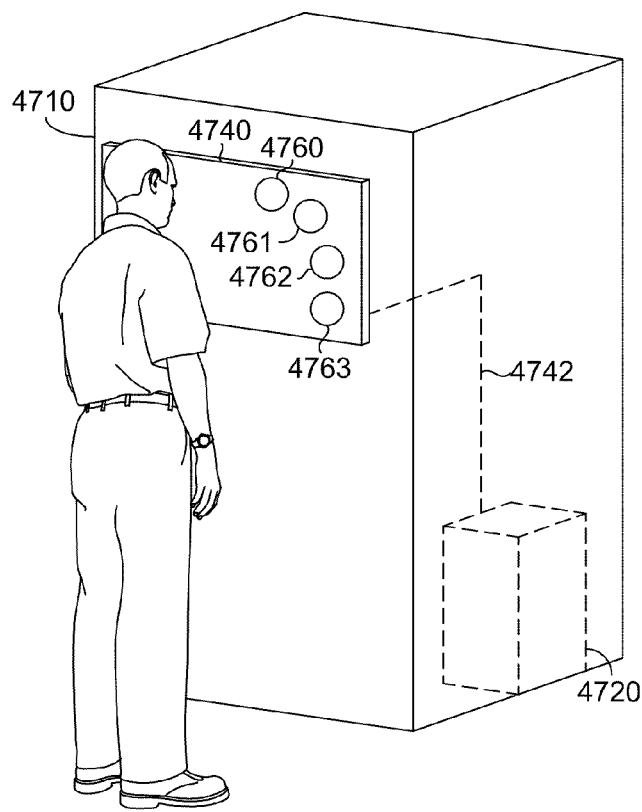
Figure 47C:
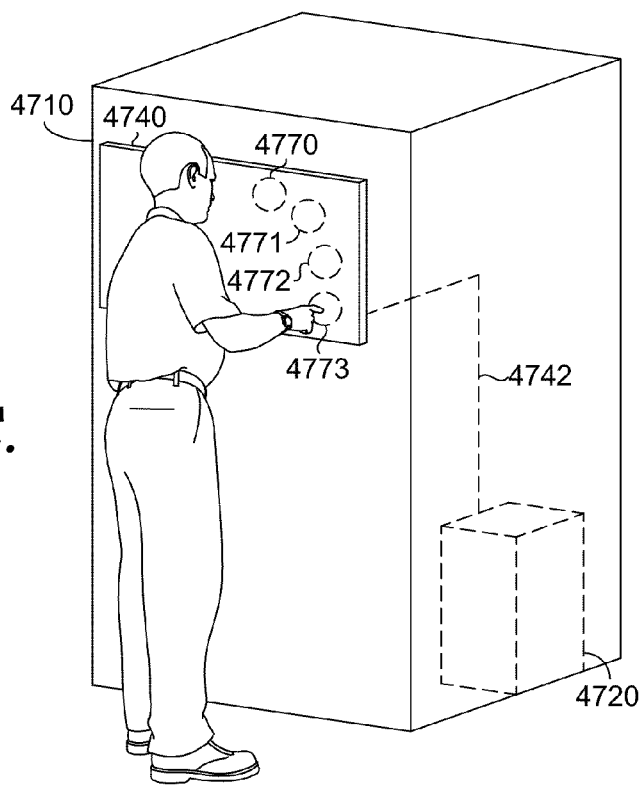

Referring now to FIGS. 47A-47C, a system 4700 for testing and/or training the visual perception span and/or speed of a subject 4790 is illustrated. System 4700 may use a touch-sensitive screen 4740 as both a display device and an input device in testing and/or training the visual perception span and/or speed of subject 4790, which permits subject 4790 to utilize his sensory memory in testing and/or training.

Touch-sensitive screen may be rigidly affixed or adjustably attached to kiosk 4710. A control unit 4720 may connect to touch-sensitive screen via connection 4742. Control unit 4720 may comprise any type of computing device, or multiple computing devices, with a processor(s), a storage device(s), a network connection(s), etc. Connection 4742 may comprise any type of wired or wireless connection.

Control unit 4720 may cause touch-sensitive screen 4740 to display spatially arranged visual indicia, such as first indicia 4760, second indicia 4761, third indicia 4762, and fourth indicia 4763. Control unit 4720 may also receive touch inputs from touch-sensitive screen 4740, such as first selection 4770, second selection 4771, third selection 4772, and fourth selection 4773. Of course, subject 4790 may not necessarily successfully register inputs correctly corresponding to displayed visual indicia. As described above, control unit may measure both the accuracy of the selections by subject 4790 to obtain a measure of the perception span of subject 4790, and more or less visual information may be included in different testing/training iterations. Also as described above, the duration of time during which visual indicia are displayed may be varied by control unit 4720 to provide a measure of the perception speed of subject 4790. Further, the time required for subject 4790 to provide a response may be measured and recorded.

Figure 48:
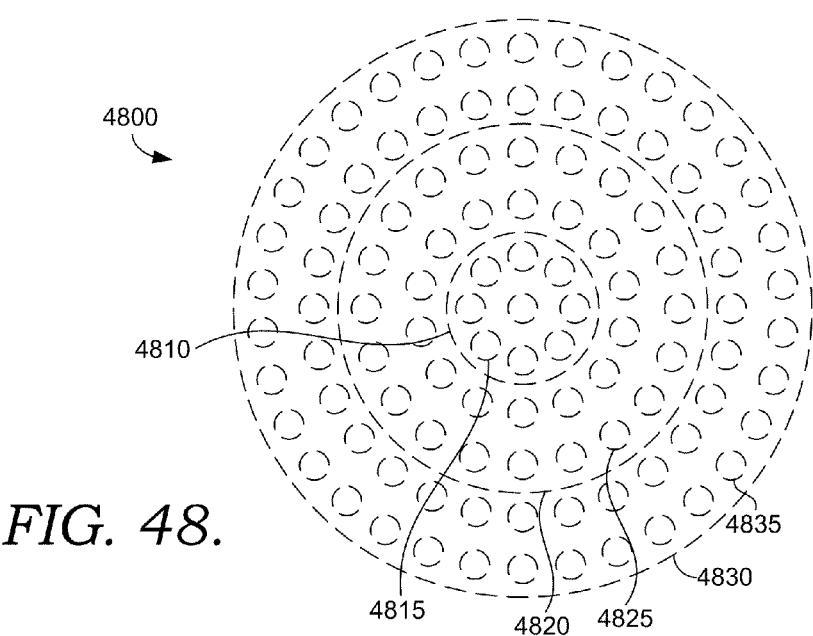
FIG. 48 illustrates an embodiment of a display device capable of displaying varying amounts of visual information for use in testing and/or training the visual perception span and/or speed of a subject in accordance with embodiments of the present invention.

Referring now to FIG. 48, a further embodiment of a display device capable of displaying varying amounts of visual information for use in testing and/or training the visual perception span and/or speed of a subject is illustrated. Display device 4800 may display a plurality of visual indicia in a two-dimensional spatial arrangement to provide visual information to a subject. Display device 4800 may be touch-sensitive, so as to enable a subject to register inputs corresponding to the information displayed at a prior time by touching the display device 4800. The indicia illustrated in the example of FIG. 48 comprise individual circles that may be active or inactive, although other types of indicia that may possess various traits beyond simply active or inactive may be used. In use, a subset of the indicia of display device 4840 may be activated for a first period of time and thereafter deactivated, at which time a subject may attempt to touch portions of display device 4800 previously activated. As illustrated in FIG. 48, indicia may be arranged in expanding concentric circles, such as first circle 4810, second circle 4820, and third circle 4830. First circle 4810 may contain a first plurality of indicia, such as first indicia 4815. Second circle 4820 may contain a second plurality of indicia, such as second indicia 4825. Third circle 4830 may include a third plurality of indicia, such as third indicia 4835. More or fewer concentric circles than the three illustrated in FIG. 48 may be used in accordance with the present invention, and any given concentric circle may contain more or fewer indicia than illustrated in FIG. 48 without departing from the scope of the present invention. The use of a plurality of concentric circles, each containing a predetermined maximum amount of possible visual information, in this case a predetermined number of indicia, permits the amount of visual information presented during the testing and/or training of the visual perception span and/or speed of a subject to be adjusted to contain more or less visual information for particular iterations by including indicia within more or fewer circles. For example, a testing and/or training session may commence using only visual indicia within the first circle 4810. After the subject has correctly responded to a predetermined number of displays of visual information within first concentric circle 4810, further testing and/or training iterations may be performed using indicia included within both first concentric circle 4810 and within second concentric circle 4820. If the subject successfully respond to such iterations, the subject may thereafter perform testing and/or training iterations using the first concentric circle 4810, the second concentric circle 4820, and the third concentric circle 4830. Of course, testing and/or training iterations may begin using the maximum amount of possible information and reduce the presented information through the course of testing and/or training, or testing and/or training iterations may be distributed in other fashions that vary between more and less information being displayed to a subject.

Figure 49:
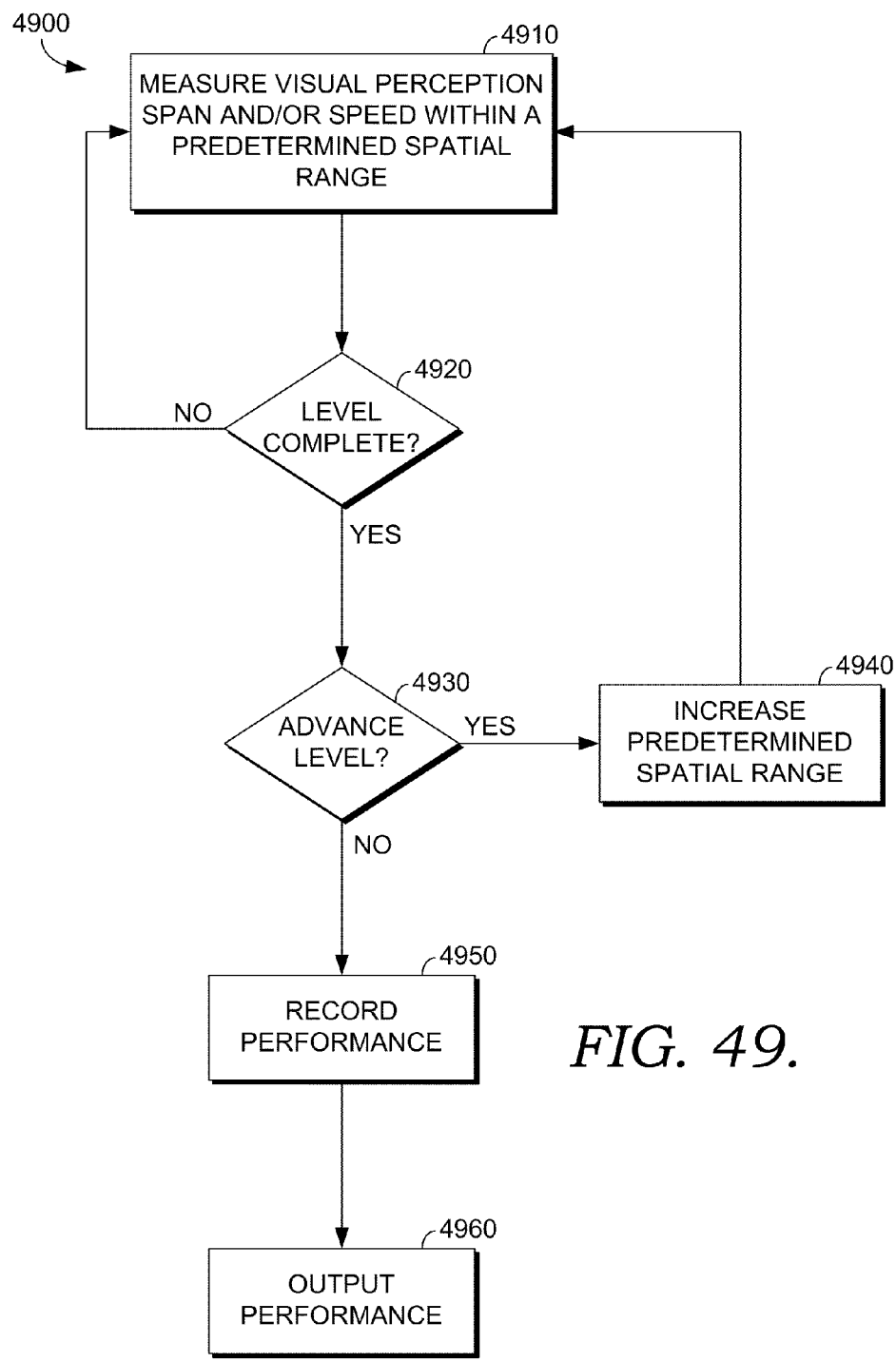
FIG. 49 illustrates a further method for testing and/or training the visual perception span and/or speed of a subject in accordance with embodiments of the present invention.

Referring now to FIG. 49, a further method for testing and/or training the visual perception span and/or speed of a subject in accordance with the present invention utilizing multiple levels is illustrated. Method 4900 may utilize concentric circles of indicia, such as illustrated in FIG. 48, to vary the spatial range of information displayed in an iteration, but method 4900 may be adapted to use other displayed configurations that vary the amount of information displayed for any given iteration, the difficulty of perceiving the displayed information, the amount of time for which a given information set is displayed, or otherwise varies the difficulty of an iteration. In step 4910, the visual perception span and/or speed of a subject may be tested and/or trained within a predetermined spatial range. The predetermined spatial range in step 4910 may comprise, for example, the first circle 4810 illustrated in FIG. 48. In step 4920 a determination is made as to whether the level is complete. The determination of step 4920 may be based upon criteria such as the number of iterations at an earlier level that have been performed, number of accurate responses provided at an earlier level, the accuracy of prior responses, etc. If the conclusion of step 4920 is that the level is not complete, method 4900 may return to step 4910. If the conclusion of step 4920 is that the level is complete, method 4900 may proceed to step 4930. Step 4930 determines whether to advance another level. If the conclusion of step 4930 is to advance a level, method 4900 proceeds to step 4940, which increases the predetermined visual range for visual perception span and/or speed testing and/or training. For example, step 4940 may increase the spatial range to include both the first circle 4810 and the second circle 4820 illustrated in FIG. 48. Thereafter, method 4900 returns to step 4910 using the increased spatial range. If the determination of step 4930 is not to advance a level, method 4900 may proceed to step 4950 of recording the performance of the subject. Of course, step 4950 may be performed contemporaneously with other measurements. Method 4900 may thereafter proceed to step 4960 of outputting the performance of a subject. Step 4960 may comprise displaying a score on a display device, printing a report of the performance of the subject, making an electronic record of the subject's performance on a local storage media or on a remote server or storage media, or any other way of providing a measure of performance of the subject for contemporaneous or subsequent use.

Eye-Hand Coordination Testing and/or Training

Eye-hand coordination involves an individual's ability to respond to a visual stimulus. While aspects of the present invention may be utilized to test and/or train other types of coordination (for example, eye-foot coordination), it shall be generally described herein in the context of eye-hand coordination testing and/or training.

A series of visual indicia may be displayed on a touch sensitive screen. A subject participating in the testing and/or training may make appropriate responses to the indicia, for example, by attempting to touch the indicia where they are displayed on a touch screen with their hands and/or fingers. Characteristics of the indicia, such as their color, may indicate that different responses are appropriate or that the indicia should be disregarded entirely (e.g., go/no-go testing). For example, a red displayed indicia may require no response, while a green indicia may require a physical contact. Further characteristics may require a particular hand or motion to be deemed appropriate.

Embodiments of the present invention may determine both the speed with which a subject responds appropriately to an indicia and the accuracy with which a subject responds to the indicia. For example, subjects may be fast but not accurate such that an athlete recognizes when an indicia is displayed and therefore contacts a display screen as an input, but the contact is not within a predefined area of the displayed indicia. In the alternative, a subject may be accurate but not fast such that the subject requires a period of time to identify the indicia and to make contact within a predefined area of the displayed indicia. As a result, it may be desirable to measure, record, and score the accuracy and/or speed of an subject's eye-hand coordination. Accuracy of an subject's eye-hand coordination refers to the individuals ability to move his or her hand to the location indicated by the indicia. The speed of a subject's eye-hand coordination refers to the time laps required for an individual to make a response to a displayed indicia. Speed and accuracy may differ in a given individual, even in comparison to other individuals.

Figure 50:
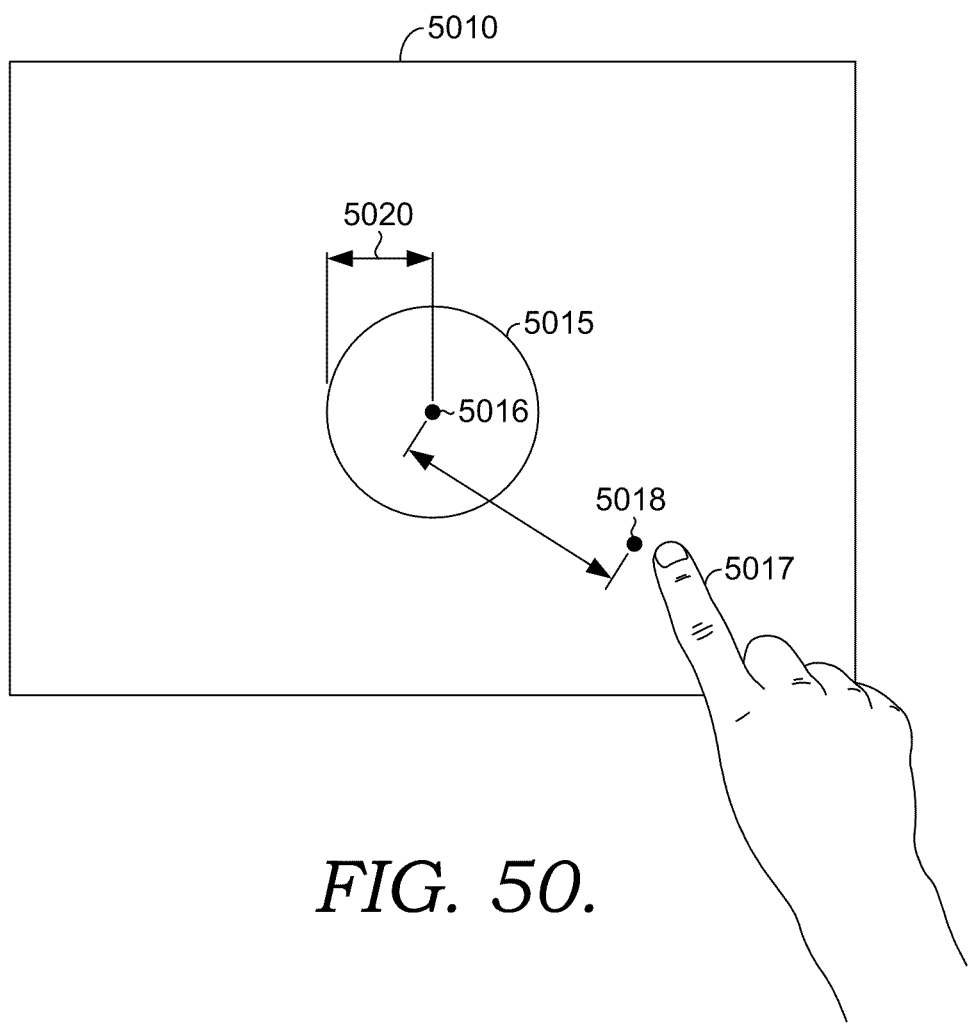
FIG. 50 illustrates aspects relating to the measurement of distance between a displayed indicia and a touch response in accordance with embodiments of the present invention.

Referring now to FIG. 50, aspects relating to the measurement of distance between a displayed indicia and a touch response are illustrated. Indicia 5015 possesses a center 5016. As illustrated in FIG. 50, a subject is attempting to touch indicia 5015 with his or her finger 5017, which contacts screen 5010 at a point centered at point 5018. As can be seen in FIG. 50, touch point 5018 does not exactly match indicia center 5016. The distance between center 5016 of indicia 5015 and center 5018 of touch by finger 5017 may be calculated to determine the accuracy of a touch response.

In an exemplary embodiment, a subject's contact that occurs within a distance 5020 of the center point 5016 of indicia 5015 is within a predefined threshold. For example, the distance 5020 may coincide with the radius of indicia 5015 if indicia 5015 is a circular indicia. However, the distance 5020 may represent any distance from the center point 5016, such as a distance greater than or less than a graphical representation (e.g., area represented by indicia 5015) of an indicia is contemplated.

Additionally, it is contemplated that an indicia, such as the indicia 5015 may be presented at any location of a display (e.g., screen 5010) at any given time during a testing or training activity. For example, to prevent anticipation or memorization by a subject, an indicia for eye-hand coordination testing and/or training may be presented in pseudo random location at irregular intervals. Additionally, the varied location at which an indicia is displayed allows for all regions of a subject's field of view of view to be tested and/or trained. Therefore, if certain gaze angles are determined to need additional or less testing/training, an activity may be created with such a limitation as a condition. For example, certain sports may require more emphasis to be placed on eye-hand coordination at particular locations of a subject's field of gaze, as such, a testing and/or training activity may be tailored to satisfy such a requirement.

Similarly, performance may be analyzed based on field of view/gaze angle. Metrics may be collected and maintained based on responses provided by a subject at various locations that include various gaze angles for the subject. As a result, the metrics may be analyzed to indicate which locations and resulting gaze angles of the subject that varied relative to other or surrounding locations and resulting gaze angles. As previously discussed, this may be emphasized depending on the type of activity customarily associated with the subject's sport.

As previously discussed, it is contemplated that speed and/or accuracy of a subject may be tested and/or trained. For example, the testing of speed may include beginning a timer when an indicia is presented to when a subject provides an input. In an exemplary embodiment, the speed of a subject is only calculated when the point of contact is within a predefined distance of the an indicia. In an alternative embodiment, speed is determined regardless of the accuracy and/or correctness of a subject's input. Similarly, the measurement of accuracy may include a binary result where a positive input results when a subject provides an input within the visual indicia and a negative input results when the subject provides an input outside of the presented indicia. In yet another embodiment, accuracy is measured based on a distance from a center point of a displayed indicia or from a displayed indicia in general. In this exemplary embodiment, a bulls eye type pattern may be employed so that the greater the radial distance from a center point of a target in which an input is provided, the lower a resulting accuracy is for the subject.

Go/No-Go Testing and/or Training

Go/no-go testing and/or training is an activity in which a subject is provided with an indicia of changing characteristics, depending on currently presented characteristics, the subject is expected to provide or not provide an input. For example, a previous discussed with respect to FIGS. 10I and 10J, an indicia may be presented to a subject that has a first property or a second property. Depending on the property of the indicia, the subject is expected to provide a response or no response. For example, a subject may be instructed to provide an input, e.g., make contact with a touch screen, when an empty circle (e.g., FIG. 10J) is presented. The instructions may additionally indicate that the subject is not intended to provide an input when a solid circle (e.g., FIG. 10I) is presented.

In addition to monitoring and recording the ability of a subject to correctly identify the proper "go" indicia, it may be desirable to monitor and record the ability of the subject to correctly abstain from providing an input when a "no go" indicia is presented. In this manner, both false positives and false negatives may be monitored.

Similar to other testing and training activities discussed herein, it is contemplated that an indicia presented to a subject may be located at a pseudo random location within a display screen. The irregularity of display location inhibits a subject from anticipating, which may alter results. Additionally, effects of gaze angle may be incorporated into an analysis of a go/no go activity when the indicia covers a greater area of a display screen. However, it is contemplated that an indicia may be presented in a constant or at least logical location to eliminate one or more variables (e.g., target capture time). Further, the time for which an indicia is displayed to a subject may also be varied so that it is random, constant, or varied. For example, the time for which a indicia is displayed may be held at a constant interval, but the time between displaying of multiple indicia may be varied to reduce anticipatory effects on the results.

In yet another exemplary embodiment, the characteristics or properties of an indicia may be altered at any point, systematically or randomly. For example, shape, color, shading, brightness, orientation, size, or other attributes of an indicia may be altered, amended, or changed in whole or in part. In an exemplary embodiment, multiple characteristics of an indicia are changed at any given presentation. Further, a subject may be provided with multiple "go" characteristics and multiple "no go" characteristics, such that the subject is responsible for identify multiple properties when determining if to provide an input.

In addition to monitoring the ability to correctly identify, by touching the displayed indicia, the time in which a subject requires to provide an input may also be monitored. In an exemplary embodiment, an indicia may be presented for a first time period but a subject provides an input within a second time period. The second time may be more or less than the first time. Therefore, in an embodiment, regardless if the first or second time is longer, if an input is received within a predefined threshold, an input is recorded. However, in an additional embodiment, it is contemplated that the second time period must be equal to or less than the first time period in order for the input to be recorded.

Therefore, in an exemplary embodiment, a subject is instructed to provide an input when a first property is presented on an indicia and to abstain from providing an input when a second property (or lack of the first property) is presented (or not presented) on the indicia. The subject may provide an input by way of contacting a touch screen display or a multi-touch device to indicate a go/no go input. It is contemplated that additional inputs discussed herein may be implemented. As the subject views a display screen, an indicia including one or more properties is presented to the subject by way of the display screen. The subject then must determine if the indicia indicates a "go" or a "no go" indicia by the characteristics (or lack of characteristics). At the point the subject makes a determination, the subject then provides (or abstains) an input indicating go and/or no go. A determination is then made by a computing device if the input corresponds with an appropriate input. Based on this determination, one or more metrics are calculated. The process may continue for a defined or systematic number of iterations prior to completing the activity. Upon completion, one or more metrics may be calculated for the subject.

Reaction Time Testing and/or Training

Figure 51A:
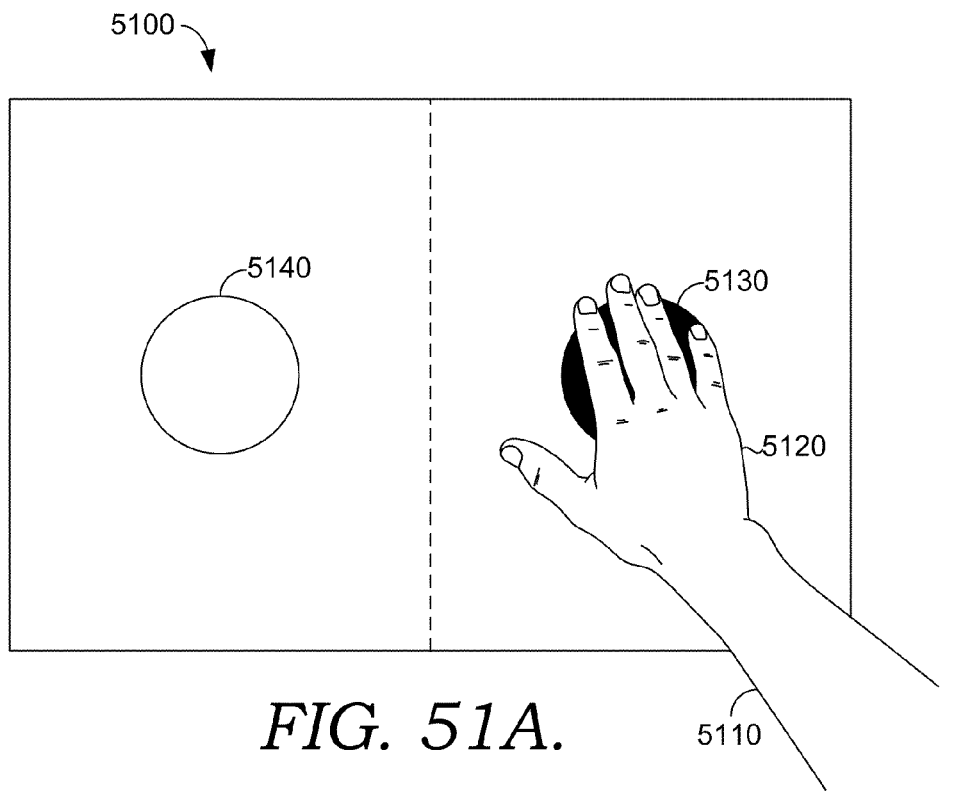
Figure 51B:
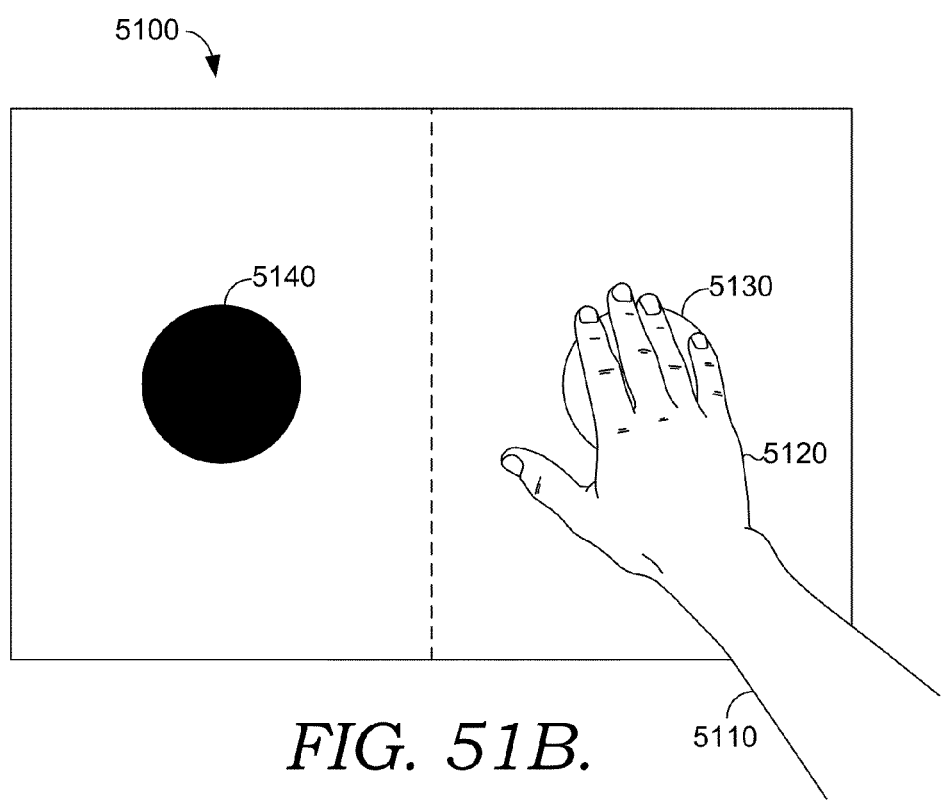
Figure 51C:
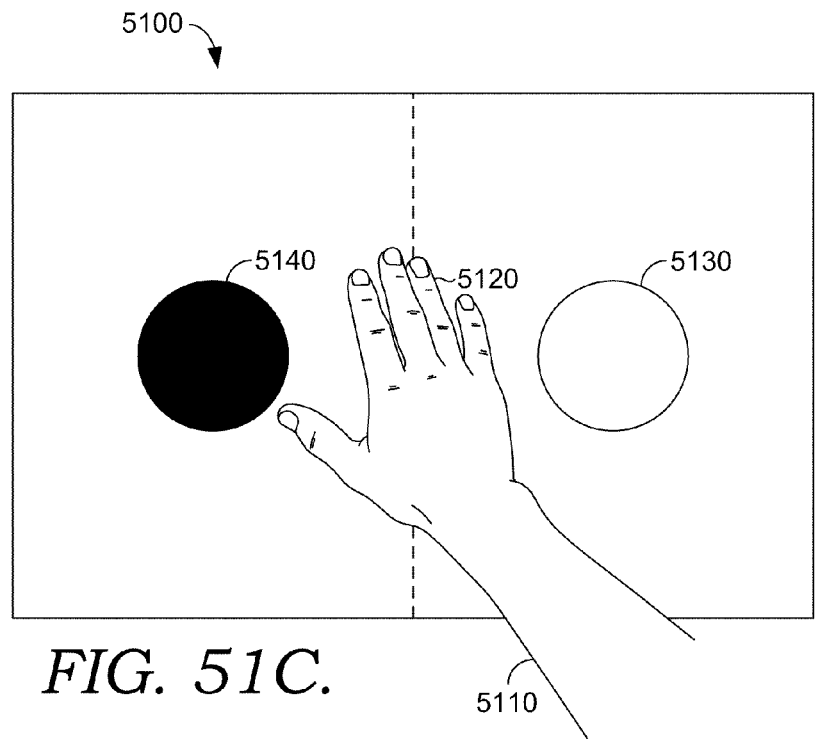
Figure 51D:
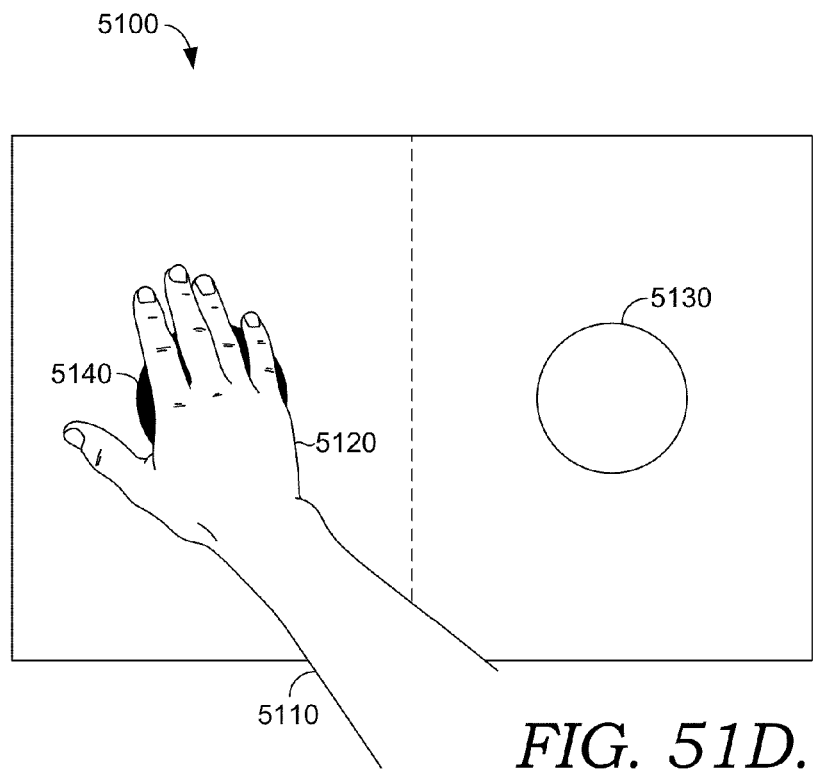

Referring now to FIGS. 51A-51D, an example of the use of the present invention for reaction time testing and/or training is illustrated. The examples illustrated in FIGS. 51A-51D may utilize the second touch-sensitive screen of kiosk. As illustrated in FIG. 51A, screen 5100 may display a first target 5130 and a second target 5140. First target may comprise the starting point for the hand 5120 of subject 5110. In testing or training subject may place his or her hand 5120 upon first target 5130 until an indication is provided to react by placing hand on second target. In the example illustrated in FIG. 51A, reaction time testing and/or training has begun with first target 5130 having a first state, in this instance black, and second target 5140 having a first state in this case white. In FIG. 51B, the state of first target 5140 has changed to white and the state of second target 5130 has changed to black. In the example presently illustrated, this change in color is the indication for subject to attempt to move his or her hand from first target to second target as quickly as possible. FIG. 51C illustrates the hand 5120 of subject as it moves from first target to second target. FIG. 51D illustrates the completion of the hand 5120 movement task by subject from first target 5130 to second target 5140. The use of a touch-sensitive screen, such as second display device of kiosk, permits the unified testing and/or training system to record the time at which the signal is provided to subject (in this instance, the changing of state of first target and/or second target), the time at which hand of subject leaves first target, and the time at which the hand of subject contacts second target. Of course, other indications may be given for subject to move hand from first target to second target, such as other changes in visual properties of the targets, a stimuli such as a sound or visual stimuli, or even the appearance of the second target. For example, second target need not be visually displayed at the outset of reaction time testing and/or training, but may instead appear as the indication to subject to move his or her hand. In such an instance, the second target may appear at a variety of locations upon display device Multi-Touch Input Device/Hand Held Display Device for Use as Input Device and/or Output Device Embodiments of the present invention relate to systems, methods, and computer storage media for receiving an input to a sensory test by way of a touch-screen device having memory and a processor. The method may comprise receiving instruction by way of a wireless communication protocol from a sensory testing and training device. The instructions are comprised of a command to display a graphical element on the touch-screen device. The method may also include displaying the graphical element on a display surface of the touch-screen device. The method may additionally include receiving an input from a subject in the form of a physical contact between the subject and the display surface of the touch-screen device. The input is in response to a sensory test or a sensory training activity. The method may also include communicating the input to the sensory training device utilizing the wireless communication protocol.

A sensory input touch device is a touch-screen device capable of receiving an input from a subject. For example, a sensory input touch device may include a capacitive display screen that is capable of sensing one or more contacts that may be transformed into one or more indications of a subject's intent. A touch-screen device may implement a variety of techniques to identify a subject's input. For example, a touch screen may rely on technologies such as a resistive, a capacitive, a surface acoustic wave, infrared, strain gauge, dispersive signal technology, and acoustic pulse recognition. Generally, a touch-screen device is capable of displaying one or more graphical elements in an area that is functional to receive an input, such as a touch. An exemplary touch-screen device 104 may include an IPOD TOUCH available from the Apple Corporation of Cupertino, Calif. Similarly, an exemplary touch-screen device 104 may include gaming counsels (e.g., PLAYSTATION PORTABLE available from the Sony Computer Entertainment Inc. of Japan)

Additionally, the sensory input touch device is capable of communicating wirelessly with one or more components and devices of a unified vision testing and/or training system. For example, a sensory input touch device may be functional to communicate utilizing an Internet Protocol (IP) such as Transport Control Protocol (TCP) or User Datagram Protocol (UDP). UDP may be referred to as a Universal Datagram Protocol. UDP is a minimal message-oriented transport layer protocol that is documented in IETF RFC 768. Typically, UDP allows for a connectionless communication that facilitates quick communication of data. As a result, UDP may be desirable for a touch-screen device to use in the communication of user input to reduce system-induced latency. For example, it is desired to reduce system-induced latency resulting from a sensory test measuring reaction time where a computing device instructs a sensory input touch device to display a graphical image and the sensory input touch device then must communicate back a user input in response to the graphical image. The subject's reaction time may be affected based on delays associated with communications between a sensory input touch device and a computing device. Therefore, a protocol, such as UDP that minimizes system-induced latency may be advantageous.

Figure 52:
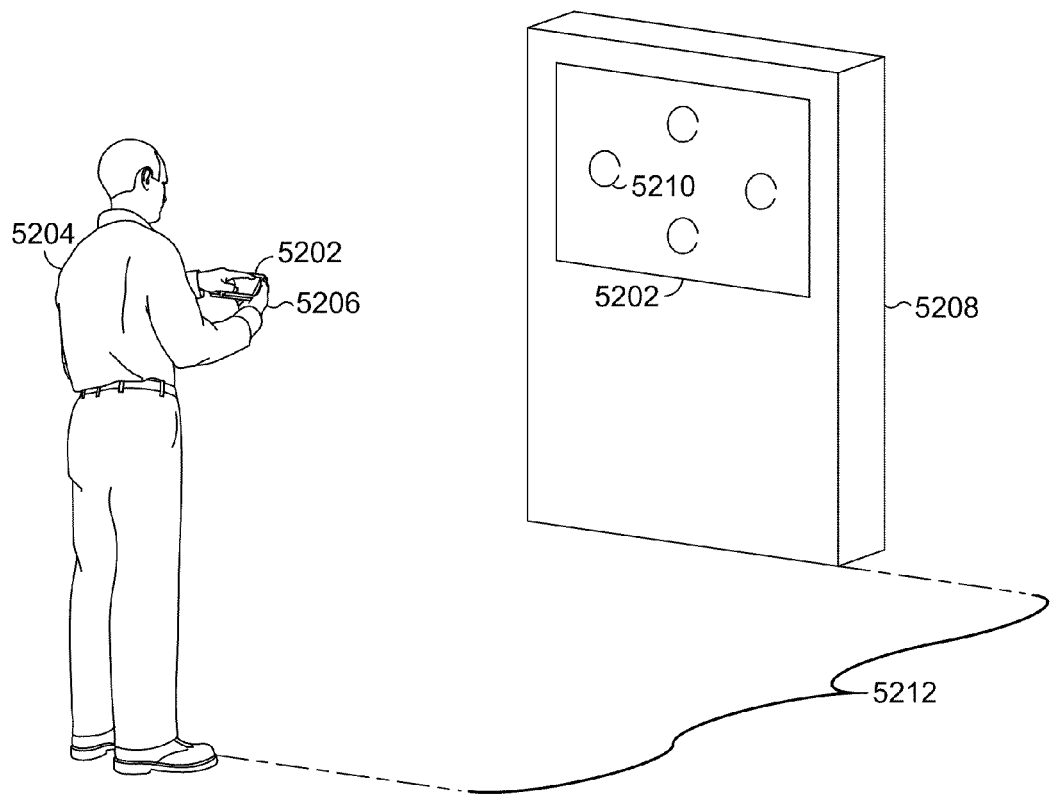
FIG. 52 illustrates a subject entering an input to a touch-screen device in response to a graphical element displayed from a sensory testing and training device in accordance with an exemplary embodiment of the present invention.

Turning to FIG. 52 that illustrates a subject 5204 entering an input 5206 to a touch-screen device 5202 in response to a graphical element 5210 displayed from a sensory testing and training device 5208 in accordance with an exemplary embodiment of the present invention. In an exemplary embodiment, the subject 5204 is positioned a predefined distance 5212 from the sensory testing and training device 5208. For example, one or more sensory testing and training activities may require the subject to be positioned a particular distance from the sensory testing and training device 5208.

Because of the predefined distance 5212, the touch-screen device 5202 may communicate utilizing a wireless connection. In an exemplary embodiment, the wireless connection is advantageous in order to allow the subject to participate in a sensory test or training activity that may be hindered as a result of a tether or wired connection.

In an exemplary embodiment, the subject 5204 is positioned the predefined distance 5212 from the testing and training device 5208 in order to participate in a sensory test or sensory training activity. The sensory testing and training device 5208 displays, on a display, one or more graphical elements 5210 that are intended to be perceived by the subject 5204. Because of the subject's 5204 perception of the graphical elements 5210, the subject enters the input 5206 into the touch-screen device 5202. For example, when the subject desires to indicate a graphical element at the top of the display should be selected, the subject 5204 may touch the touch-screen device in a manner prescribed by the touch-screen device to indicate a selection of the graphical element at the top.

Figure 53:
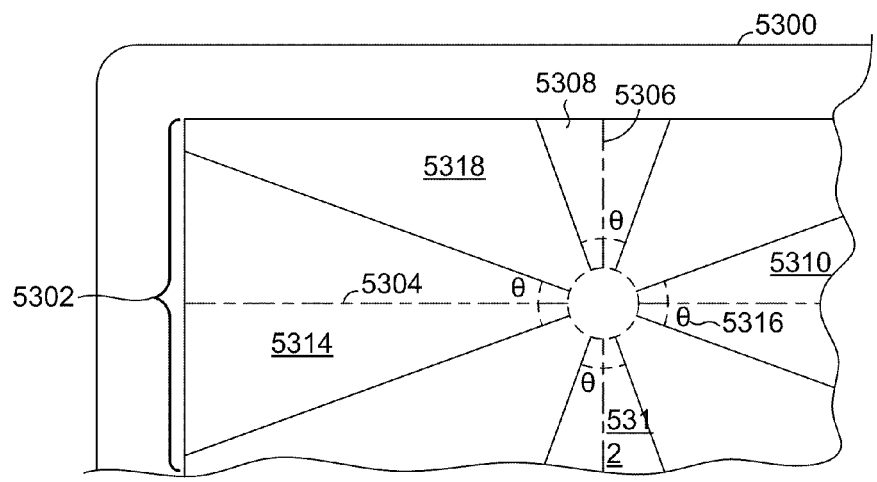
FIG. 53 illustrates a sensory input touch device in accordance with embodiments of the present invention.

Turning to FIG. 53 that illustrates a sensory input touch device 5300 in accordance with embodiments of the present invention. The sensory input touch device 5300 is a touch-screen device. The sensory input touch device 5300 is comprised of a display surface 5302. The display surface 5302 is functional to display one or more graphical elements and receive a subject's input. The sensory input touch device 5300 is illustrated with cut-away lines to illustrate that the sensory input touch device 5300 is not limited to a particular size or shape. Further, the cut-away lines also illustrate that an origin, as discussed below, is not limited to a particular location or area of a sensory input touch device 5300.

In an exemplary embodiment, the sensory input touch device 5300 is functional to receive a subject's input in the form of a slide touch. A slide touch consists of contact being made at an initial point on the display surface 5302 with contact being maintained across the display surface 5302 to a second point. For example, a subject may place a finger at the center of the display surface 5302 and drag the finger across the display surface 5302 to the right. Such a drag may indicate a directional "right" input. It is understood that the "origin" of the display surface 5302 may be at any point on the display surface 5302. For example, the origin, in an exemplary embodiment, is located at a point of initial contact by a user. Therefore, the origin on which a directional input or other input is based may be at any location of the display surface 5302.

In an embodiment, the direction of a drag is identified based on the degree from an orthogonal axis in which the contact travels. For example, contact that is maintained from a first point to a second point that is located to the right within 15 degrees from a horizontal axis of the display surface 5302 is a directional "right" command. The display surface 5302 may be comprised of an up portion 5308, a right portion 5310, a down portion 5312, and a left portion 5314. The portions center along one of the orthogonal axis 5304 and 5306. For example, the down portion 5312 is centered on the vertical axis 5306. The down portion 5312 radiates from an origin at a predefined degree 5316. The predefined degree 5316 is an angle at which the down portion 5312 extends from the axis on which it is centered (i.e., vertical axis 5306). The predefined degree 5316 may also be expressed relative to the axis dissecting an associated portion; therefore, an angle within a certain number of degrees of an axis represents a predefined angle twice the number presented. For example, if a right indication may be expressed with a movement within 7.5 degrees of the horizontal orthogonal axis 5304, then a predefined angle of 15 degrees is used as it includes both 7.5 degrees above and below the axis. It is contemplated that the orientation of the input touch device 5300 may determine what portion coincides with a particular direction. For example, if the input touch device 5300 is in a rectangular shape, when the device is oriented in a portrait manner, the "up" portion may coincide with the upper short side of the rectangle. While, if the device is oriented in a landscape manner, then the upper long side of the rectangle may coincide with the "up" portion.

In an exemplary embodiment, portions, such as the up portion 5308, the right portion 5310, the down portion 5312, and the left portion 5314 are nonoverlapping portions that do not share a common point on the display surface 5302. However, it is appreciated that an origin point at which an initial point of contact is made is an area that may be common to two or more of the portions because it is an intersection of various portions. Additionally, the origin may include a predefined radius extending from the initial point of contact in which no one portion is identified as being exclusive to that area. Further, the display surface may include one or more noninput portions, such as portion 5318. Portion 5318 is a portion that is located between the up portion 5308 and the left portion 5314. In an exemplary embodiment, an input identified as being associated with the portion 5318 is a null input that is not associated with a direction. For example, an input that is identified as being in the portion 5318 falls outside of a level of confidence that the input is intended to be associated with either the up portion 5308 or the left portion 5314. Therefore, noninput portions may exist between various input portions to provide confidence that a sensed input has a particular intent.

Further, in an exemplary embodiment, the predefined angle that defines one or more of the portions provides a range in which a user may enter an input. For example, in order to compensate for inaccuracies in holding an input device or inaccuracies of the user providing an input, the range as defined by an angle allows for the input to deviate from a precise axial movement. Therefore, if a user is not holding the input touch device in an apparent alignment with a customary level position, then a customary user input in an "up" direction would not correspond with the vertical axis 5306. However, because the "up" portion 5308 is defined by an angle theta, a user input may be identified as being an "up" input when the input is within the "up" portion 5308. Further, because a user may not be concerned with providing precise or exact directional indications, a range defined by an angle (e.g., angle 5316) allows for imprecision and inexactness of an input.

In an exemplary embodiment, an origin defined by the intersection of the orthogonal axis 5304 and 5306 is positioned at an initial point of contact on the display surface 5302. Therefore, regardless of the initial point of contact, the directional intent of a subject may be determined. While the various portions (e.g., 5308, 5310, 5312, 5314) are not displayed by the sensory input touch device 5300 in an exemplary embodiment, they are illustrated herein to provide clarity to the discussion. In an additional embodiment, one or more portions or visual elements may be displayed to aid a subject in providing an input consistent with the subject's intention.

Additionally, in an exemplary embodiment, one or more tactile guides may be associated with the input touch device

5300. For example, a protective cover may encase the input touch device 5300 that provides an opening for the display surface 5302 to be contacted by a user. The opening provided by the protective case may be limited to an active or useable area of the display surface 5302. Additionally, one or more linear, polygonal, or curvilinear surfaces may be coupled to the input touch device 5300 in order to provide tactile indications as to orientation, useable area, or axial locations of the input touch device 5300.

The input touch device 5300 may also include an audible emitter, such as a speaker. The audible emitter may produce one or more sounds, such as feedback to a user. The sounds may be used to provide interference, distractions, or information for use in the sensory training and/or testing.

Figure 54:
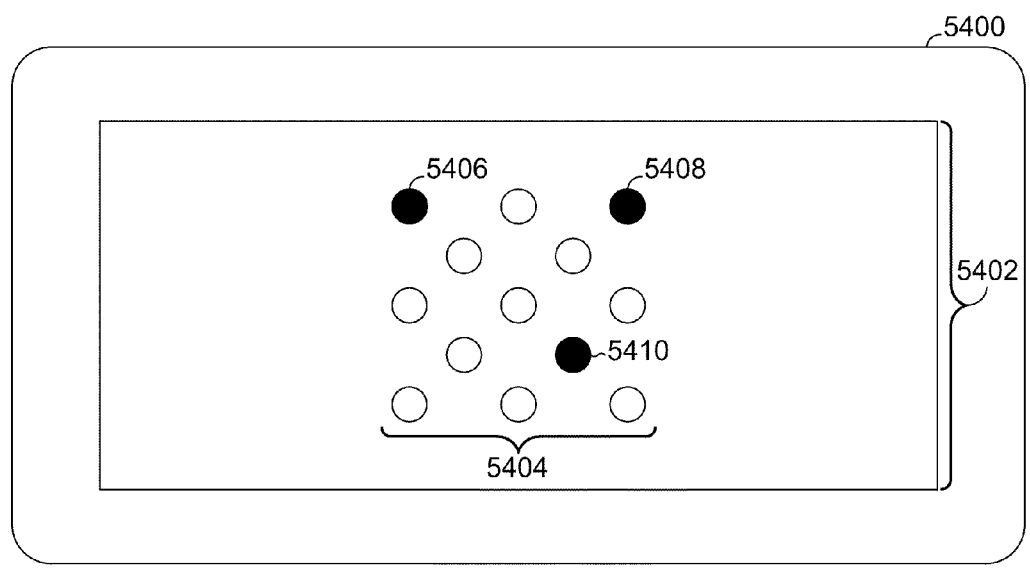
FIG. 54 illustrates a second sensory input touch device in accordance with an exemplary embodiment of the present invention.

Turning to FIG. 54 that illustrates a second sensory input touch device 5400 in accordance with an exemplary embodiment of the present invention. The sensory input touch device 5400 includes a display surface 5402 that is functional to display one or more graphical elements 5404. For example, sensory input touch device 5400 displays elements 5406, 5408, and 5410. The elements 5406-610 are visually present on the display surface 5402 as part of a sensory testing or sensory training activity. In an exemplary embodiment, a subject contacts the sensory input touch device 5400 at locations relative to each of the points 5406-5410 as an input. For example, an external display associated with a sensory testing and training device that is a predefined distance from the subject may display three graphical elements at locations that coincide with the graphical elements 5406-5410 selected by the subject. Therefore, the sensory input touch device 5400 may display one or more graphical elements to aid in the subject providing an input. Additionally, the sensory input touch device 5400 may display one or more graphical elements as part of a sensory test or a sensory training activity.

Figure 55:
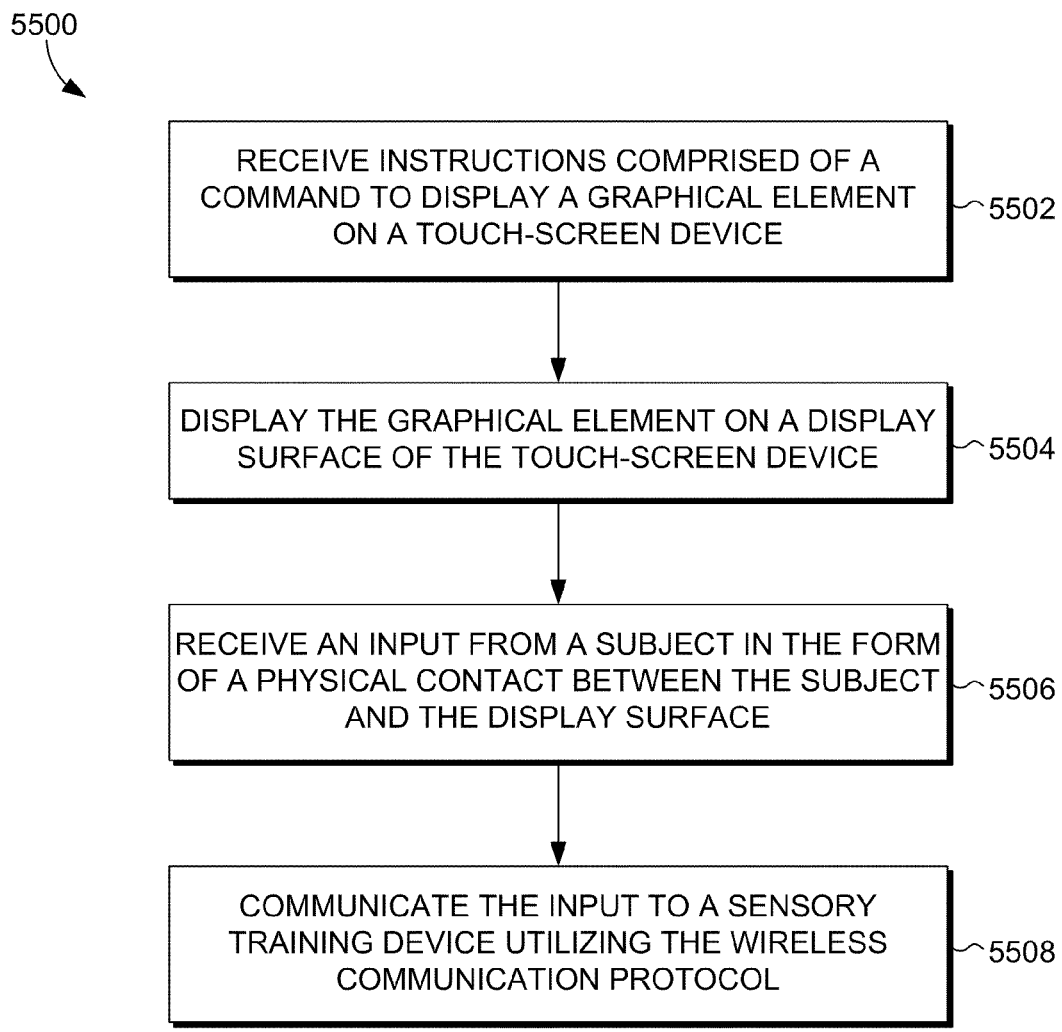
FIG. 55 illustrates a block diagram depicting a method for receiving an input to a sensory test by way of a touch-screen device utilizing a computing device having memory and a processor in accordance with an embodiment of the present invention.

Turning to FIG. 55 that illustrates a block diagram depicting a method 5500 for receiving an input to a sensory test by way of a touch-screen device utilizing a computing device having memory and a processor in accordance with an embodiment of the present invention. At a step 5502, a touch-screen device receives instructions comprised of a command to display a graphical element. For example, a sensory testing and training device may desire for instructional or tutorial information to be displayed on the touch-screen device. Additionally, a graphical element representing a start command may be displayed by the touch-screen device. In an exemplary embodiment, the graphical element is stored within the touch-screen device and the graphical element is accessed as a result of the command. For example, the instructions may include computer executable code that includes a command to display a particular image file stored within the touch-screen device. At a step 5504, the touch-screen device displays the graphical element on a display surface. For example, the graphical element may be rendered from a data file. In an exemplary embodiment, the instructions are received by way of a wireless communication protocol.

At a step 5506, the touch-screen device receives an input from a subject in the form of a physical contact between the subject and the display surface. For example, a subject may desire to provide a particular command as a result of one or more sensory stimulations presented as part of sensory testing or training, and as a result, the subject makes contact with the touch-screen device to signal an input.

At a step 5508, the touch-screen device communicates the input to a sensory training device utilizing a wireless communication protocol. In an exemplary embodiment, the touch-screen device communicates an interpreted command from the input. For example, the touch-screen device analyzes the input from the subject and determines the intent of the subject based on one or more predefined criteria, rules, and/or tolerances.

Figure 56:
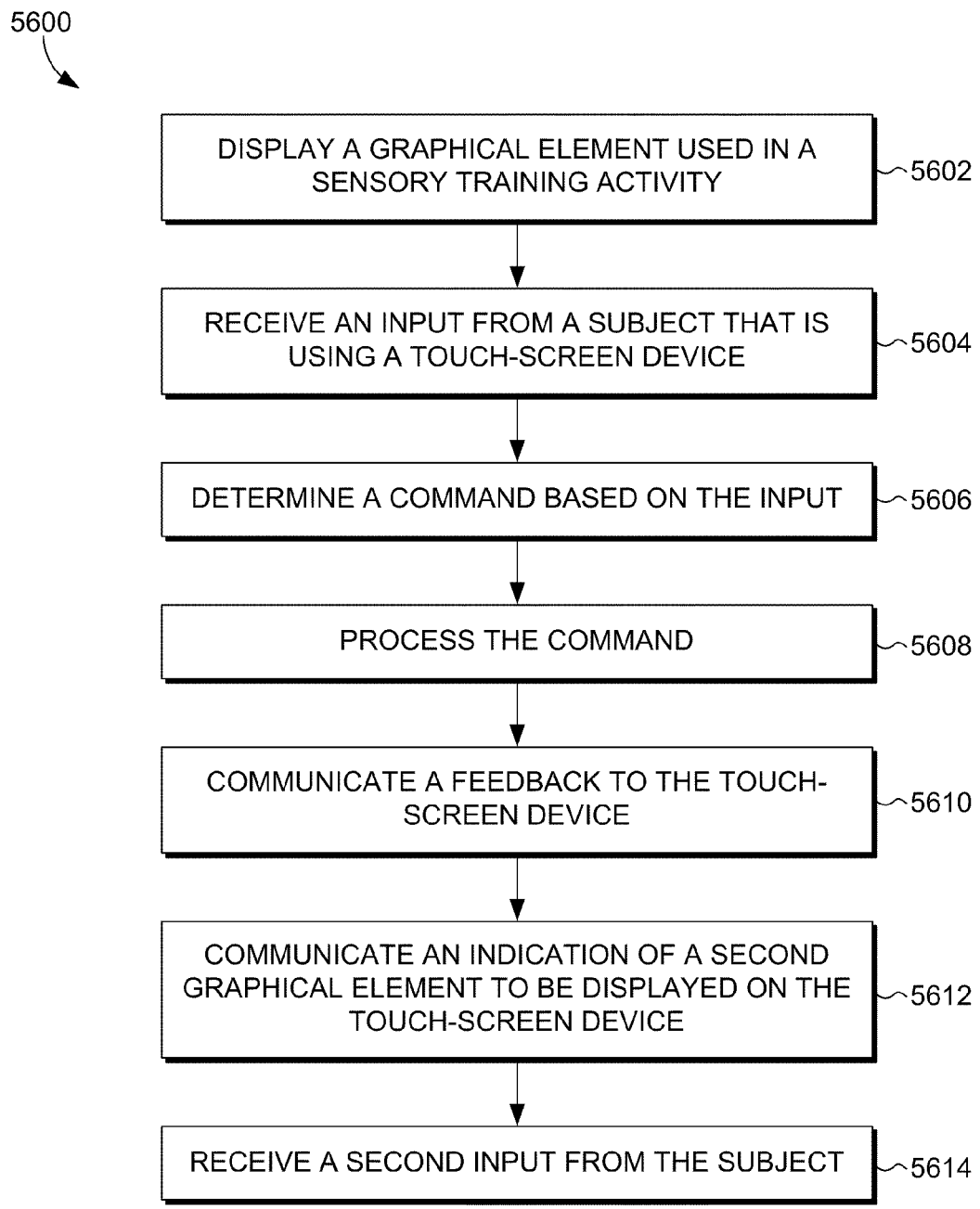
FIG. 56 illustrates a block diagram depicting a method for wirelessly receiving an input in response to a sensory training activity from a subject at a touch-screen device in accordance with an exemplary embodiment of the present invention.

Turning to FIG. 56 that illustrates a block diagram depicting a method 5600 for wirelessly receiving an input in response to a sensory training activity from a subject at a touch-screen device in accordance with an exemplary embodiment of the present invention. At a step 5602, a sensory training device displays a graphical element used as part of a sensory training activity. At a step 5604, the sensory training device receives an input from a subject that is using a touch-screen device. For example, in response to the graphical element displayed at the step 5602, a subject may provide a response, which is entered into a touch-screen device by the subject making contact with the touch-screen device. The touch-screen device in this example may then wirelessly communicate the input to the sensory training device.

At a step 5606, the sensory training device determines a command based on the input. For example, the input may be in a format effectively communicated by way of a wireless communication protocol, but the input is not in a format useable in the analysis of sensory training results, therefore the input is interpreted to a command that is useable by the sensory training device. For example, a numerical indicator may be communicated from the touch-screen device as an input. The numerical indicator is interpreted to represent a particular directional input (e.g., right, left, up, down). At a step 5608, the command is processed. For example, the command is processed by a computing device of the sensory training device to provide a result that may be analyzed relative to the graphical element previously displayed.

At a step 5610, the sensory training device communicates a feedback to the touch-screen device. For example, upon the successful processing of the command, a confirmation feedback may be communicated to the touch-screen device. In an exemplary embodiment, the feedback includes a command to produce an audible tone that represents the input has been received and processed. In an additional embodiment, the feedback may be an instruction to display a particular graphical element at the touch-screen device. Further, the feedback may include tactile feedback such as a vibratory sensation or other vibration-type input. For example, upon successful interpretation of an input command, the touch-screen device may vibrate in a first manner to indicate successful interpretation of an input. Additionally, it is contemplated that various vibrations (e.g., pulses, constant, intermittent, any combination thereof) may be utilized to indicate various meanings. For example, on a time exercise a low-time warning may be provided a second vibration type, an incorrect response may be a third vibration type, and a correct response is a fourth vibration type. Further, it is contemplated that combinations of feedback may be employed. For example, audible tones may be provided for correct feedback, vibrations may be provided for incorrect feedback, and a combination of vibration and audible feedback may be provided for expiration or completion of an activity.

At a step 5612, an instruction is communicated from the sensory training device to the touch-screen device. The instruction is a command to display a graphical element on the touch-screen device. For example, the touch-screen device may display a graphical element used as part of a sensory training activity (e.g., training object, instructions, input guides). At a step 5614, the sensory training device receives a second input from the subject. For example, in response to the graphical element displayed at the touch-screen device, the subject may provide input.

Having thus described the invention, what is claimed is:

1. A method for testing and/or training the visual abilities of an individual, the method comprising:
    at a first time, displaying at least one first visual indicia having a first trait using a first display device directly viewable by the individual, the at least one first visual indicia and the first display device being a first distance from the individual;
    in response to the display of the at least one first visual indicia, receiving a first input from the individual at a first input device, the first input having a trait that may correspond to the first trait of the first visual indicia;
    determining whether the trait of the first input corresponded to the first trait of the first visual indicia;
    at a second time, displaying at least one second visual indicia having a second trait using a second display device directly viewable by the individual, the at least one second visual indicia and the second display device being a second distance from the individual, the second display device being distinct from the first display device;
    in response to the display of the at least one second visual indicia, receiving a second input from the individual at a second input device, the second input having a trait that may correspond to the second trait of the second visual indicia;
    determining whether the trait of the second input corresponded to the second trait of the second visual indicia; and
    outputting the determination as to whether the trait of the first input corresponded to the first trait of the first visual indicia and the determination as to whether the trait of the second input corresponded to the second trait of the second visual indicia,
    wherein the first display device is a high-resolution display device which is used to measure static visual clarity, contrast sensitivity, depth perception, and near-far focusing ability of the individual, and
    wherein the second display device is a wide-aspect display device which is used to measure visual perception span, eye-hand coordination, visual decision making, and reaction time of the individual.

2. The method for testing and/or training the visual abilities of an individual of claim 1, further comprising:
    determining a time elapsed between the first time and the receiving of the first input;
    determining a time elapsed between the second time and the receiving of the second input; and
    outputting the time elapsed between the first time and the receiving of the first input and the time elapsed between the second time and the receiving of the second input.

3. The method for testing and/or training the visual abilities of an individual of claim 2, wherein:
    the second distance from the second display device to the individual comprises a visually near distance.

4. The method for testing and/or training the visual abilities of an individual of claim 3, wherein:
    receiving the first input comprises using a multi-touch device, and
    receiving the second input comprises using a touch sensitive display device as the second display device.

5. The method for testing and/or training the visual abilities of an individual of claim 4, wherein the multi-touch device further comprises a third display device.

6. A method for testing and/or training the visual abilities of an individual, the method comprising:
    at a first time, displaying at least one first visual indicia having a first trait using a first display device directly viewable by the individual, the first display device being a first distance from the individual, the first display device affixed to a supportive frame at an approximate eye level of the individual;
    in response to the display of the at least one first visual indicia, receiving a first input from the individual at a first input device, the first input having a trait that may correspond to the first trait of the at least one first visual indicia;
    determining whether the trait of the first input corresponded to the first trait of the at least one first visual indicia;
    at a second time, displaying at least one second visual indicia having a second trait using a second display device directly viewable by the individual, the second display device being a second distance from the individual, the second display device being distinct from the first display device;
    in response to the display of the at least one second visual indicia, receiving a second input from the individual at a second input device the second input having a trait that may correspond to the second trait of the at least one second visual indicia,
    determining whether the trait of the second input corresponded to the second trait of the at least one second visual indicia; and
    outputting the determination as to whether the trait of the first input corresponded to the first trait of the at least one first visual indicia and the determination as to whether the trait of the second input corresponded to the second trait of the at least one second visual indicia,
    wherein the first display device is a high-resolution display device which is used to measure static visual clarity, contrast sensitivity, depth perception, and near-far focusing ability of the individual, and
    wherein the second display device is a wide-aspect display device which is used to measure visual perception span, eye-hand coordination, visual decision making, and reaction time of the individual.

7. The method for testing and/or training the visual abilities of an individual of claim 6, wherein:
    receiving the first input comprises using a multi-touch device capable of being engaged by the individual in response to the displayed at least one first visual indicia while the individual is visually far from the displayed at least one first visual indicia, and
    receiving the second input comprises using a touch sensitive display device capable of being engaged by the individual in response to the displayed at least one second visual indicia while the individual is visually near the displayed at least one second visual indicia.

8. The method for testing and/or training the visual abilities of an individual of claim 7, wherein the multi-touch device further comprises the second display device.

* * * * *